US006100450A

United States Patent [19]
Thomas et al.

[11] Patent Number: 6,100,450
[45] Date of Patent: Aug. 8, 2000

[54] SEED SPECIFIC PROMOTERS BASED ON ARABIDOPSIS GENES

[75] Inventors: Terry L. Thomas, College Station, Tex.; Michael Nuccio, Melrose, Fla.

[73] Assignee: Rhone-Poulenc Agrochimie, Lyons, France

[21] Appl. No.: 08/956,182

[22] Filed: Oct. 22, 1997

[51] Int. Cl.[7] .............................. C12N 15/82; C12N 5/04; C12N 15/29; A01H 5/00; A01H 4/00

[52] U.S. Cl. ......................... 800/287; 800/278; 800/281; 800/298; 800/312; 800/317.3; 800/314; 800/320.1; 800/322; 800/306; 435/419; 435/468; 435/320.1; 536/24.1; 536/23.6

[58] Field of Search ............................... 435/69.1, 252.3, 435/320.1, 412, 414–416, 419, 430, 410, 468; 536/23.6, 24.1, 24.5; 800/200, 205, 235, 250, 255, DIG. 9, 14, 17, 23, 26, 27, 43, 52, 56, 63, 66, 69, 278, 287, 290, 281, 295, 298, 312, 314, 317.3, 320.1, 322, 306

[56] References Cited

U.S. PATENT DOCUMENTS

| | | | |
|---|---|---|---|
| 5,057,419 | 10/1991 | Martin et al. | 435/134 |
| 5,420,034 | 5/1995 | Kridl et al. | 435/240.4 |
| 5,552,306 | 9/1996 | Thomas et al. | 435/134 |
| 5,614,393 | 3/1997 | Thomas et al. | 435/134 |
| 5,623,067 | 4/1997 | Vandekerckhove et al. | 536/24.1 |

OTHER PUBLICATIONS

Kim et al, A 20 nucleotide upstream element is essential for the nopaline synthase (nos) promoter activity, Plant Mol. Biol., vol. 24, pp. 106, 107, 110, 1994.
Nuccio et al, Identification of novel mRNAs in immature seeds of *Arabidopsis thaliana*, SAAS Bulletin: Biochem. & Biotech., vol. 9, pp. 24–26, 1996.
Altschul, et al. (1990) "Basic Local Alignment Search Tool", *J. Mol. Biol.*, 215:403–410.
Barton, et al. (1983) "Regeneration of Intact Tobacco Plants Containing Full Length Copies of Genetically Engineered T–DNA, and Transmission of T–DNA to R1 Progeny", *Cell*, 32:1033–1043.
Bechtold, et al. (1993) "In Planta Agrobacterium Mediated Gene Transfer by Infiltration of Adult *Arabidopsis thaliana* Plants", *C.R. Acad. Sci. Paris*, 316:1194–1199.
Bevan, M. (1984) "Binary Agrobacterium Vectors for Plant Transformation", *Nucleic Acids Research*, 12(22):8711–8721.
Bogue, et al. (1990) "Developmentally Regulated Expression of a Sunflower 11S Seed Protein Gene in Transgenic Tobacco", *Mol. Gen. Genet.*, 222:49–57.
Bustos, et al. (1991) "Positive and Negative cis–Acting DNA Domains are Required for Spatial and Temporal Regulation of Gene Expression by a Seed Storage Protein Promoter", *The EMBO Journal*, 10:6, 1469–1479.
Bustos, et al. (1989) "Regulation of β–Glucuronidase Expression in Transgenic Tobacco Plants by an A/T–Rich, cis–Acting Sequence Found Upstream of a French Bean β–Phaseolin Gene", *The Plant Cell*, 1:839–853.

Calzone, et al. (1987) "Mapping of Gene Transcripts by Nuclease Protection Assays and cDNA Primer Extension", *Methods in Enzymology*, 152:611–632.
Choi, et al. (1995) "Construction and Characterization of a Bacterial Artificial Chromosome Library of *Arabidopsis thaliana*", *Plant Molecular Biology Reporter*, 13(2):124–128.
Choi, et al. "Construction and Characterization of a Bacterial Artificial Chromosome Library of *Arabidopsis thaliana*", *Weeds World*, 2(i):17–20.
Crouch, et al. (1983) "cDNA Clones for *Brassica napus* Seed Storage Proteins: Evidence from Nucleotide Sequence Analysis that Both Subunits of Napin are Cleaved from a Precursor Polypeptide", *J. Mol. Appl. Genet.*, 2:273–283.
da Silva Conceição, et al. (1994) "A Cotyledon Regulatory region is Responsible for the Different Spatial Expression Patterns of Arabidopsis 2S Albumin Genes", *The Plant Journal*, 5(4):493–505.
Devereux, et al. (1994) "A Comprehensive Set of Sequence Analysis Programs for the VAX", *Nucleic Acids Research*, 12(1):387–395.
Feinberg, et al. (1983) "A Technique for Radiolabeling DNA Restriction Endonuclease Fragments to High Specific Activity", *Analytical Biochemistry*, 132:6–13.
Frandsen, et al. (1996) "Novel Plant $Ca^{2+}$–binding Protein Expressed in Response to Abscisic Acid and Osmotic Stress", *The Journal of Biological Chemistry*, 271(1):343–348.
Frugoli, et al. (1996) "Catalase is Encoded by a Multigene Family in *Arabidopsis thaliana* (L.) Heynh", *Plant Physiol.*, 112:327–336.
Fu, et al. (1995) "A Potato Sus3 Sucrose Synthase Gene Contains a Context–Dependent 3' Element and a Leader Intron With Both Positive and Negative Tissue–Specific Effects", *The Plant Cell*, 7:1395–1403.
Galau, et al. (1981) "Cotton Messenger RNA Sequences Exist in Both Polyadenylated and Nonpolyadenylated Forms", *The Journal of Biological Chemistry*, 265(5):2551–2560.

(List continued on next page.)

*Primary Examiner*—David T. Fox
*Assistant Examiner*—Ashwin D. Mehta
*Attorney, Agent, or Firm*—Scully, Scott, Murphy & Presser

[57] ABSTRACT

The present invention is directed to 5' regulatory regions of two Arabidopsis seed-specific genes, AtS1 and AtS3. The 5' regulatory regions, or parts thereof, when operably linked to either the coding sequence of a heterologous gene or a sequence complementary to a native plant gene, direct expression of the coding sequence or complementary sequence in a plant seed. The regulatory regions are useful in expression cassettes and expression vectors for the transformation of plants. Also provided are methods of modulating the levels of a heterologous gene such as a fatty acid synthesis or lipid metabolism gene by transforming a plant with the subject expression cassettes and expression vectors.

45 Claims, 29 Drawing Sheets

(7 of 29 Drawing Sheet(s) Filed in Color)

OTHER PUBLICATIONS

Gaubier, et al. (1993) "Two Different Em–like Genes are Expressed in *Arabidopsis thaliana* Seeds During Maturation", *Mol. Gen. Genet.*, 238:409–418.

Goldberg, et al. (1989) "Regulation of Gene Expression During Plant Embryogenesis", *Cell*, 56:149–160.

Guerche, et al. (1990) "Differential Expression of the Arabidopsis 2S Albumin Genes and the Effect of Increasing Gene Family Size", *The Plant Cell*, 2:469–478.

Guiltinan, et al. (1990) "A Plant Leucine Zipper Protein That Recognizes an Abscisic Acid Response Element", *Science*, 250:267–271.

Herrera–Estrella, et al. (1983) "Chimeric Genes as Dominant Selectable Markers in Plant Cells", *The EMBO Journal*, 2(6):987–995.

Horsch, et al. (1984) "Inheritance of Functional Foreign Genes in Plants", *Science*, 223:496–498.

Horsch, et al. (1985) "A Simple and General Method for Transferring Genes Into Plants", *Science*, 227:1229–1231.

Jefferson, R.A. (1987) "Assaying Chimeric Genes in Plants: The GUS Gene Fusion System", *Plant Molecular Biology Reporter*, 5(4):387–405.

Jefferson, et al. (1987) "GUS Fusions: β–Glucuronidase as a Sensitive and Versatile Gene Fusion Marker in Higher Plants", *The EMBO Journal*, 6(13):3901–3907.

Jordano, et al. (1989) "A Sunflower Helianthinin Gene Upstream Sequence Ensemble Contains an Enhancer and Sites of Nuclear Protein Interaction", *The Plant Cell*, 1:855–866.

Klee, et al. (1987) "Agrobacterium–Mediated Plant Transformation and its Further Applications to Plant Biology", *Ann. Rev. Plant Physiol.*, 38:467–486.

Klein, et al. (1987) "High–Velocity Microprojectiles for Delivering Nucleic Acids into Living Cells", *Nature*, 327:70–73.

Konieczny, et al. (1993) "A Procedure for Mapping Arabidopsis Mutations Using Co–Dominant Ecotype–Specific PCR–Based Markers", *The Plant Journal*, 4(2):403–410.

Kowalski, et al. (1994) "Comparative Mapping of *Arabidopsis thaliana* and *Brassica oleracea* Chromosmes Reveals Islands of Conserved Organization", *Genetics*, 138:499–510.

Lam, et al. (1995) "Use of Arabidopsis Mutants and Genes to Study Amide Amino Acid Biosynthesis", *The Plant Cell*, 7:887–898.

Lander, et al. (1987) "Mapmaker: An Interactive Computer Package for Constructing Primary Genetic Linkage Maps of Experimental and Natural Populations", *Genomics*, 1:174–181.

Larkin, et al. (1993) "Arabidopsis Glabrous1 Gene Requires Downstream Sequences for Function", *The Plant Cell*, 5:1739–1748.

Li, et al. (1995) "A Near–Upstream Element in a Plant Polyadenylation Signal Consists of More Than Six Nucleotides", *Plant Molecular Biology*, 28:927–934.

Liang, et al. (1993) "Distribution and Cloning of Eukaryotic mRNAs by Means of Differential Display: Refinements and Optimization", *Nucleic Acids Research*, 21(14):3269–3275.

Liang, et al. (1992) "Differential Display of Eukaryotic Messenger RNA by Means of the Polymerase Chain Reaction", *Science*, 257:967–971.

Lister, et al. (1993) "Recombinant Inbred Lines for Mapping RFLP and Phenotypic Markers in *Arabidopsis thaliana*", *The Plant Journal*, 4(4):745–750.

Maldonado–Mendoza, et al. (1996) "Molecular Analysis of a New Member of the Opium Poppy Tyrosine/3,4–Dihydroxyphenylalanine Decarboxylase Gene Family", *Plant Physiol.*, 110:43–49.

Marcotte, et al. (1989) "Abscisic Acid–Responsive Sequences from the Em Gene of Wheat", *The Plant Cell*, 1:969–976.

Marks, et al. (1987) "The Relatively Large Beta–Tubulin Gene Family of Arabidopsis Contains a Member With an Unusual Transcribed 5' Noncoding Sequence", *Plant Molecular Biology*, 10:91–104.

McClelland, et al. (1995) "RNA Fingerprinting and Differential Display Using Arbitrarily Primed PCR", *TIG*, 11(6):242–246.

Napoli, et al. (1990) "Introduction of a Chimeric Chalcone Synthase Gene Into Petunia Results in Reversible Co–Suppression of Homologous Genes in Trans", *The Plant Cell*, 2:279–289.

Nuccio, et al. (1996) "Identification of Novel mRNAs in Immature Seeds of *Arabidopsis thaliana*", *Biochem. & Biotech.*, 9:23–28.

Nunberg, et al. (1994) "Developmental and Hormonal Regulation of Sunflower Helianthinin Genes: Proximal Promoter Sequences Confer Regionalized Seed Expression", *The Plant Cell*, 6:473–486.

Pang, et al. (1988) "Molecular Cloning, Genomic Organization, Expression and Evolution of 12S Seed Storage Protein Genes of *Arabidopsis thaliana*", *Plant Molecular Biology*, 23:805–820.

Pérez–Callejón, et al. (1993) "Identification and Molecular Cloning of Two Homologues of Protein Phosphatase X from *Arabidopsis thaliana*", *Plant Molecular Biology*, 23:1177–1185.

Sieburth, et al. (1997) "Molecular Dissection of the AGAMOUS Control Region Shows that cis Elements for Spatial Regulation are Located Intragenically", *The Plant Cell*, 9:355–365.

Sjödahl, et al. (1993) "Cruciferin Gene Families are Expressed Coordinately But With Tissue–Specific Differences During *Brassica napus* Seed Development", *Plant Molecular Biology*, 23:1165–1176.

Taylor, et al. (1993) "Isolation and Characterization of Plant DNAs", *Methods in Plant Molecular Biology and Biotechnology*, pp. 37–47.

Thomas, T.L. (1993) "Gene Expression During Plant Embryogenesis and Germination: An Overview", *The Plant Cell*, 5:1401–1410.

Valvekens, et al. (1988), "*Agrobacterium tumefaciens*—Mediated Transformation of *Arabidopsis thaliana* Root Explants by Using Kanamycin Selection", *Proc. Natl. Acad. Sci.*, 85:5536–5540.

van der Krol, et al. (1990) "Inhibition of Flower Pigmentation by Antisense CHS Genes: Promoter and Minimal Sequence Requirements for the Antisense Effect", *Plant Molecular Biology*, 14:457–466.

Vielle–Calzada, et al. (1996) "Comparative Gene Expression in Sexual and Apomictic Ovaries of *Pennisetum ciliare* (L.) Link", *Plant Molecular Biology*, 32:1085–1092.

Worley, et al. (1995) "*Beauty*: An Enhanced Blast–based Search Tool that Integrates Multiple Biological Information Resources into Sequence Similarity Search Results", *Genome Research*, 5:173–184.

Young Kim, et al. (1997) "Isolation of a Novel Class of bZIP Transcription Factors that Interact with ABA–Responsive and Embryo–Specification Elements in the Dc3 Promoter Using a Modified Yeast One–Hybrid System", *The Plant Journal*, 11(6):1237–1251.

Zambryski, et al. (1983) "Ti Plasmid Vector for the Introduction of DNA Into Plant Cells Without Alteration of Their Normal Regeneration Capacity", *The EMBO Journal*, 2(12):2143–2150.

AtS1

AtS3

(A) AtS1 cDNA 3'-terminus alignment

```
1-6      ttgcagctct aaagaaaagc ttctgtatgt tttgttgcct tggtctctct    50
1-5      ttgcagctct aaagaaaagc ttctgtatgt tttgttgcct tggtctctct    50
1-4      ttgcagctct aaagaaaagc ttctgtatgt tttgttgccAn----------    39
1-3      ttgcagctct aaagaaaagc ttctgtatgt tttAn----- ----------    33
1-2      ttgcagctct aaagaaaagc ttctgtaAn- ---------- ----------    27
1-1      ttgcagctct aaagaaaaAn ---------- ---------- ----------    18

Genomic  TTGCAGCTCT AAAGAAAAGC TTCTGTATGT TTTGTTGCCT TGGTCTCTCT    50

1-6      ttgtaccaac ccctttttct gttatttcca attttacact gttagttatt   100
1-5      ttgtaccaac ccctttttct gttatttcca attttacact gttagttatt   100
1-4      ---------- ---------- ---------- ---------- ----------    39
1-3      ---------- ---------- ---------- ---------- ----------    33
1-2      ---------- ---------- ---------- ---------- ----------    27
1-1      ---------- ---------- ---------- ---------- ----------    18

Genomic  TTGTACCAAC CCCTTTTTCT GTTATTTCCA ATTTTACACT GTTAGTTATT   100

1-6      attgctaaat ttattactga cttactctaAn                         133
1-5      attgctaaat An-------- ---------- ---                      110
1-4      ---------- ---------- ---------- ---                       39
1-3      ---------- ---------- ---------- ---                       33
1-2      ---------- ---------- ---------- ---                       27
1-1      ---------- ---------- ---------- ---                       18

Genomic  ATTGCTAAAT TTATTACTGA CTTACTCTAA                          133
```

FIG.4A (B) AtS3 cDNA 3'terminus alignment

```
3-6      ttacttattc aagtatgtgc gcatgagttc ctgttagcta tgattattaa    50
3-5      ttacttattc aagtatgtgc gcatgagttc ctgttagcta tgaAn-----    43
3-4      ttacttattc aagtatgtgc gcatgagttc ctgttaAn-- ----------    36
3-3      ttacttattc aagtatgtgc gcatgagttc ctgtAn---- ----------    34
3-2      ttacttattc aagtatgtgc gcatgaAn-- ---------- ----------    26
3-1      ttacttattc aagtaAn--- ---------- ---------- ----------    15

Genomic  TTACTTATTC AAGTATGTGC GCATGAGTTC CTGTTAGCTA TGATTATTAA    50

3-6      atcagttggt accgacaAn 67
3-5      ---------- -------   43
3-4      ---------- -------   36
3-3      ---------- -------   34
3-2      ---------- -------   26
3-1      ---------- -------   15

Genomic  ATCAGTTGGT ACCGACA   67
```

FIG.4B

```
cgaattactg aatttagcag acaagaatag aaagagtgat gaaacatgga agaaaacgtg tctctagagt      1050
catgtcaagt gtaagacaga ggaagagaga agagatgtgc gtcaaagaca aggaaagaga gatgtcaatc      1120
gctgctttcg tcggcgcgtg catgtccgcc acgcacatca atcaaatcga tcttattatt attacctcat     1190
tatactcTTT ACTCTAAGAC AAACACATAC ATTTGCACTC AGTCTAGAGA CAAAGAGAGA GAGAGATGGG      1260
                                                                         M  G
GTCAAAGACG GAGATGATGG AGAGAGACGC AATGGCTACG GTGGCTCCCT ATGCGCCGGT CACTTACCAT      1330
 S  K  T    E  M  M    E  R  D  A  M  A  T   V  A  P  Y  A  P  V   T  Y  H
CGCCGTGCTC GTGTTGACTT GGATGATAGA CTTCCTAAAC CTTgtaaacc tgtctctcgc tacttgcatt      1400
 R  R  A  R  V  D  L   D  D  R    L  P  K  P  Y
tttttatccc taattgattt caatatattg catgccaaaa aacatttgat atatggttga atttaagaaa      1470
cccttttaaa tatatggaat tgccgaccct caaaattttt aaaacatgca tatagaatga tgttcatgat      1540
cttatagaag ctataaattg taaaatgata catatcctgt atatgatggt aattaataat gtattaccca      1610
tgaacgtgca tgaataattc tatacacaca ttacacatac gtggaaatga tacagatttt gacttatatg      1680
tgttatgcat agATATGCCA AGAGCATTGC AAGCACCAGA CAGAGAACAC CCGTACGGAA CTCCAGGCCA      1750
             M  P  R   A  L  Q    A  P  D    R  E  H    P  Y  G  T  P  G  H
TAAGAATTAC GGACTTAGTG TTCTTCAACA GCATGTCTCC TTCTTCGATA TCGATGATAA TGGCATCATT      1820
 K  N  Y    G  L  S  V  L  Q  Q   H  V  S    F  F  D  I  D  D  N   G  I  I
TACCCTTGGG AGACCTACTC TGgtatgtct atatagtata tatagatatt tcaacttcaa attttttcgtt     1890
 Y  P  W  E  T  Y  S   G
agtattatat gtacaaaaag ttgatcccaa ccggtgatta gGACTGCGAA TGCTTGGTTT CAATATCATT      1960
                                              L  R  M   L  G  F    N  I  I
GGGTCGCTTA TAATAGCCGC TGTTATCAAC CTGACCCTTA GCTATGCCAC TCTTCCGgta acacctctcc      2030
 G  S  L  I  I  A  A   V  I  N    L  T  L  S  Y  A  T   L  P
tcctctgctg acatatatcg caaaactttg attgattcta ctctagactc ggaaattatc atatccaaat      2100
ccgttgtcca ttttgttagt gttctacttg attatatgca gGGGTGGTTA CCTTCACCTT TCTTCCCTAT      2170
                                               G  W  L   P  S  P  F  F  P  I
ATACATACAC AACATACACA AGTCAAAGCA TGGAAGTGAT TCAAAAACAT ATGACAATGA AGGAAGgtga      2240
 Y  I  H    N  I  H  K  S  K  H   G  S  D    S  K  T  Y  D  N  E   G  R
gtgaccatat tatcttgaaa aaaacggttg actgatagaa aatatgatga ctgatgcata tggtataact      2310
tccgtatgct tttcagGTTT ATGCCGGTGA ATCTTGAGTT GATATTTAGC AAATATGCGA AAACCTTGCC      2380
                 F    M  P  V  N  L  E  L    I  F  S    K  Y  A  K  T  L  P
AGACAAGTTG AGTCTTGGAG AACTATGGGA GATGACAGAA GGAAACCGTG ACGCTTGGGA CATTTTTGGA      2450
 D  K  L    S  L  G  E  L  W  E   M  T  E    G  N  R  D  A  W  D   I  F  G
TGgtacaatc acagcattag ccttccttt tcttacccctt tcattagttt attgaatgca tgtgttaaac     2520
W
taaagtatta gtcaatgttg ttgtagttat aatgtttgga tctacatgta tgtattagGA TCGCAGGCAA      2590
                                                                I  A  G  K
AATAGAGTGG GGACTGTTGT ACTTGCTAGC AAGGGATGAA GAAGGGTTTT TGTCAAAAGA AGCTATTAGG      2660
 I  E  W    G  L  L  Y  L  L  A   R  D  E    E  G  F  L  S  K  E   A  I  R
CGGTGTTTCG ATGGAAGCTT GTTCGAGTAC TGTGCCAAAA TCTACGCTGG TATCAGTGAA GACAAGACAG      2730
 R  C  F  D  G  S  L   F  E  Y    C  A  K  I  Y  A  G   I  S  E    D  K  T  A
CATACTACta aaagtatcct ttatgttaag taattgatcg agccatttta agctaataat cgctcaatgt      2800
 Y  Y
gaagcttgtg cctatacggt aaatgaaggt tcgggtagta gtatggactt tggtctaag agatctatgt      2870 ttgttttgt ttttccagtt ctgtatggtt atactataag ttgcagctct aagaaaagc ttctgtatgt      2940
                                                         *                *
tttgttgcct tggtctctct ttgtaccaac cccttttttct gttatttcca attttacact gttagttatt     3010
  *    *
attgctaaat ttattactga cttactctat agtagtgtaa cgaatatatg gtcacattaa ctcaaagtta     3080
       *                              *
actccactcc atgaacattg aagcactgag aatccaggac ctatgaatca acgcaatcaa agaaagagaa      3150
agttagtaac accttcatga aggagagtct taaagaaaa gaagaaaaga ttaaaacacc ttcatgaaag      3220
agagtcttga acttgaatag tatactagtc cttttagagt cttgaagttt gaatagtata ctagttcttt      3290
```

FIG. 8

```
aaaatgtaag aaggaatagt acaatataga acggtaaaaa aaatggcaaa ccatttactt caataagaaa    1050
ggttagcaac cacactcagc aaatgggaca cataggatcc gacgtggttt atattatagt agtctgatat    1120
tgtagagtca atgggtatat ttgtcttttt caaagactca gttccattga agcgtaggtt acttctttaa    1190
acaagactct gttttgaatg atattgtaaa gttaaggggt acgtttgtct ttttcaggac aaagcgagac    1260
catagatgac gtgtcaactg ctaattttca aaaactcggt ctacaaacca taaggaaact tatttattca    1330
attatttccg tcaaaaaaat ataattttct ttttgcatct caatggattg attccatgtg ccaagtgttg    1400
gtgttcatga gaaaattagt cgcagctgat gacaacaaac atcaagcatt tataatttat ataacactca    1470
cgAGTGCCTC TTTCTTTATC TACCTCGTCT CCTAATCACA AACACACACA AATCTCTGAA GTAAAATGAC    1540
                                                                      M  T
GTTCCCTTCT CTTTCTGTCT CATTTCTCTT CTTTGCCTTC ATATTCGTTA CGCATGCATT CGACCTCAGC    1610
 F  P  S    L  S  V  S    F  L  F    F  A  F    I  F  V  T    H  A  F    D  L  S
ATCATCCAGg ttcttcttgt tttctacttt ctggctaaca aagtaaccag aaccggtttt ctcacttgta    1680
 I  I  Q
tatttgtttt tttgagaaaa tcatgtagAT GCAACAGGGA ACATGTCCGT ACACGGTGGT TGTCATGACA    1750
                       M  Q  Q  G    T  C  P  Y    T  V  V    V  M  T
AGCTGTCTTT CTCCGGAGTC GACAAGAGAT CAGATCAGCA TTGTTTTTGG CGATGCCGAC GGTAACAAGg    1820
 S  C  L  S    P  E  S    T  R  D    Q  I  S  I    V  F  G    D  A  D    G  N  K
ttaagtaact agatttttt gtatatagtt ccagttaagt cgacatcttt atttgcttta aagtggttta    1890
gataccttgc atgcatgcat gtgtgctcaa tacaagtaac ttcttagtga tttaaataaa atgttaaata    1960
tatatctttt tgttttagGT GTATGCACCG AAACTAGGGG TTCGGTAAG AGGACCAGGG GGTTTGGGAA    2030
                 V   Y  A  P    K  L  G  G    S  V  R     G  P  G    G  L  G  K
AGTGTTCAAC GAACACATTC CAAGTCAGAG GTCAATGTTT AAATGACCCT ATCTGCTCTC TCTATATCAA    2100
 C  S  T    N  T  F    Q  V  R  G    Q  C  L    N  D  P    I  C  S  L    Y  I  N
CCGGAATGGA CCCGATGGCT GGGTCCCGGA GTCCATTGAG ATCTACTCAG AAGGTTCAAA GTCCGTTAAA    2170
 R  N  G    P  D  G  W    V  P  E    S  I  E    I  Y  S  E    G  S  K    S  V  K
TTCGATTTCA GCAAGAGCGT CCCTCAACTA AACACTTGGT ACGGCCACAA CAACTGCAAC ACCACAGGCA    2240
 F  D  F  S    K  S  V    P  Q  L    N  T  W  Y    G  H  N    N  C  N    T  T  G  R
GACCATCGTC TCCCGATCTG CCTCCACCGC ATTTTCCGCC AGAGTTTCCA CCGGAGACAC CTACCACCCC    2310
 P  S  S    P  D  L    P  P  P  H    F  P  P    E  F  P    P  E  T  P    T  T  P
ACCGCCGCCT CCACCAAGGC CGTCTGCTGC TTCAAGGCTT GGAAATGGTG AGAGTGTTTT CCTTGCGTTT    2380
 P  P  P    P  P  R  P    S  A  A    S  R  L    G  N  G  E    S  V  F    L  A  F
GCCATTGCGA CTGCGATTGC CGCAATGGTG CGTTGGAGTT ACtagcatgg tacttgaaga gcatgttgtt    2450
 A  I  A  T    A  I  A    A  M  V    R  W  S  Y
gggttgtatg aggcttttc tttccgtcga atgttttat ttgctttcgt tttgcttcag ccttttcctt    2520
gttgtagaaa acataattac ttattcaagt atgtgcgcat gagttcctgt ttagctatga ttattaatca    2590
                                *                 *          **        *
gttggtaccg acatttagta gttcattttc aaaagagaat ccatcacttg tgcatagaaa taaagattaa    2660
              *
aaaatccat cactttccat aaccggtgtt tggacttgca atttttagc gagacagtat gataattttt    2730
tttttaaagt acatatatgc taatcagtga tccaattttt aacaattgag atgaagattt atccaaaaac    2800
tggtgtatca taccaaatta tcaatagatt atattgagac aaacaaggat ataatttaaa taatttggac    2870
aacaaacctc aactcaaggc acatttgatg acatttcaag gaaaacataa atggacctaa cttttgattc    2940
gaattgttat tgaagtgttg tcgaaaactg gaatgcatgg aatttgtcag gtagtagtag gtggagttca    3010
tgggagaagt cgaaacacgt aaacaactct tctcttttag acaaattct tcttttttcg gacatctggt    3080
ttcacgtgtc cttgacctaa aatcgggatt aaatatggct tatattgatg ttacaccgag ccatttcat    3150
tttcttttac ttaaatcaaa ttgtctattg atgttaatcc gacaattttt atttattttt actgattttg    3220
tttttgagat gttgttcttt taagtcacca taaaattaaa aaaaaaaaaa aaaagagag agagaaggta    3290
```

FIG. 9

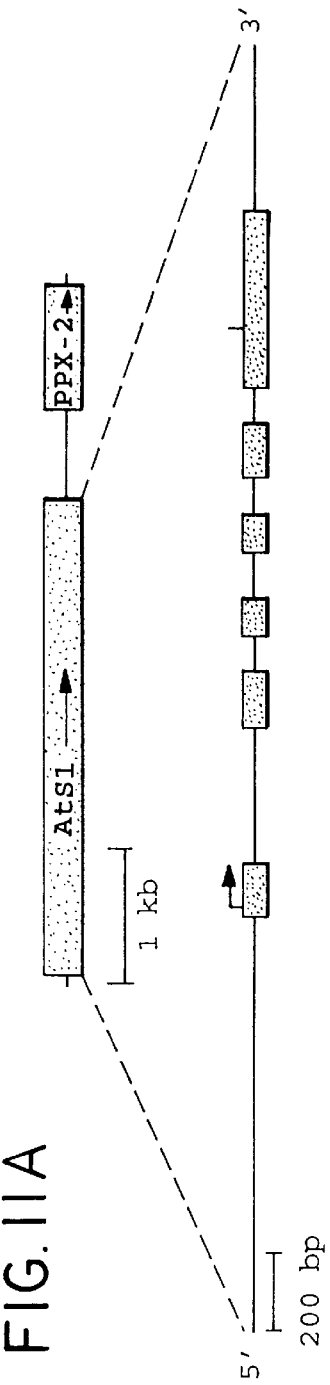
FIG. IIA
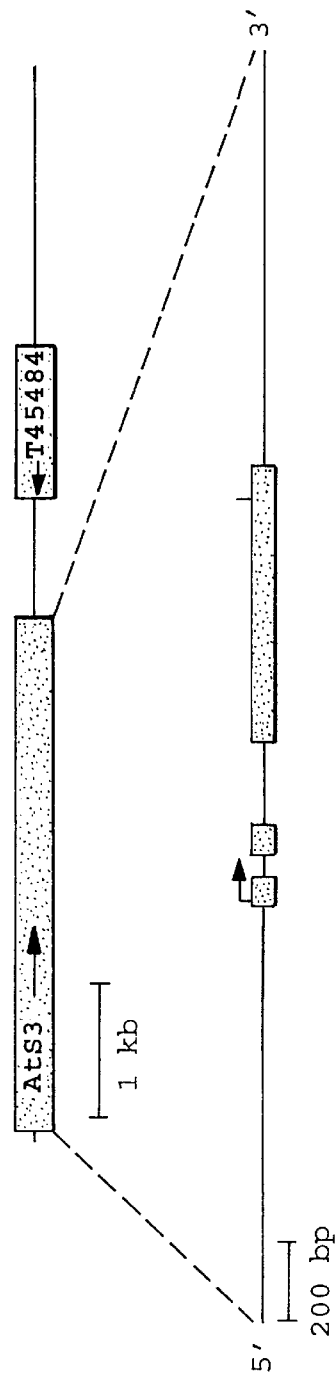
FIG. IIB 60.9% identical

```
                10         20         30         40         50         60         70
AtS1    ATGGGGTCAAAGACGGAGATGATGGA------GAGAGACGCAATGGCTACGGTGGCTCCCTATGCGCCGGTCACT
        ::::  :   :: :::   :   ::       ::   ::  ::   ::  :   ::::: ::   : :::::::: ::
EFA27   ATGGCGGAGGAGGCGGCTAGCAAGGCAGCGCCGACCGATGCGCTGTCGTCCGTGGCGGCGGAGGCGCCGGTGACG
                10         20         30         40         50         60         70

AtS1    TACCATCGCCGTGCTCGTGTTGACTTGGATGATAGACTTCCTAAACCTTATATGCCAAGAGCATTGCAAGCACCA
        : ::: :   : ::    ::::::::: :     :::: ::  ::: :: :   :::: ::    :: ::
EFA27   AGAGAACGGCCGGTCCGAGCGGACTTGGAAGTGCAGATTCCGAAGCCCTATTTGGCCCGAGCTCTGGTTGCTCCG

AtS1    GACAGAGAACACCCGTACGGAACTCCAGGCCATAAGAATTACGGACTTAGTGTTCTTCAACAGCATGTCTCCTTC
        :::       : :: ::   : :::::      ::  :  :   :       : :::::  :: ::::::::   : :::
EFA27   GACGTGTACCATCCTGAAGGAACCGAGGGGCGTGACCACCGGCAGATGAGTGTGCTGCAGCAGCATGTGGCTTTC

AtS1    TTCGATATCGATGATAATGGCATCATTTACCCTTGGGAGACCTACTCTGGACTGCGAATGCTTGGTTTCAATATC
        :::::    : ::::      :  :: :::  ::::  :: ::  :: ::     :::::  ::    :  :: :::::   :
EFA27   TTCGACCTGGATGGCGACGGTATCGTTTATCCATGGGAAACTTATGGAGGACTACGGGAATTGGGCTTCAACGTG

AtS1    ATTGGGTCGCTTATAATAGCCGCTGTTATCAACCTGACCCTTAGCTATGCCACTCTTCCGGGGTGGTTACCTTCA
        ::::    :::  :    : ::     :: :::  :   ::  :::::  :   :::::  :: :   :::  :::: ::
EFA27   ATTGTTTCGTTCTTTTTGGCGATAGCCATAAACGTTGGTCTAAGCTACCCAACTCTGCCAAGCTGGATACCATCT

AtS1    CCTTTCTTCCCTATATACATACACAACATACACAAGTCAAAGCATGGAAGTGATTCAAAAACATATGACAATGAA
        :    :   :::::::::  :::::  :  :::::  ::::   :: ::  ::  :::              :: ::  :::::  ::
EFA27   CTCCTGTTCCCTATACACATAAAAAACATCCACAGGGCTAAGCACGGCAGCGATAGCTCGACGTACGACAACGAG

AtS1    GGAAGGTTTATGCCGGTGAATCTTGAGTTGATATTTAGCAAATATGCGAAAACCTTGCCAGACAAGTTGAGTCTT
        :::::::::::::::::: :::  :   : :::  ::  :: :::::   :  :::      ::  :::  :::::: :  :
EFA27   GGAAGGTTTATGCCGGTCAATTTCGAGAGCATCTTCAGCAAGAACGCCCGCACGGCGCCGGACAAGCTCACGTTC

AtS1    GGAGAACTATGGGAGATGACAGAAGG--AAACCGTGACGCTTGGGACATTTTTGGATGGATCGCAGGCAAAATAG
        ::  ::  :  :::  :::::: :::::      :::   :::  ::::  :   ::::  :: ::  :::::  :   :::       :
EFA27   GGCGATATCTGGCGGATGACCGAAGGCCAAAGGGTGGCGCTCG--ACTTGCTTGGGAGGATCGCGAGTAAGGGGG

AtS1    AGTGGGGACTGTTGTACTTGCTAGCAAGGGATGAAGAAGGGTTTTTGTCAAAAGAAGCTATTAGGCGGTGTTTCG
        ::::::  :  :: :::  :::: ::  :  :::::  :::::  ::           ::   ::  ::: ::  :   ::  ::::
EFA27   AGTGGATATTGCTCTACGTGCTTGCGAAAGATGAGGAAGGATTCCTCAGGAAGGAGGCTGTTCGCCGCTGCTTCG
                                                            710        720        730
ATS1    ATGAAGCTTGTTCGAGTACTGTGCCAAAATCTACGCTGGTATCAGTGAAG-ACAAGACA-GCATACTAC
        ::::  :::   :  :::::::    :::: :          ::  :   ::  ::  :: ::: ::  ::  :   :     :
EFA27   ATGGGAGCCTATTCGAGTCGATTGCCCA-------GCAGAGA--AGGGAGGCACATGAGAAGCAGA--AG
                                                            710        720        730
```

FIG.15A

```
        64.4% identity in 222 residue overlap;  Score: 765.0;  Gap frequency: 0.0%

AtS1       23    DAMATVAPYAPVTYHRRARVDLDDRLPKPYMPRALQAPDREHPYGTPGHKNYGLSVLQQH
EFA27      13    DALSSVAAEAPVTRERPVRADLEVQIPKPYLARALVAPDVYHPEGTEGRDHRQMSVLQQH
                 **   **  ****  *  *  **    ****   ***  ***  ** **  *  ******

AtS1       83    VSFFDIDDNGIIYPWETYSGLRMLGFNIIGSLIIAAVINLTLSYATLPGWLPSPFFPIYI
EFA27      73    VAFFDLDGDGIVYPWETYGGLRELGFNVIVSFFLAIAINVGLSYPTLPSWIPSLLFPIHI
                 * *** *  ** ****** *** ****  *   *  *** ***  *  ** *** *** *

AtS1      143    HNIHKSKHGSDSKTYDNEGRFMPVNLELIFSKYAKTLPDKLSLGELWEMTEGNRDAWDIF
EFA27     133    KNIHRAKHGSDSSTYDNEGRFMPVNFESIFSKNARTAPDKLTFGDIWRMTEGQRVALDLL
                  *** ****** ************ * **** * ** ****  *  ** ****  *  * *

AtS1      203    GWIAGKIEWGLLYLLARDEEGFLSKEAIRRCFDGSLFEYCAK
EFA27     193    GRIASKGEWILLYVLAKDEEGFLRKEAVRRCFDGSLFESIAQ
                 *  ** * **  ***  ** ****** *** **********    *
```

FIG. 15B

```
          57.5% identity in 261 nt overlap; init:   177, opt:   258

240       250       260       270       280       290
AtS1     TTCTTCAACAG-CATGTCTCCTTCTTCGATATCGATGATAATGGCATCATTTACCCTTGG
         :::::  : :: X::::: : :: :::::::    :   : :::: ::: :::: :: : :
ATTS     TTCTTGCAGAGACATGTCGCTTTTTTCGATAGGAACAAAGATGGTATCGTTTATCCCTCG
               180       190       200       210       220       230

300       310       320       330       340
AtS1     GAGACCTACTCTGGACTGCGAATGCTT-GGTTTCAATATCATTGGGTCGCTTATAATAGC
         :::::  :    ::: :  ::   :: :::  :  ::   : ::    :  :::
ATTS     GAGACATTTCAAGGATTTAGAGCAATTGGGTGTGGATATTTGTTGTCAGC----AGTCGC
               240       250       260       270       280       290

350       360       370       380       390       400
AtS1     CGCTG---TTATCAACCTGACCCTTAGCTATGCCACTCTTCCGGGGTGGTTACCTTCACC
         :::   : ::  ::: :    ::  :::    ::::  ::::::     :    ::
ATTS     TTCTGTGTTCATAAACATAGGTCTCAGCAGCAAAACTCGTCCGGGTAAAGGATTCTCTAT
               300       310       320       330       340       350

410       420       430       440       450       460
AtS1     TTTCTTCCCTATATACATACACAACATACACAAGTCAAAGCATGGAAGTGATTCAAAAAC
         :  ::  ::::::  :    : :: :: :::    : :: :: ::::: :::::X
ATTS     CTGGTTTCCTATAGAGGTTAAGAATATTCACCTTGCCAAACACGGAAGCGATTCAGGCGT
               360       370       380       390       400       410

470       480
AtS1     ATATGACAATGAAGGAAGGTT
         ::  :::::: :: ::: ::::
ATTS     TTACGACAAAGATGGACGGTT
               420       430
```

FIG. 16A

```
        62.1% identity in 280 nt overlap; init:   223, opt:   362

270       280       290       300       310       320
EFA27    CCACCGGCAGATGAGTGTGCTGCAGCAGCATGTGGCTTTCTTCGACCTGGATGGCGACGG
         :::    : ::::  : : :   :::::    ::::: ::::: :::::   : :    :: X:
ATTS     CCAGAAGAAGAT-AATTTCTTGCAGAGACATGTCGCTTTTTTCGATAGGAACAAAGATGG
                 170       180       190       200       210       220

330       340       350       360       370       380
EFA27    TATCGTTTATCCATGGGAAACTTATGGAGGA-CTACGGGAATTGGGCTTCAACGTGATTG
         :::::::::::::: : ::: :: : :  :::: :: : :::::::: : : : :::
ATTS     TATCGTTTATCCCTCGGAGACATTTCAAGGATTTAGAGCAATTGGGTGTGGA--TATTTG
                 230       240       250       260       270

390       400       410       420       430       440
EFA27    TT-----TCGTTCTTTTTGGCGATAGCCATAAACGTTGGTCTAAGCTACCCAACTCTGCCA
         ::     :  :: :: ::   : : :  :::::::  : ::::: :::   :  ::::: ::
ATTS     TTGTCAGCAGTCGCTTCTGTGTT---CATAAACATAGGTCTCAGCAGCAAAACTCGTCCG
             280       290       300          310       320       330

450       460       470       480       490       500
EFA27    AG--CTGGATACCATCTCTCCTGTTCCCTATACACATAAAAAACATCCACAGGGCTAAGC
         :    :::: :   ::: ::  :::  ::::::  :  :: :: ::  :::    :: :: :
ATTS     GGTAAAGGATTC--TCTATCTGGTTTCCTATAGAGGTTAAGAATATTCACCTTGCCAAAC
             340       350       360       370       380       390

510       520       530       540
EFA27    ACGGCAGCGATAGCTCGACGTACGACAACGAGGGAAGGTT
         ::::  ::::::           :::::::::X :: ::: ::::
ATTS     ACGGAAGCGATTCAGGCGTTTACGACAAAGATGGACGGTT
             400       410       420       430
```

FIG. 16B

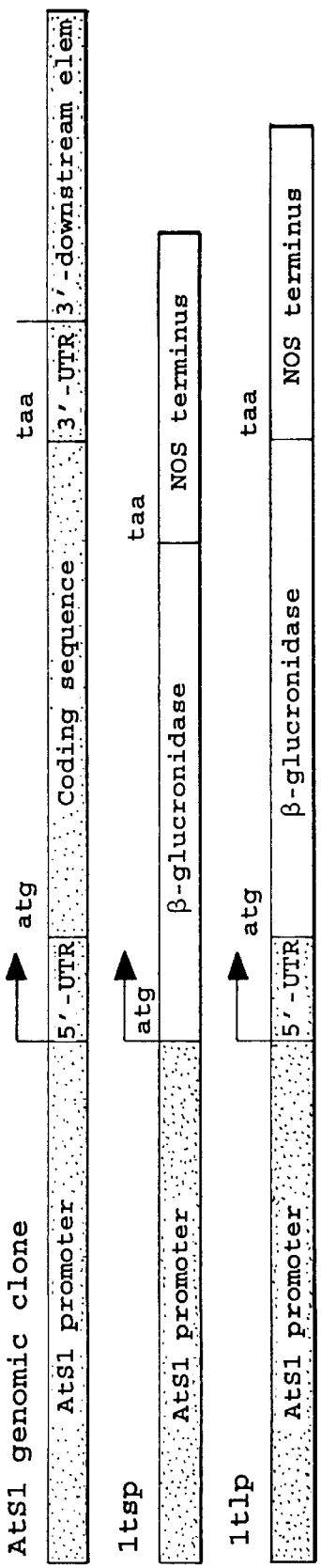
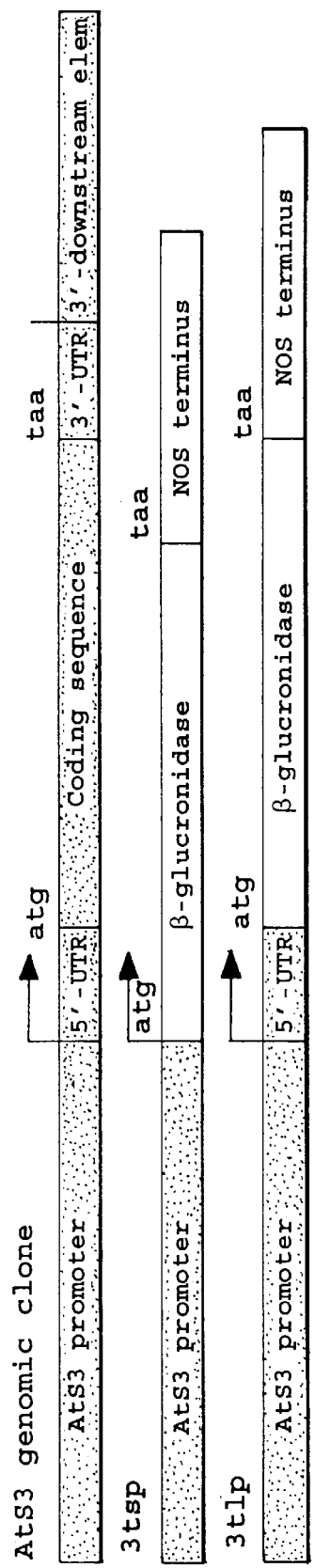
FIG. 18A
FIG. 18B

```
                                                    aagctCGATCCACCCCATGACTGAATGATGACTCCAGCCACCA   44
TCAATTCCCTGAAGTGCCACAACACCCTCTACCTCCCAGGTTTATGACAATCGACCAACGATTATCCCGCAGATGTCC            124
CACCTCCACCACCGTCTTCTTACCCTTCCAACGATCATCTTCCCCCTCCCACAGGACCATCAGACTCCCCTTACCCGCAT         204
CCTTACAGTCATCAACCATACCACCAAGACCCGCCAAAACACATGCCGCCACCGCAAAACTACTCATCTCATGAGCCTTC         284
TCCAAATTCTCTCCCTAATTTCCAATCTTATCCTAGCTTTAGTGAGACAGCCTCCCATCCACTTCTCCCCACTACCCTT          364
CTCACTACCAAAACCCAGAACCTTACTCATTCTTCTCCGCACTCTGCACCTCCTCCTCTTCCCACAAGCTTCTGCTCTGCT        444
CCTCCCTCCCACCTTACTCATCAAACGGGCGTATCAATATTGCTCCCCGTGCTAGATCCTGCACCGAGTTCAGCTCAGAA         524
GTACCATTACGATAGCAGCTACCAGCCAGGGCCTGAGAAGGTTGCAGAGGCACTCAAGGCTGCTAGATTCGCTGTGGGAG         604
CTTTGGCTTTTGATGAAGTCTCGACTGCTGTAGAACATCTCAAGAAGTCACTTGAGTTGCTAACAAATCCATCGGCCGGT         684
GCCGGTCACTGAATTTTATATCTAATCTATGACACTTGGGGTTGATGTTAGTGCGTGTGTGTTCTCACCACATTGTG           764
GGTTTGTTATTAACTTTTCAGGCTCAGACTTCGTTTACAAAGAAAATTTGTGTGAATTATTCTTATTATCATAAAATTT          844
TCCTTGCAACTTCGTGTACATTCATACATACATAGGCAATGGAGTTCCTCTTCAGTCTTCACGTAAAGAGCGAGTGTGGG         924
ACACGCACTCATGTAGCGGGTGTGGTGTTAGTACTCGAGGTTGGGCCTATATAAAAGCCCATAGAGGCCCGAATTACTGAAT       1004
TTAGCAGACAAGAATAGAAAGAGTGATGAAACATGGAAGAAAAACGTGTCTCTAGAGTCATGTCAAGTGTAAGACAGAGA         1084
AGAGAGAAGAGATGTGCGTCAAAGACAAGGAAAGAGAGATGTCAATCGCTGCTTTCGTCGGCGTCATGTCCGCCACG            1164
CACATCAATCAAATCGATTCTTATTATTATTACCTCATTATACTCTTTACTCCCTAGGCGCGATCCCCGGGTGGTCAGTT         1244
CCTT                                                                                    1248
```

FIG.23

```
BamH1
GGATCCACTAGTTCTAGAGCGGGCCGCCACCGCGGTGGAGCTCGATCCACCCATGACTCGAATGATGACTCCAGCCACCA    80
                     SacI

TCAATTCCCTGAAGTGCCACAACACCCTCTACCTCCCAGTTTTATGACAATCGACCAACGATTATCCCGCAGATGTCC       160

CACCTCCACCACCGTCTTCTTACCCTTCCAACGATCATCTTCCCCCTCCCACAGGACCATCAGACTCCCCTTACCCGCAT     240

CCTTACAGTCATCAACCATGACCCGCCAAAACATGCGCCACCGCAAAACTACTCATCTCATGAGCCTTC              320

TCCAAATTCTCTCCCTAATTCCAATCTTATCCTAGCTTTAGTGAGAGCAGCCTCCCATCCACTTCTCCCCACTACCCTT    400

CTCACTACCAAAACCCAGAACCTTACTATTCTTCTCCGCACTCTGCACCTGCTCTGCTCCTCCTTCTTCCACAAGCTTCTGCTCTGCT  480

CCTCCTCCTCCACCTTACTCATCAAACGGGCGTATCAATATTGCTCCCGTGCTAGATCCTGCACCGAGTTCAGCTCAGAA    560

GTACCATTACGATAGCAGCTACCAGCCAGGGCCTGAGAAGGTTGCAGAGGCACTCAAGGCTGCTAGATTCGCTGTGGGAG    640

CTTTGGCTTTTGATGAAGTCTCGACTGCTAGAACATCTCAAGAAGTCACTTGAGTTGCTAACAAATCCATCGGCCGGT      720

GCCGGTCACTGAATTTTATATCTAATCTATGACACTTGGGGTTGATGTTAGTGCGTGTGTGTTCTCACCACATTTGTG      800

GGTTTGTTATTAACTTTTCAGGCTCGTTACAAAGAAAATTGTGTGAATTATTCTTATTATCATAAAATTT               880

TCCTTGCAACTTCGTGTACATTCATACATAGGCAATGAGTTCCTCTCAGTCTTCACGTAAAGAGGCCGAGTGTGGG       960

ACACGCACTCATGTAGCGGGTGGTGTTAGTACTCGAGGTTGGGCCTATATAAAAGCCCATAGAGGCCCGAATTACTGAAT   1040

TTAGCAGACAAGAATAGAAAGAGTGATGAAACATGGAAGAAAACGTGTCTCTAGAGTCATGTCAAGTGTAAGACAGAGGA  1120

AGAGAGAAGAGATGTGCGTCAAAGACAAGGAAAGAGAGATGTCAATGCTGCTTTCGTCGGCGCGTGCATGTCCGCCACG   1280

CACATCAATCAAATCGATTCTTATTATTATTACCTCATTATACTCTTTACTCTAAGACAAACACATACATTTGCACTCAG  1360
                                        +1

TCTAGAGACAAAGAGAGAGCCATGG                                                            1387
                 NcoI
```

FIG. 24

```
XbaI
TCTAGATGCATGGAAGTAATTTTAATTAACCTATGTTTTAAACATTTACATTATTTGGAATTAATATTATATATACACT      80
ATTCGATTTGTTTCCTTCAATGTAACATTACTCTGGCAAAAGTATTTATCGTATAATATCTTTTATTATAAATTTTTG      160
ATGTTTTAAAGATTAGTTTATCTCTTTTGACCAAAAGAAAGAAAGGATTAGATTTATCTCTATGTGAACTTGATTA       240
TACGAGTTCGGATAATCGGATCTCAATGTGATATCCATATTCTTCAAGACATATCTCGTACACCTTTTATATTTAT      320
ATCCCGCAATCGTGACAACTCTTAATCATTCACTACATAATATTTCCAACAACATTAAAAGATATTTATCTTAATTCTCT   400
TTTTCCTTAACACTAACAAAGTAGCATGTCCATATACTTTCGTTTTTTGAGCATGAGAAATAGATTAACTTTTATAAG     480
TTATAACCATTGTTTTCAAATTAATGCAGATTCGAGTAATAATAATTGAGATGCAATAATGGTTGTCATATCTTGATT     560
GCTAAACTTGATACCGCCATACCGGTAACGTGAAGGGAGACTTCCAATTTGTATGCAAGCCTACATCTGACCCAATGT     640
TGGCCCAATATTAACCACACCCACTAAAAAAAAATACTATGGAGGGAGTAATCTACATGCCTACATTCCAAAGCAGGC    720
AATATCGTTTTTTCATGTCTGAAAACGCAATTTTTTTTTCTAATTGTTAAGTTGGTTCAAAAGAAATGAACATGGGTAAT   800
AATAAAAATGATGTATTTGTTTGCAAACAGCAGTTCTCACTTGTCTCTCTATATGATGAAAGACAATGTTGTAATCTT    880
TATAGGTTTCAATATAGCGGGTATACTTGGTGACATAAAGCGTTATGAAATTTAAGCAGTAAATAGGAAAATGATAAATG  960
ATTATTAAATTCGTTATTAAAAATGTAAGAAGGAATAGTACAATAGGGACACACTCAGCAAATGGGACACATAGGATCCGACGTGGTTTATATTATAGTAGTCTGATATT 1040
AATAAGAAAGGTTAGCAACCACACTCAGCAAATGGGACACATAGGATCCGACGTGGTTTATATTATAGTAGTCTGATATT 1120
GTAGAGTCAATGGGTATATTTGTCTTTTTCAAAGACTCCAGTTCCATTGAAGCGTAGGTTACTTCTTTAAACAAGACTCTG 1200
TTTTGAATGATATTGTAAAGTTAAGGGGTACGTTTGTCTTTTCAGGACAAAGCGAGACCATAGATGACGTGTCAACTGC   1280
TAATTTTCAAAAACTCGGTCTACAAACCATAACCAAACTTATTTATTCAATTATTTCCGTCAAAAAAATATAATTTTCTT  1360
TTTGCATCTCAATGGATTGATTCCATGCCAAGTGTTGGTGTTCATGAGAAATTAGTCGCAGCTGATGACAACAAACA     1440
TCAAGCATTTATAATTTATATAACACTCACGAGTGCCTCTTTCTTTGGATCCGCGGGGTGGTCAGTTCCTT            1510
                                                          gagtgctcacggagaagaaacctaggcgc5'
                                          +1
```

```
XbaI
TCTAGATGCATGGGAAGTAATTTTAATTAACCTATGTTTTAAACATTTACATTATTTGGAATAATATTATATATATACACT    80
ATTCGATTTTGTTTCCTTCAATGTAACATTACTCTGGCAAAAGTATTTATCGTATAATATCTTTTATTATAAATTTTTG     160
ATGTTTTAAAGATTAGTTTATCTCTTTTGACCAAAAAGAAAAGGGATTAGATTTATCTCTATGTGAACTTGATTA          240
TACGAGTTCGGATAATCGGATCTCAATGTGATATCCATATTTCTTGCAAGACATATCTCTGCACACCTTTTATATTTAT     320
ATCCCGCAATCGTGACAACTCTTAATCATTCACTACTACATATATTTCCAACACATTAAAAGATATATTTATCTTAATTCTCT 400
TTTCCTTAACACTAACAAAGTAGCATGTCCATATATACTTTCGTTTTTTGAGCATGAGAAAATAGATTAACTTTATAAG    480
TTATAACCATTGTTTCAAATTAATGCAGATTCGAGTAATAATTTGAGATGCAATAATGGTTGTGTCATATCTTGATT     560
GCTAAACTTGATACCGCCATACCGGTAACGTGAAGGGAGAGCTTCCAATTTGTATGCAAGCCTACATCTGACCCAATTGT    640
TGGCCCAATATTAACCAACACCCCACACTAAAAAAAAATACTATGGAGGGAGTAATCTACATGCCTACATTCCAAAGCAGGC  720
AATATCGTTTTTTCATGTCTGAAAAACGCAATTTTTTTTCTAATTGTTAAGTTGGTTCAAAGAAATGACATGGGTAAT     800
AATAAAATGATGTATTTGTTTGCAAACAGCAGTTCTCACTTGTCTCTCTCTATATGATGAAAGACAATGTTGTAATCTT    880
TATAGGTTTCAATATAGCGGGTATACTTGGTGACATAAAGCGTTATGACATAAAGCGTTATGACATAAATAGAAGAAATGATAAATG  960
ATTATTAAATTCGTTATTAAAAATGTAAGAAGGAATAGTACAATATAGAACGTAAAAAAAATGCAAACCATTACTTC      1040
AATAAGAAAGGTTAGCAACCACTCAGCAAATGGGACACACATAGGATCCGACGTGGTTTATATTATAGTCTGATATT     1120
GTAGAGTCAATGGGTATATATTGCTCTTTTTTTCAAAGACTCCAGTTCCATTGAAGCGTAGGTTACTTCTTTAAACAAGACTCTG 1200
TTTTGAATGATATATTGTAAAGTTAAGGGGTACGTTTGTCTTTTTTCAGGACAAAGCGAGACCATAGATGACGTGTCAACTGC 1280
TAATTTTCAAAAACTCGGTCTACAAACCATAACCAAACTTATTATTCAATTATTCCGTCAAAAAATATAATTTTCTT     1360
TTTGCATCTCAATGGATTGATTCCATGCCAAGTGTTGGTGTTCATGAGAAAATTAGTCGCAGCTGATGACAACAAACA    1440
TCAAGCATTTATAATTTATATAACACTCACGAGTGCCTCTTTTCTTTATCTACCCTCGTCCTCCTAATCACAAACACACACAA 1520
ATCTCTGAAGTACCATGG                                                                 1537
         NcoI
                +1
```

SEED SPECIFIC PROMOTERS BASED ON ARABIDOPSIS GENES

BACKGROUND OF THE INVENTION

Promoter analysis of seed-specific genes has a rich history (reviewed in Goldberg et al. (1989) *Cell*, 56; 149–160; Thomas (1993) *Plant Cell*, 5; 1401–1410). This stems from the observation that no plant gene is more tightly regulated in terms of spatial expression than those encoding seed storage proteins. Many seed storage protein genes have been cloned from diverse plant species, and their promoters have been analyzed in detail (Thomas, 1993). In these experiments promoter elements, which constitute the 5'-upstream regulatory regions, were functionally defined by their ability to confer seed-specific expression of the bacterial β-glucuronidase (GUS) reporter gene in transgenic plants (Bogue et al. (1990) *Mol. Gen. Genet.*, 222; 49–57; Bustos et al. (1989) *Plant Cell*, 1; 839–853). Results of this work initiated efforts to functionally define cis-elements to these genes that are critical for conferring seed-specific expression.

Later experiments involved construction of deletion mutants consisting of target promoters fused to the GUS-reporter gene. Analysis of these constructs in transgenic plants allowed researchers to define regions within each promoter that are critical to its overall regulation (Bustos et al. (1991) *EMBO J.*, 10; 1469–1479; Chung (1995) *Ph.D. Dissertation*, Texas A&M University; Nunberg et al. (1994) *Plant Cell*, 6; 473–486). A general conclusion from this work is that the promoter proximal region contributes primarily to the gene's tissue specificity with more distal regions being responsible for modulating expression levels (Thomas, 1993). In addition to this, several groups have identified and characterized specific cis-regulatory elements, in both the promoter proximal region (PPR) and more distal regions, which interact with DNA binding proteins (Bustos et al., 1989; Chung, 1995; Jordano et al. (1989) *Plant Cell*, 1; 855–866; Nunberg et al., 1994). The functional significance of these regulatory elements varies from gene to gene.

In some cases, cis-regulatory elements have been mapped and the trans-acting factors which confer functionality have been cloned. For example, elements that allow the wheat EM-gene to respond to the plant hormone abscisic acid (ABA) have been defined. This work led to the identification of a DNA binding protein which mediates this response (Guiltinan et al. (1990) *Science*, 250; 267–271; Marcotte et al. (1989) *Plant Cell*, 1; 969–976). Putative ABA responsive elements have also been mapped in the sunflower helianthinin promoter HaG3-D and the carrot Dc3 promoter (Chung, 1995; Nunberg et al., 1994). Alone these elements act as positive elements in response to ABA. Regulation is restricted to the embryo, however, in the presence of each gene's promoter proximal region (Thomas, 1993).

Despite considerable effort, the cis-regulatory elements which contribute to a promoter's seed-specificity remain elusive (Chung, 1995; Li (1995) *Ph.D. Dissertation*, Texas A&M University). Recent work on the carrot Dc3 promoter proximal region has identified two bZIP genes that functionally interact with critical cis-elements (Kim et al. (1997) *Plant J.*, 11; 1237–1251). This.work has increased the understanding of seed-specific gene expression but it has also revealed that seed-specific gene regulation is complex.

In *Arabidopsis thaliana*, the promoters driving the expression of four members of the 2S albumin gene family have been analyzed in detail. The data indicate that each promoter is capable of conferring seed specific expression of a reporter gene in transgenic plants. Each promoter, however, confers slightly different spatial accumulation of the reporter in the developing seed. Thus, each family member contributes to the overall accumulation of the 2S albumins in the developing embryo. This is not unusual behavior for small gene families in plants (Lam et al. (1995) *Plant Cell*, 7; 887–898; Conceicao et al. (1994) *Plant J.*, 5; 493–505; Sj ödahl et al. (1993) *Plant Mol. Biol.*, 23; 1165–1176; Pang et al. (1988) *Plant Mol. Biol.*, 11; 805–820). In such cases, each member is capable of functionally complementing the others. The expression of each member is under different regulatory control leading to unique expression patterns. This appears to be a widespread gene regulatory mechanism in plants.

Little information is available on the contribution of a gene's untranslated elements to overall gene activity. In particular, the role of a gene's 5'-transcribed but untranslated region has never been fully investigated and is therefore not well understood. It is clear from the analysis of several plant genes, that these regions can significantly contribute to overall gene activity (Fu et al. (1995b) *Plant Cell*, 7; 1395–1403; Larkin et al. (1993) *Plant Cell*, 5; 1739–1748; Sieburth et al. (1997) *Plant Cell*, 9; 355–365). The general role of these regions, if any, is not known. This is mainly due to the observation that a gene's promoter, defined as the gene's 5'-untranscribed region which consists of 1.0–1.5 kb of 5'-upstream sequence, is necessary and sufficient to confer spatial and temporal expression of the GUS reporter gene in transgenic plants. It may or may not be sufficient to account for overall gene activity. A general comparison of these regions reveals little or no conservation between diverse genes, and a similar observation has been made with respect to promoter elements as well (Conceicao et al., 1994).

Despite the uncertainties associated with seed-specific regulatory elements, there is substantial interest in identification and isolation of such regulatory elements for use in manipulating expression of both native and heterologous genes in plant seeds. For example, well-defined seed specific regulatory elements are useful in manipulating fatty acid synthesis or lipid metabolism genes in plant seeds. Other important agronomic traits such as herbicide and pesticide resistance, and drought tolerance may also be altered in the plant seed by transforming plants with appropriate heterologous genes under the control of well-defined seed-specific promoters and cis regulatory elements.

The present invention provides regulatory elements including promoters and 5' untranslated regions from two seed-specific genes designated AtS1 and AtS3. The regulatory elements may be used with any native or heterologous gene or portion thereof for expression of a corresponding gene product in a plant seed.

SUMMARY OF THE INVENTION

The present invention is directed to 5' regulatory regions of two Arabidopsis seed-specific genes, AtS1 and AtS3.

In one embodiment this invention is directed to isolated nucleic acids comprising AtS1 5' regulatory regions which direct seed-specific expression including AtS1 promoters.

In another embodiment the present invention is directed to isolated nucleic acids comprising AtS3 regulatory regions which direct seed-specific expression including AtS3 promoters.

In a further embodiment the present invention is directed to vectors containing the isolated nucleic acids constituting the 5' regulatory regions of AtS1 and AtS3, respectively.

In still another embodiment, this invention is drawn to plants transformed with the vectors containing the isolated nucleic acids constituting the 5' regulatory regions of AtS1 and AtS3, respectively, including the progeny generated from such transformed plants.

In another embodiment, the present invention is drawn to a transgenic plant comprising the isolated nucleic acid which constitutes the 5' regulatory region of AtS1 and AtS3, respectively.

In still a further embodiment, this invention contemplates expression cassettes which comprise AtS1 5' regulatory regions including promoters operably linked to a heterologous gene or a nucleic acid encoding a sequence complementary to the native plant gene and vectors containing such expression cassettes.

In another embodiment, the present invention is directed to expression cassettes which comprise AtS3 5' regulatory regions including promoters operably linked to a heterologous gene or nucleic acid encoding a sequence complementary to the native plant gene and vectors containing such expression cassettes.

In one embodiment this invention contemplates a method for directing seed-specific expression in a plant by providing such plant with an isolated nucleic acid comprising an AtS1 or AtS3 5' regulatory region to effect such seed-specific expression.

BRIEF DESCRIPTION OF THE DRAWINGS

The file of this patent contains at least one drawing executed in color. Copies of this patent with color drawing (s) will be provided by the Patent and Trademark Office upon request and payment of the necessary fee.

FIG. 4A shows alignment of the 3'-termini for six different AtS1 cDNAs, 1-1 (SEQ ID NO:1), 1-2 (SEQ ID NO:2), 1-3 (SEQ ID NO:3), 1-4 (SEQ ID NO:4), 1-5 (SEQ ID NO:5), and 1-6 (SEQ ID NO:6). The location of the poly(A) tail on each cDNA is indicated by "An".

FIG. 4B shows alignment of the 3'-termini for six different AtS3 cDNAs, 3-1 (SEQ ID NO:7), 3-2 (SEQ ID NO:8), 3-3 (SEQ ID NO:9), 3-4 (SEQ ID NO:10), 3-5 (SEQ ID NO:11), and 3-6 (SEQ ID NO:12). The location of the poly(A) tail on each cDNA is indicated by "An".

FIG. 8 depicts the nucleotide sequence of a portion of a 5.5 kb genomic fragment containing the AtS1 gene (SEQ ID NO:13). The portion of the 5.5 kb fragment which aligns with the AtS1 cDNA and putative AtS1 protein (indicated in italics) is shown as well as sequence upstream from the translational start site and downstream from the translational stop. Two transcription start sites were mapped and are indicated by the double underline. The location of several polyadenylation sites are marked by the asterisks. The location of a putative CAAT box and TFID binding site are underlined.

FIG. 9 depicts the nucleotide sequence of a portion of a 7.9 kb genomic fragment containing the AtS3 gene (SEQ ID NO:14). The portion of the 7.9 kb fragment which aligns with the AtS3 cDNA and putative AtS3 protein (indicated in italics) is shown as well as sequence upstream from the translational start site and downstream from the translational stop. Four transcription start sites were mapped and are indicated by the double underline. The location of several polyadenylation sites are marked by the asterisks. The location of a putative CAAT box and TFID binding site are underlined.

FIG. 11A shows organization of the AtS1 genomic clone. The direction of transcription is indicated by the arrows and additional transcribed regions are also indicated. Exons are depicted by gray blocks, introns and non-coding sequences by lines, translational start sites by arrows and translational stop sites by a bar.

FIG. 11B shows organization of the AtS3 genomic clone. The direction of transcription is indicated by the arrows and additional transcribed regions are also indicated. Exons, introns and non-coding sequences are as depicted in FIG. 11A.

FIG. 15A shows the alignment of the AtS1 (SEQ ID NO:15) and EFA27 (SEQ ID NO:16) cDNAs using the FASTA algorithm.

FIG. 15B shows the alignment of the AtS1 (SEQ ID NO:17) and EFA27 (SEQ ID NO:18) gene products using the PIR algorithm (Huang et al. (1991) *Advances in Applied Mathematics*, 12; 337–357) Asterisks indicate identity.

FIG. 16A shows alignment of the AtS1 (SEQ ID NO:19) coding sequence with the sequence of the expressed sequence tag clone ATTS0251 (ATTS)(SEQ ID NO:20) using the FASTA algorithm.

FIG. 16B shows alignment of the EFA27 coding sequence (SEQ ID NO:21) with the sequence of the expressed sequence tag clone ATTS0251 (ATTS)(SEQ ID NO:22) using the FASTA algorithm.

FIG. 18A illustrates AtS1:GUS fusions. The construct denoted "tsp" represent transcriptional fusions; those denoted "tlp" represent translational fusions. The AtS1 genomic clone is pictured above the AtS1:GUS fusions to illustrate the elements included in each construct.

FIG. 18B illustrates AtS3:GUS fusions. Transcriptional and translational fusions are designated "tsp" and "tlp", respectively. The AtS3 genomic clone is pictured above the AtS3:GUS fusions to illustrate the elements included in each construct.

FIG. 23 shows the nucleotide sequence of the 1tsp promoter element. The promoter is derived from the AtS1 gene (genomic clone ddp5g in pBluescript as a SacI fragment). The promoter element was amplified by Pfu polymerase. The amplified promoter was cloned into the HindIII/BamHI sites in the vector pBI121 as a SacI/BamHI fragment. At the 5'-end the lower case sequence is what remains of the HindIII site and the SacI site (AtS1 promoter). The putative transcription site is indicated by a +1. Non-AtS1 spacer sequence is shown in italics; sequence to the right of the double underlined region is derived from the pBI121 polylinker (SEQ ID NO:39).

FIG. 24 shows the structure of the 1tlp promoter element. The promoter is derived from the AtS1 gene (genomic clone ddp5g in pBluescript as a SacI fragment). The promoter element was amplified by Pfu polymerase. It was initially cloned into the vector NCO-GUS as a PstI/NcoI fragment. The promoter: GUS fusion was moved into pBIN19 as a BAMHI/EcoRI fragment. The sequence shown is the promoter element itself as sequenced from the expression cassette. The BamHI site (5') and NcoI site (3') are in bold. The 5'-UTL is underlined, and the putative transcriptional start site is indicated by +1. The SacI site at the 5'-terminus is also underlined. This signifies the 5'-terminus of the AtS1 gene. The sequence preceding it is derived from the cloning vectors used to construct this expression cassette. The translation start site is double underlined. (SEQ ID NO:40).

FIG. 25 shows the structure of the 3tsp promoter element. The promoter is derived from the AtS3 gene (genomic clone ddp8g in pbluescript as a XbaI fragment). The promoter element was amplified by Pfu polymerase. It was initially cloned into the vector pBI101 as a XbaI/blunt fragment. The sequence shown is the promoter element itself as sequenced from the expression cassette. The 5' XbaI site is in bold. The presumed transcriptional start site is designated as +1. The underlined sequence represents non-AtS3 spacer sequence. This region includes a BamHI site (underlined and in bold); this site was originally engineered into the primer used to amplify the promoter element but was not used in the cloning procedure. Nucleotides 3' of this BamHI site are from the PBI101 polylinker region. (SEQ ID NO:41).

FIG. 26 shows the structure of the 3tlp promoter element. The promoter is derived from the AtS3 gene (genomic clone ddp8g in pBluescript as an XbaI fragment). The promoter element was amplified by Pfu polymerase. The amplified promoter was initially cloned into the vector NCO-GUS as an XbaI/NcoI fragment. The promoter::GUS fusion was moved into pBIN19 as an XbaI/EcoRI fragment. The sequence shown is the promoter element itself as sequenced from the expression cassette. The XbaI site (5') and NcoI sites (3') are in bold. The 5'-UTL is underlined. The translation start site is double-underlined. (SEQ ID NO:42).

DETAILED DESCRIPTION OF THE INVENTION

Figure 1A:
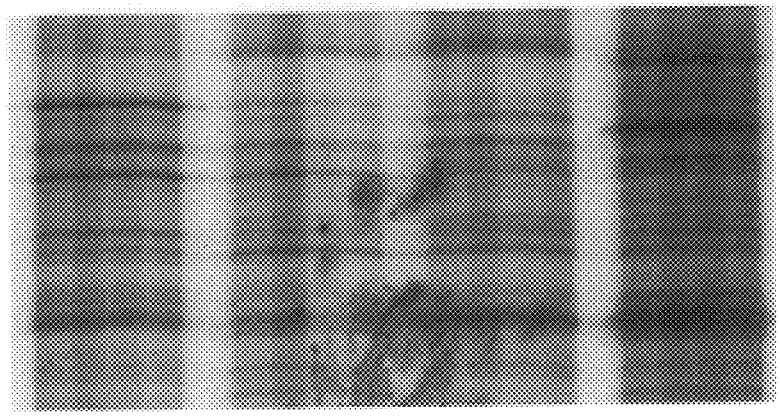
FIG. 1A depicts an autoradiograph of the reaction products from differential display PCR amplifications resolved on a 6% sequencing gel. The arrow indicates the AtS1 gene.

The present invention provides isolated nucleic acids encoding 5' regulatory regions from two Arabidopsis seed-specific genes, designated AtS1 and AtS3. In accordance with the present invention, the subject 5' regulatory regions, when operably linked to either a coding sequence of a heterologous gene or a sequence complementary to a native plant gene, direct expression of the coding sequence or complementary sequence in a plant seed. The AtS1 and AtS3 5' regulatory regions of the present invention are useful in the construction of expression cassettes which comprise in the 5' to 3' direction, a subject AtS1 or AtS3 5' regulatory region, a heterologous gene or sequence complementary to a native plant gene under control of the regulatory region and a 3' termination 1sequence. Such an expression cassette can be incorporated into a variety of autonomously replicating vectors in order to construct an expression vector.

As used herein, the term "regulatory region" can be further defined as comprising a promoter as well as 5' untranslated regions. The promoter of both the AtS1 and AtS3 gene is defined as the gene's 5' untranscribed region, generally consisting of 1.0 to 1.5 kb of 5' upstream sequence. The 5' transcribed but untranslated region, is located immediately downstream from the promoter and ends just prior to the translational start of the AtS1 or AtS3 gene.

As used herein, the term "cassette" refers to a nucleotide sequence capable of expressing a particular gene if said gene is inserted so as to be operably linked to one or more regulatory regions present in the nucleotide sequence. Thus, for example, the expression cassette may comprise a heterologous coding sequence which is desired to be expressed in a plant seed. The expression cassettes and expression vectors of the present invention are therefore useful for directing seed-specific expression of any number of heterologous genes. The term "seed-specific expression" as used herein, refers to expression in the embryo portion of a plant seed.

In one embodiment of the present invention, there is provided a promoter from an Arabidopsis AtS1 gene. In another embodiment of the invention, there is provided a promoter from an Arabidiosis AtS3 gene.

In another embodiment of the invention, there is provided a 5' transcribed and untranslated portion of an Arabidopsis AtS1 gene. In another embodiment of the invention, there is provided a 5' transcribed but untranslated portion of an Arabidopsis AtS3 gene.

In still another embodiment of the invention, there is provided a regulatory region comprising both a promoter and a 5' transcribed and untranslated region from an Arabidopsis AtS1 gene.

In yet another embodiment of the invention, there is provided a regulatory region comprising both a promoter and a 5' transcribed and untranslated region from an Arabidopsis AtS3 gene.

An isolated nucleic acid encoding a 5' regulatory region from an Arabidopsis AtS1 gene can be provided as follows. AtS1 recombinant genomic clones are first isolated by screening a plant genomic DNA library with a cDNA (or a portion thereof) representing AtS1 mRNA. An expressed sequence tag (EST) representing the AtS1 gene has been identified in an Arabidopsis dry seed library. The GeneBank accession numbers for the est clone (cDNA number pap232) are Z2053 and Z29900.

Methods considered useful in obtaining genomic recombinant DNA sequences corresponding to the AtS1 gene of the present by screening a genomic library are provided in Sambrook et al. (1989), *Molecular Cloning: A Laboratory Manual*, Cold Spring Harbor, N.Y., for example, or any of the myriad of laboratory manuals on recombinant DNA technology that are widely available.

An isolated nucleic acid encoding a 5' regulatory region from an Arabidopsis AtS1 or AtS3 gene can also be identified using an improved differential display method, described in detail herein. The differential display method is a PCR based technology which is designed to subdivide an mRNA population into reasonably comparable groups. This improved methodology permits matching the Tm(s) of the random primer (arbitrary 10-mer) and the oligo dT primers. Rather than using internal labeling to ensure the dT primer is included in the reaction and increasing the signal or noise the improved process permits labeling the oligo dT primers. In accordance with the present invention, instead of cloning candidate differential display products, the products were used as probes to screen full length cDNA libraries. PCR-based RNA fingerprinting is used to directly compare the expression of arbitrary genes from many tissues, allowing the identification of uniquely expressed genes.

The present invention also provides for an improved differential display gene isolation method than that of the prior art e.g., Liang et al. (1992) *Science*, 257; 967–971. The improved method employs accurate amplification, i.e., a mechanism to ensure that the oligonucleotide primers used for the analysis are functioning properly.

For example, by reducing the mRNA complexity, individual mRNAs may be accurately compared. This reduction is initially achieved by selectively priming cDNA synthesis with an anchored oligo-dT-primer. Although the primer needs to participate in both the cDNA synthesis and the PCR amplification step, the methods of the prior art do not effectively prime DNA synthesis since the annealing temperatures are too high. As a result, although the primer is designed to designate the mRNA population to be analyzed, differential display products having the primer are difficult to identify.

By lowering the annealing temperature as provided by the present invention, selecting for differential display products which contain the primer increase the likelihood that they in fact represent bona fide targets. Lowering the annealing temperature, however, also increases the background associated with differential display. Since the arbitrary 10-mer is more efficient in the PCR amplification step, reaction products containing just the primer will likely be very abundant and are therefore removed.

Stringent selection is also an important element in the improved differential display process of the present invention. A stringent mechanism to remove the background hybridization is required to avoid screening through each cDNA clone individually. For example, a differential display band likely represents more than one DNA template and the signal sequence needs to be purified away from the background sequences. In isolating an AtS1 or AtS3 gene, the cDNA library represents poly(A)-enriched RNA made from mRNAs isolated from seeds. Screening the library under high stringency conditions should select against background sequences including cDNAs generated from tRNA or rRNA templates.

Exemplification of the differential display analysis in isolating AtS1 and AtS3 seed-specific genes is given in Example 1.

To determine nucleotide sequences, a multitude of techniques are available and known to the ordinarily skilled artisan. For example, restriction fragments containing a corresponding AtS1 or AtS3 regulatory region can be subcloned into the polylinker site of a sequencing vector such as pBluescript (Stratagene). These pBluescript subclones can then be sequenced by the double-stranded dideoxy method (Chen et al. (1985) *DNA*, 4; 165).

In a preferred embodiment of the present invention, the AtS1 promoter comprises nucleotides 6-1211 of FIG. 23 (SEQ ID NO:23). The AtS3 promoter preferably comprises nucleotides 7-1486 of FIG. 25 (SEQ ID NO:24). In another preferred embodiment, the AtS1 5' transcribed and untranslated region comprises nucleotides 1326 to 1387 of FIG. 24 (SEQ ID NO:25). In yet another preferred embodiment, the AtS3 5' transcribed and untranslated region comprises nucleotides 1472 to 1537 of FIG. 26 (SEQ ID NO:26).

In a more preferred embodiment, the AtS1 regulatory region is made up of both the promoter and 5' transcribed and untranslated region and comprises nucleotides 42 to 1387 of FIG. 24 (SEQ ID NO:27). In another more preferred embodiment, the AtS3 regulatory region is made up of both the promoter and 5' transcribed but untranslated region and comprises nucleotides 7 to 1537 of FIG. 26 (SEQ ID NO:28).

Modifications to the AtS1 and AtS3 regulatory regions, including the individual promoters and 5' transcribed but untranslated regions as set forth in SEQ ID NOS:23 through 28, which maintain the characteristic property of directing seed-specific expression, are within the scope of the present invention. Such modifications include insertions, deletions and substitutions of one or more nucleotides.

The subject AtS1 and AtS3 5' regulatory regions and parts thereof such as promoters and 5' transcribed but untranslated regions, can be derived from restriction endonuclease or exonuclease digestion of isolated AtS1 or AtS3 genomic clones. Thus, for example, the known nucleotide or amino acid sequence of the coding region of an isolated AtS1 or AtS3 gene (e.g. FIGS. 8 and 9) is aligned to the nucleic acid or deduced amino acid sequence of an isolated seed-specific genomic clone and the 5' flanking sequence (i.e., sequence upstream from the translational start codon of the coding region) of the isolated AtS1 and AtS3 genomic clone located.

The AtS1 and AtS3 5' regulatory regions as set forth in SEQ ID NOs: 27 and 28 respectively, (nucleotides 42 to 1387 of FIG. 24 and nucleotides 7-1537 of FIG. 26, respectively ) may be generated from genomic clones having either or both excess 5' flanking sequence or coding sequence by exonuclease III-mediated deletion. This is accomplished by digesting appropriately prepared DNA with exonuclease III (exoIII) and removing aliquots at increasing intervals of time during the digestion. The resulting successively smaller fragments of DNA may be sequenced to determine the exact endpoint of the deletions. There are several commercially available systems which use exonuclease III (exoIII) to create such a deletion series, e.g. Promega Biotech, "Erase-A-Base" system. Alternatively, PCR primers can be defined to allow direct amplification of the subject AtS1 or AtS3 regulatory regions, or parts thereof such as promoters and 5' transcribed but untranslated regions.

Using the same methodologies, the ordinarily skilled artisan can generate one or more deletion fragments of the regulatory regions of the AtS1 and AtS3 genes as set forth in SEQ ID NOs: 27 and 28 respectively. Any and all deletion fragments which comprise a contiguous portion of the nucleotide sequences set forth in any of SEQ ID NOS:23, 24, 25, 26, 27, or 28 and which retain the capacity to direct seed-specific expression are contemplated by the present invention.

Confirmation of seed-specific 5' regulatory regions which direct seed-specific expression and modifications or deletion fragments thereof, can be accomplished by construction of transcriptional and/or translational fusions of specific sequences with the coding sequences of a heterologous gene, transfer of the chimeric gene into an appropriate host, and detection of the expression of the heterologous gene. The assay used to detect expression depends upon the nature of the heterologous sequence. For example, reporter genes, exemplified by chloramphenicol acetyl transferase and β-glucuronidase (GUS), are commonly used to assess transcriptional and translational competence of chimeric constructions. Standard assays are available to sensitively detect the reporter enzyme in a transgenic organism. The β-glucuronidase (GUS) gene is useful as a reporter of promoter activity in transgenic plants because of the high stability of the enzyme in plant cells, the lack of intrinsic β-glucuronidase activity in higher plants and availability of a quantitative fluorimetric assay and a histochemical localization technique. Jefferson et al. (1987b) *EMBO J* 6; 3901–3907 have established standard procedures for biochemical and histochemical detection of GUS activity in plant tissues. Biochemical assays are performed by mixing plant tissue lysates with 4-methylumbelliferyl-β-D-glucuronide, a fluorimetric substrate for GUS, incubating one hour at 37° C., and then measuring the fluorescence of the resulting 4-methyl-umbelliferone. Histochemical localization for GUS activity is determined by incubating plant tissue samples in 5-bromo-4-chloro-3-indolyl-glucuronide (X-Gluc) for about 18 hours at 37° C. and observing the staining pattern of X-Gluc. The construction of such chimeric genes allows definition of specific regulatory sequences and demonstrates that these sequences can direct expression of heterologous genes in a seed-specific manner.

Another aspect of the invention is directed to expression cassettes and expression vectors (also termed herein "chimeric genes") comprising a 5' regulatory region or portion thereof from an AtS1 or AtS3 gene which direct seed specific expression operably linked to the coding sequence of a heterologous gene such that the regulatory element is capable of controlling expression of the product encoded by the heterologous gene. The heterologous gene can be any gene other than AtS1 or AtS3. If necessary, additional regulatory elements from genes other than AtS1 or AtS3 or parts of such elements sufficient to cause expression resulting in production of an effective amount of the polypeptide encoded by the heterologous gene are included in the chimeric constructs.

Accordingly, the present invention provides chimeric genes comprising sequences of the AtS1 or AtS3 5' regulatory region that confer seed-specific expression which are operably linked to a sequence encoding a heterologous gene such as a lipid metabolism enzyme. Examples of lipid metabolism genes useful for practicing the present invention include lipid desaturases such as Δ6-desaturases, Δ12-desaturases, Δ15-desaturases and other related desaturases such as stearoyl-ACP desaturases, acyl carrier proteins (ACPs), thioesterases, acetyl transacylases, acetyl-coA carboxylases, ketoacyl-synthases, malonyl transacylases, and elongases. Such lipid metabolism genes have been isolated and characterized from a number of different bacteria and plant species. Their nucleotide coding sequences as well as methods of isolating such coding sequences are disclosed in the published literature and are widely available to those of skill in the art.

In particular, the Δ6-desaturase genes disclosed in U.S. Pat. Nos. 5,552,306 and 5,614,393 and incorporated herein by reference, are contemplated as lipid metabolism genes particularly useful in the practice of the present invention.

The chimeric genes of the present invention are constructed by ligating a 5' regulatory region or part thereof, of an AtS1 or AtS3 genomic DNA to the coding sequence of a heterologous gene. The juxtaposition of these sequences can be accomplished in a variety of ways. In one embodiment, the order of sequences in a 5' to 3' direction, is an AtS1 or AtS3 promoter, a coding sequence, and a termination sequence. In a preferred embodiment, the order of the sequences in a 5' to 3' direction is an AtS1 or AtS3 promoter, an AtS1 or AtS3 transcribed but untranslated region, a coding sequence, and a termination sequence which includes a polyadenylation site.

Standard techniques for construction of such chimeric genes are well known to those of ordinary skill in the art and can be found in references such as Sambrook et al. (1989). A variety of strategies are available for ligating fragments of DNA, the choice of which depends on the nature of the termini of the DNA fragments. One of ordinary skill in the art recognizes that in order for the heterologous gene to be expressed, the construction requires at least a promoter and signal for efficient polyadenylation of the transcript. Accordingly, the AtS1 or AtS3 5' regulatory region that contains the consensus promoter sequence known as the TATA box can be ligated directly to a promoterless heterologous coding sequence.

The restriction or deletion fragments that contain the AtS1 or AtS3 TATA box are ligated in a forward orientation to a promoterless heterologous gene such as the coding sequence of β-glucuronidase (GUS). The skilled artisan will recognize that the subject AtS1 or AtS3 5' regulatory regions and parts thereof, can be provided by other means, for example chemical or enzymatic synthesis.

The 3' end of a heterologous coding sequence is optionally ligated to a termination sequence comprising a polyadenylation site, exemplified by, but not limited to, the nopaline synthase polyadenylation site, or the octopine T-DNA gene 7 polyadenylation site. Alternatively, the polyadenylation site can be provided by the heterologous gene.

The present invention also provides methods of increasing levels of heterologous genes in plant seeds. In accordance with such methods, the subject expression cassettes and expression vectors are introduced into a plant in order to effect expression of a heterologous gene. For example, a method of producing a plant with increased levels of a product of a fatty acid synthesis or lipid metabolism gene is provided by transforming a plant cell with an expression vector comprising an AtS1 or AtS3 5' regulatory region or portion thereof, operably linked to a fatty acid synthesis or lipid metabolism gene and regenerating a plant with increased levels of the product of said fatty acid synthesis or lipid metabolism gene.

Another aspect of the present invention provides methods of reducing levels of a product of a gene which is native to a plant which comprises transforming a plant cell with an expression vector comprising a subject AtS1 or AtS2 5' regulatory region or part thereof, operably linked to a nucleic acid sequence which is complementary to the native plant gene. In this manner, levels of endogenous product of the native plant gene are reduced through the mechanism known as antisense regulation. Thus, for example, levels of a product of a fatty acid synthesis gene or lipid metabolism gene are reduced by transforming a plant with an expression vector comprising a subject AtS1 or AtS3 5' regulatory region or part thereof, operably linked to a nucleic acid sequence which is complementary to a nucleic acid sequence coding for a native fatty acid synthesis or lipid metabolism gene.

The present invention also provides a method of cosuppressing a gene which is native to a plant which comprises transforming a plant cell with an expression vector comprising a subject 5' AtS1 or AtS3 regulatory region operably linked to a nucleic acid sequence coding for the native plant gene. In this manner, levels of endogenous product of the native plant gene are reduced through the mechanism known as cosuppression. Thus, for example, levels of a product of a fatty acid synthesis gene or lipid metabolism gene are reduced by transforming a plant with an expression vector comprising a subject AtS1 or AtS3 5' regulatory region or part thereof, operably linked to a nucleic acid sequence coding for a native fatty acid synthesis or lipid metabolism gene native to the plant. Although the exact mechanism of cosuppression is not completely understood, one skilled in the art is familiar with published works reporting the experimental conditions and results associated with cosuppression (Napoli et al. (1990) *The Plant Cell*, 2; 270–289; Van der Krol (1990) *Plant Mol. Biol*, 14; 457–466.)

To provide regulated expression of the heterologous or native genes, plants are transformed with the chimeric gene constructions of the invention. Methods of gene transfer are well known in the art. The chimeric genes can be introduced into plants by leaf disk transformation-regeneration procedure as described by Horsch et al. (1985) *Science*, 227; 1229–1231. Other methods of transformation such as protoplast culture (Horsch et al. (1984) *Science*, 223; 496; DeBlock et al. (1984) *EMBO J.*, 2; 2143; Barton et al. (1983) *Cell*, 32; 1033) can also be used and are within the scope of this invention. In a preferred embodiment, plants are transformed with Agrobacterium-derived vectors such as those described in Klett et al. (1987) *Annu. Rev. Plant Physiol.*, 38; 467. Other well-known methods are available to insert the chimeric genes of the present invention into plant cells. Such alternative methods include biolistic approaches (Klein et al. (1987) *Nature*, 327; 70), electroporation, chemically-induced DNA uptake, and use of viruses or pollen as vectors.

When necessary for the transformation method, the chimeric genes of the present invention can be inserted into a plant transformation vector, e.g. the binary vector described by Bevan (1984) *Nucleic Acids Res.*, 12; 8711–8721. Plant transformation vectors can be derived by modifying the natural gene transfer system of *Agrobacterium tumefaciens*. The natural system comprises large Ti (tumor-inducing)-plasmids containing a large segment, known as T-DNA, which is transferred to transformed plants. Another segment of the Ti plasmid, the vir region, is responsible for T-DNA transfer. The T-DNA region is bordered by terminal repeats. In the modified binary vectors, the tumor inducing genes have been deleted and the functions of the vir region are utilized to transfer foreign DNA bordered by the T-DNA border sequences. The T-region also contains a selectable marker for antibiotic resistance, and a multiple cloning site for inserting sequences for transfer. Such engineered strains are known as "disarmed" *A. tumefaciens* strains, and allow the efficient transfer of sequences bordered by the T-region into the nuclear genome of plants.

Surface-sterilized leaf disks and other susceptible tissues are inoculated with the "disarmed" foreign DNA-containing *A. tumefaciens*, cultured for a number of days, and then transferred to antibiotic-containing medium. Transformed shoots are then selected after rooting in medium containing the appropriate antibiotic, and transferred to soil. Transgenic plants are pollinated and seeds from these plants are collected and grown on antibiotic medium.

Expression of a heterologous or reporter gene in developing seeds, young seedlings and mature plants can be monitored by immunological, histochemical or activity assays. As discussed herein, the choice of an assay for expression of the chimeric gene depends upon the nature of the heterologous coding region. For example, Northern analysis can be used to assess transcription if appropriate nucleotide probes are available. If antibodies to the polypeptide encoded by the heterologous gene are available, Western analysis and immunohistochemical localization can be used to assess the production and localization of the polypeptide. Depending upon the heterologous gene, appropriate biochemical assays can be used. For example, acetyltransferases are detected by measuring acetylation of a standard substrate. The expression of a lipid desaturase gene can be assayed by analysis of fatty acid methyl esters (FAMES).

Another aspect of the present invention provides transgenic plants or progeny of these plants containing the chimeric genes of the invention. Both monocotyledonous and dicotyledonous plants are contemplated. Plant cells are transformed with the chimeric genes by any of the plant transformation methods described above. The transformed plant cell, usually in the form of a callus culture, leaf disk, explant or whole plant (via the vacuum infiltration method of Bechtold et al. (1993) *C.R. Acad. Sci. Paris*, 316; 1194–1199) is regenerated into a complete transgenic plant by methods well-known to one of ordinary skill in the art (e.g., Horsh et al., 1985). In a preferred embodiment, the transgenic plant is sunflower, cotton, oil seed rape, maize, tobacco, Arabidopsis, peanut or soybean. Since progeny of transformed plants inherit the chimeric genes, seeds or cuttings from transformed plants are used to maintain the transgenic line.

The following examples further illustrate the invention.

EXAMPLE 1

IDENTIFICATION OF ATS1 AND ATS3 AS SEED-SPECIFIC GENES

Both ATS1 and AtS3 were identified as seed-specific genes in Arabidopsis by differential display. The differential display method is a PCR based technology which is designed to subdivide an mRNA population into reasonably comparable groups. PCR-based RNA fingerprinting is used to directly compare the expression of arbitrary genes from many tissues, allowing the identification of uniquely expressed genes. (McClelland et al. (1995) *Trends Genet.*, 11; 242–246; Nuccio et al. (1996) SAAS Bulletin, *Biochem. & Biotech.*, 9; 23–28; Frugoli et al. (1996) *Heynh. Plant Physiol.*, 112; 327–336; Vielle-Calzada et al. (1996) *Link. Plant Mol. Biol.*, 32; 1085–1092).

Plant Maintenance and Tissue Preparation

*Arabidopsis thaliana* (Landsberg) plants were grown under continuous illumination in a vermiculite/soil mixture at ambient temperature (22° C.). Siliques were dissected 2 to 5 days after flowering to separate immature seeds from the silique coats. Both tissues were frozen in liquid nitrogen and stored at −85° C. Root tissue was obtained from elongated roots grown in liquid culture. The root cultures were started from 4 to 20 seeds which were surface sterilized with 10% bleach/0.1% SDS, rinsed thoroughly with water, and cultured in Gamborg $B_5$ medium for two weeks. Inflorescences containing initial flower buds and fully opened flowers, and leaves of different sizes were also collected.

RNA Preparation

Total RNA was prepared following a procedure that has been modified from Galau et al. (1981) *J. Biol. Chem.*, 256; 2551–2560 and Crouch et al. (1983) *J. Mol. Appl. Genet.*, 2; 273–283. Briefly, at 0–4° C., tissue was ground to powder in liquid nitrogen and the powder was resuspended in homogenization buffer (0.1 M Tris-HCL (pH 9.0), 0.1 M NaCL, 1 mM EDTA (pH 8.0), 0.5% SDS) at 20 mL buffer per gram of tissue (v/w). This was done at 0–4° C. One-half volume of hot phenol, which had been previously equilibrated with homogenization buffer was then added and the mixture was homogenized using a Brinkman polytron at high speed for one minute. One-half volume of SEVAG was then added and the mixture was homogenized as before. The aqueous phase was separated by centrifugation at 8000×g for 10 minutes and removed. The phenol/SEVAG extraction was repeated and the aqueous phase was removed. Nucleic acids were precipitated in 0.2 M potassium acetate (pH 6.0) and 2.5 volumes ETOH overnight at −20° C. The homogenate was ethanol precipitated once more followed by lithium chloride and potassium acetate precipitations before a final ethanol precipitation. The RNA was stored as an ethanol precipitate at −90° C. until use. Before using the RNA in enzymatic reactions, the precipitate was washed in cold 70% ethanol followed by a cold 95% ethanol wash and resuspended in TE buffer.

Differential Display Analysis

Differential display analysis was routinely carried out using 1 μg total RNA per sample as starting material. cDNA synthesis was carried out as described previously (Liang et al., 1992; Liang et al. (1993) *Nucl. Acids Res.*, 21; 3269–3275). The first-strand cDNA template was synthesized using reagents from the GIBCO-BRL cDNA synthesis kit (Cat. #18267-013). Total RNA was incubated in 22.5 $\mu$l containing 5 $\mu$l 5× reaction buffer (250 mM Tris-HCl (pH 8.3), 375 mM KCl, 15 mM $MgCl_2$), 2.5 $\mu$l 200 $\mu$M dNTPs, and 2.5 $\mu$l 25 $\mu$M $T_{11}$VN primer (where V=dATP, dCTP, or dGTP and N=dATP, dCTP, dGTP or dTTP) for 3 minutes at 65° C., then allowed to cool for 3 minutes at room temperature. This was repeated twice more. Dithiothreitol was added to a final concentration of 5 mM and 250 Units of MMLV reverse transcriptase were added and the cDNA synthesis reaction was carried out at 37° C. for 1 hour. The reaction was terminated by heating to 95° C. for 5 minutes. This represents the CDNA template used for the differential display PCR reaction and was stored at −20° C. until use.

The PCR reaction also followed earlier protocols (Liang et al., 1992; Liang et al., 1993), but the reaction components varied depending on the radioactive probe used to identify the reaction products. When $^{32}$P-dATP was used, the final dNTP concentration was 2 $\mu$M. When a $^{32}$P-labeled primer was used, the final dNTP concentration was 200 $\mu$M except where it is otherwise indicated. The $T_{11}$VN primer or the arbitrary 10-mer were end-labeled as follows: 3.125 nmole primer was incubated with 125 pmole $^{32}$P-γ-ATP in a kinase reaction described in Ausubel et al. (1994) *Current Protocols in Molecular Biology*, New York: John Wiley and Sons. The labeled primer was precipitated with one half volume of 7.5M ammonium acetate and 2.5 volumes 100% ethanol using 50 $\mu$g glycogen as carrier at −85° C. for 1 hour. The pellet was washed briefly with 95% ethanol, dried and resuspended in 50 $\mu$l TE buffer.

The PCR reactions were set up as follows: 2 $\mu$l cDNA template (representing 40 ng of the original total RNA) and 2.5 pM $T_{11}$VN primer (the same primer used to prime first strand cDNA synthesis) were added to a reaction mix containing 0.5 $\mu$M arbitrary 10-mer, 50 mM KCl, 10 mM Tris-HCl (pH 9.0 at 25° C.), 0.1% Triton X-100, 4.8 mM $MgCl_2$, either 2 $\mu$M or 200 $\mu$M of each dNTP, and 5 Units of Taq polymerase (Promega, Madison, Wis.) in a final volume of 25 $\mu$l. The reaction mix was overlayed with, mineral oil and heated to 95° C. for 5 minutes followed by a thermocycle program of 95° C. for 30 seconds, either 42° C. or 35° C. for 1 minute, 72° C. for 30 seconds and cycled 40 times. This was followed by a 5 minute extension period at 72° C. The reaction products were resolved by adding 3 $\mu$l sequencing reaction stop buffer (Epicenter Technologies) to 6 $\mu$l of reaction mix and resolved on a 6% sequencing gel at 50 mAmps. The gel was dried and autoradiographed.

Differential display bands were excised as described previously (Liang et al., 1992). The gel slice was placed in a dialysis bag containing 300 $\mu$l 1× TBE buffer and electroeluted as described in Ausubel et al. (1994). The eluent was collected, and the DNA was precipitated as described above. The pellet was washed briefly in 95% ethanol, dried and resuspended in 10 $\mu$l TE buffer. DNA representing the differential display band was regenerated using 4 $\mu$l of the isolated DNA in a reaction similar to the differential display PCR reaction except that 2.5 $\mu$M unlabeled $T_{11}$VN primer was used. A 1 $\mu$l aliquot was resolved in a 1% agarose gel which was photographed, dried and autoradiographed. A successful regeneration was characterized by the appropriately sized band which demonstrated radioactivity above background. The remaining reaction products were resolved on a 1% agarose gel and the DNA representing the regenerated band was excised and isolated from the agarose by centrifugation through a 45 $\mu$M microspin filter as described by the manufacturer (Millipore). The DNA was precipitated and dissolved in a final volume of 20 $\mu$l TE. This DNA represents the template used to generate the differential display probes.

Synthesis of Differential Display Probes

The regenerated differential display band was used as template to generate the differential display probe. The probe was synthesized in the following PCR reaction: 2 $\mu$l of regenerated DNA was combined in a reaction mix containing 2.5 $\mu$M $T_{11}$VN primer; 0.5 $\mu$M arbitrary 10-mer; 50 mM KCl; 10 mM Tris-HCl (pH 9.0 at 26° C.); 0.1% Triton X-100; 4.8 mM $MgCl_2$; 207 $\mu$M dCTP, dGTP, and dTTP; 7 $\mu$M dATP; 50 $\mu$Ci $^{32}$P-dATP (3000 Ci/mmol), and 5 Units of Taq polymerase (Promega, Madison, Wis.), in a final volume of 30 $\mu$l. The reaction mixture was overlayed with mineral oil and subjected to a thermocycling program identical to that described for the differential display PCR reaction. Unincorporated reaction products were removed by centrifugation through a G-50 spin column (Boehringer Mannheim, Indianapolis, Ind.). The $^{32}$P-incorporation was measured by scintillation counting and the probe was used at a final concentration of at least 1×10$^6$ cpm/ml.

Plaque Hybridization

An *Arabidopsis thaliana* var. Landsberg erecta cDNA library representing immature seeds was constructed following the method of Nuccio et al. (1996). The library was plated on XL1-Blue MRF' cells at a density of 50,000 PFU per plate (150 mM) containing LB media. Plaques were transferred to nitrocellulose membranes as recommended by the manufacturer and hybridized by standard methods (Ausubel et al., 1994). After 4 hours prehybridization in hybridization II buffer (1% crystalline BSA, 1 mM EDTA, 0.5 M $NaHPO_4$, pH 7.2, 7% SDS) at 65° C., the differential display probe, which had been boiled in 50% formamide for 3 minutes, was added to the same hybridization solution. Hybridization was continued up to 24 hours at 65° C. The filters were washed twice in 0.5% crystalline BSA, 1 mM EDTA, 40 mM $NaHPO_4$, pH 7.2, 5% SDS for 5 minutes each at room temperature, and then three times in 1 mM EDTA, 40 mM $NaHPO_4$, pH 7.2, 1% SDS for 10 minutes each at 65° C. Autoradiographs were exposed for 1 day at −85° C.

RNA Gel Blot Analysis

10 $\mu$g of total RNA from flower, leaf, root, immature seed, and silique without seed were resuspended in 10 $\mu$l loading buffer (48% formamide, 1× MOPS buffer 0.02 M 3-[N-morpholino] propane sulfonic acid, 1 mM EDTA, 5 mM sodium acetate at pH 6.0), 17% formalin, 0.7 mg/ml ethidium bromide, 5.3% glycerol, 5.3% saturated bromophenol blue) and resolved on a 1.2% agarose gel containing 7% formaldehyde in 1× MOPS buffer. RNA was transferred to a nylon filter (Micron Separations Incorporated) in 10× SSC. Blots were hybridized with probes prepared from gel purified cDNA inserts in 50% deionized formamide, 5× SSPE, 1× Dendhardt's solution, 0.1% SDS, and 100 $\mu$g denatured salmon sperm DNA at 42° C. for 24 hours. Radioactive probes were prepared from cDNA templates by the random primer method (Feinberg et al. (1983) *Alan. Biochem.*, 132; 6–13) and each had a specific activity greater than 1×10$^9$ cpm/$\mu$g. Filters were washed first in 0.6 M NaCl, 0.08 M Tris-HCl, 4 mM EDTA, 12.5 mM phosphate buffer, pH 6.8 and 0.2% SDS at 60° C. for 15 minutes, followed by 0.3 M NaCl, 0.04 M Tris-HCL, 2 mM EDTA, 12.5 mM phoisphate buffer, pH 6.8, and 0.2% SDS at 60° C. for 15 minutes, and then 0.15 M NaCl 0.02 M Tris-HCl, 1 mM EDTA, 12.5 mM phosphate buffer, pH 6.8 and 0.2% SDS at 60° C. for 10 minutes. The filters were wrapped in Saran Wrap and autoradiographed.

Sequence Analysis

Mini-prep plasmid DNA was used as templates in cycle sequencing reactions with the SequiTherm cycle sequencing kit (Epicenter Technologies, Madison, Wis.). Sequence analysis was done locally with GCG (Devereux et al. (1984) *Nucl. Acids Res.*, 12; 387–395) on a DEC Micro VAXII; database searches were done remotely through NCBI using the BLAST algorithm (Altschul et al. (1990) *J. Mol. Biol.*, 215; 403–410). cDNAs representing previously characterized Arabidopsis genes were discarded.

EXAMPLE 2

CHARACTERIZATION OF ATS1 AND ATS3 BY DEVELOPMENTAL RNA GEL BLOT ANALYSIS

RNA Gel Blot Analysis

Figure 1B:
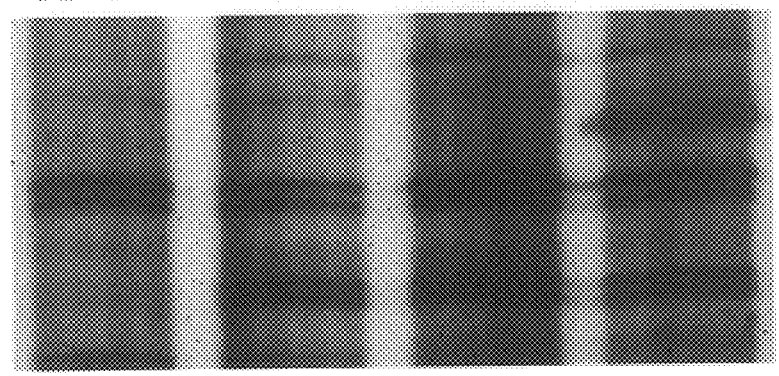
FIG. 1B depicts an autoradiograph of the reaction products from differential display PCR amplifications resolved on a 6% sequencing gel. The arrow indicates the AtS3 gene.

A total of ten groups of putative seed specific cDNAs were identified in the cDNA library screen (Table 1). Only three of these were verified to be seed-specific by RNA gel blot analysis. The differential display gels identifying AtS1 and AtS3 are depicted in FIGS. 1A and 1B, respectively. The cDNA designated AtS2 is a confirmed seed-specific cDNA, and the initial sequence analysis indicated that it was novel. Further sequencing, however, revealed that it was chimeric and contained a fragment of 12S seed storage protein sequence. Subsequent RNA gel blot analysis indicated that the 12S component of this clone was responsible for the seed-specific signal. Thus, it was discarded.

The cDNAs isolated by differential display analysis in Example 1 were then subjected to expression analysis by RNA gel blot hybridization. This step was performed in order to confirm results from the differential display analysis.

*Arabidopsis thaliana* (Landsberg) growth conditions and tissue preparation were as described in Example 1. RNA was also prepared as described in Example 1. Tissue representing globular-heart (1–3 day post flowering), heart to torpedo (3–5 day post flowering), torpedo to early cotyledon (5–7 day post flowering), early cotyledon to late cotyledon (7–13 day post flowering) stage siliques was collected and stored at −90° C. Dry seeds, floral and leaf tissue were also collected. Ten micrograms of total RNA were resuspended in 10 μl loading buffer (48% formamide, 1× MOPS buffer 0.02 M 3-[N-morpholino] propane sulfonic acid, 1 mM EDTA, 5 mM sodium acetate at pH 6.0), 17% formalin, 0.7 mg/ml ethidium bromide, 5.3% glycerol, 5.3% saturated bromophenol blue) and resolved on a 1.2% agarose gel containing 7% formaldehyde in 1× MOPS buffer. RNA was transferred to a nylon filter (Micron Separations Incorporated, Westboro Mass.) in 1× SSC. Blots were hybridized with probes prepared from gel purified cDNA inserts in 50% deionized formamide, 5× SSPE, 1× Denhardt's solution, 0.1% SDS, and 100 μg denatured salmon sperm DNA at 42° C. for 24 hours.

Radioactive probes were prepared from cDNA templates representing both the AtS1 and AtS3 genes, a tubulin gene (Marks et al. (1987) *Plant Mol. Biol.*, 10; 91–104), the 12S cruciferin gene and the 2S albumin gene (Guerche et al. (1990) *Plant Cell.*, 2; 469–478; Pang et al, 1988) by the random priming method (Feinberg et al., 1983) and each had a specific activity of greater than $1 \times 10^9$ cpm/ug. Filters were washed first in 0.6M NaCl, 0.08 M Tris-HCl, 4 mM EDTA, 12.5 mM phosphate buffer, pH 6.8, and 0.2% SDS at 60° C. for 15 minutes, and then 0.3 M NaCl, 0.04 M Tris-HCl, 2 mM EDTA, 12.5 mM phosphate buffer, pH 6.8, and 0.2% SDS at 60° C. for 15 minutes, followed by 0.15 M NaCl, 0.02 M Tris-HCl, 1 mM EDTA, 12.5 mM phosphate buffer, pH 6.8, and 0.2% SDS at 60° C. for 10 minutes. Hybridization signals were recorded with a Fujix BAS 2000 phosphoimager. The data were analyzed using MacBAS (ver. 2.1) software. The hybridization signal was quantitated and adjusted for probe specific activity and length. The hybridization signal for each sample was also adjusted for loading by virtue of hybridization to a tubulin cDNA probe (Marks et al., 1987). In this manner, both the quantitative and temporal accumulation of the AtS1 and AtS3 genes were determined and compared to that of well characterized seed-specific genes.

Figure 2:
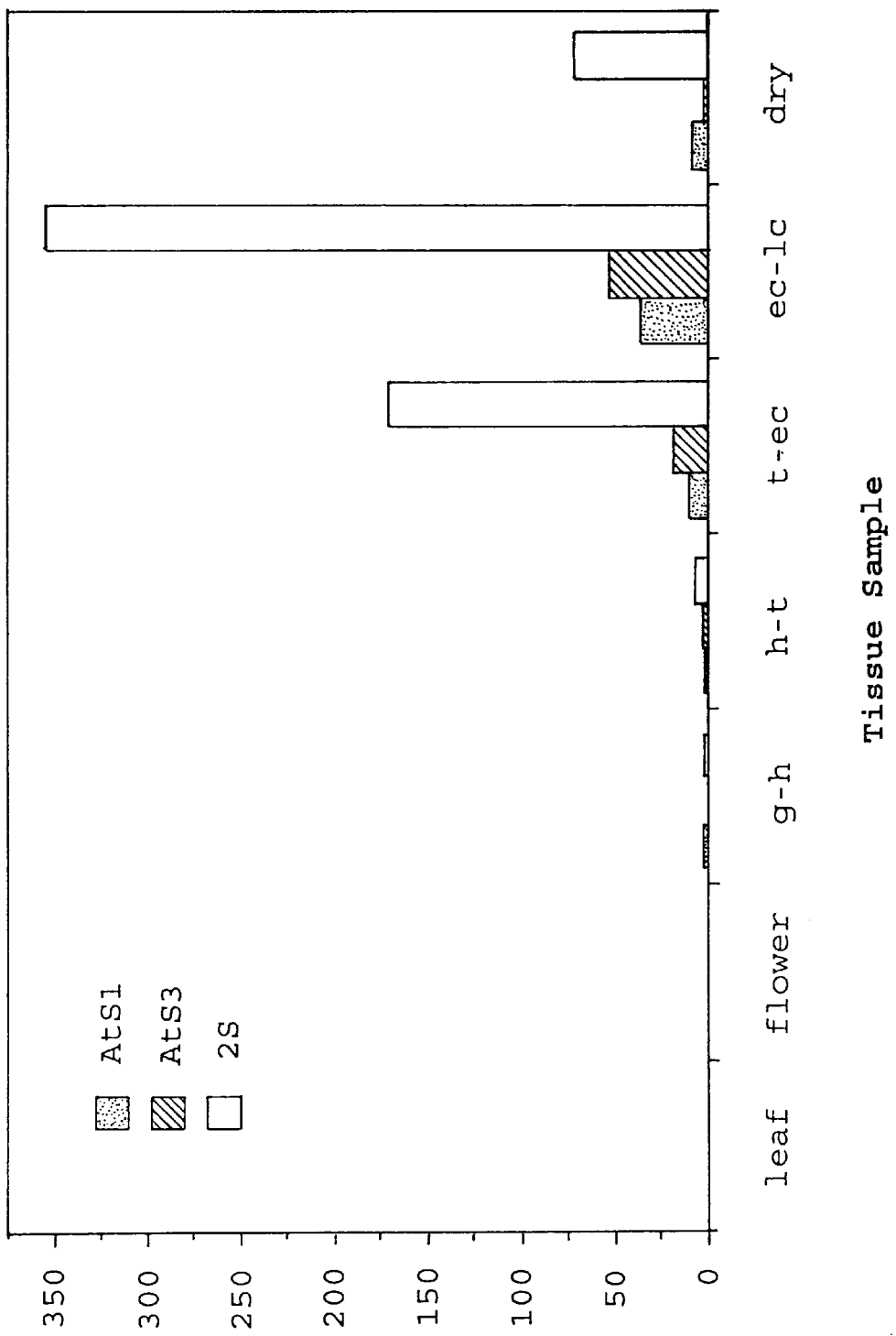
FIG. 2 is a graph depicting developmental expression of three seed-specific Arabidopsis genes, AtS1, AtS3, and 2S. Abbreviations are as follows: g-h, globular to heart stage siliques; h-t, heart to torpedo stage siliques; t-ec: torpedo to early cotyledon stage siliques; ec-lc, early cotyledon to late cotyledon stage siliques; dry, dry seed.

As shown in FIG. 2 and Table 2, both AtS1 and AtS3 are expressed at the junction between heart and torpedo stage, and this expression continues to high levels as the seed matures. The expression is down regulated during desiccation. The mRNAs transcribed from both genes appear to be stable in the dry seed which suggests a possible role early in germination. Although the expression pattern resembles that of the 12S and 2S seed storage protein genes, neither AtS1 nor AtS3 are expressed to the same level.

Figure 3A:
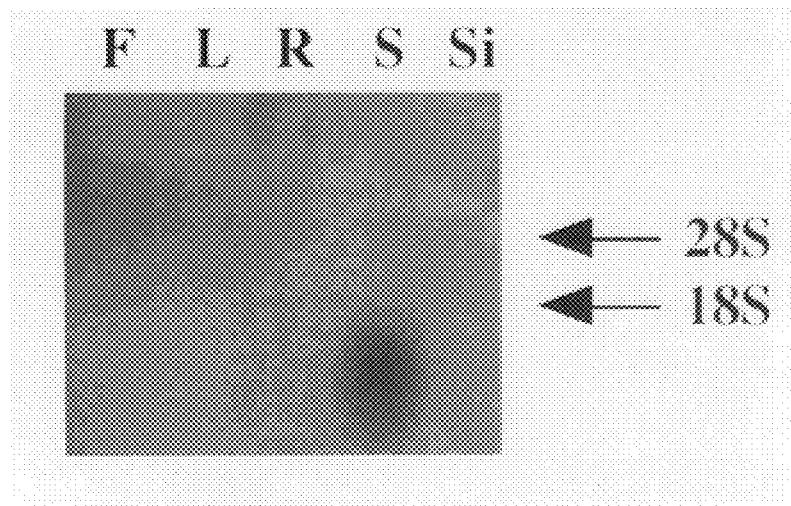
FIG. 3A depicts an autoradiograph of an RNA gel blot probed with cDNA inserts representing the AtS1 gene. Abbreviations are as follows: F, flower; L, leaf; R, root; S, immature seed; Si, silique without seed. The Location of 28S and 18S ribosomal RNAs are indicated.
Figure 3B:
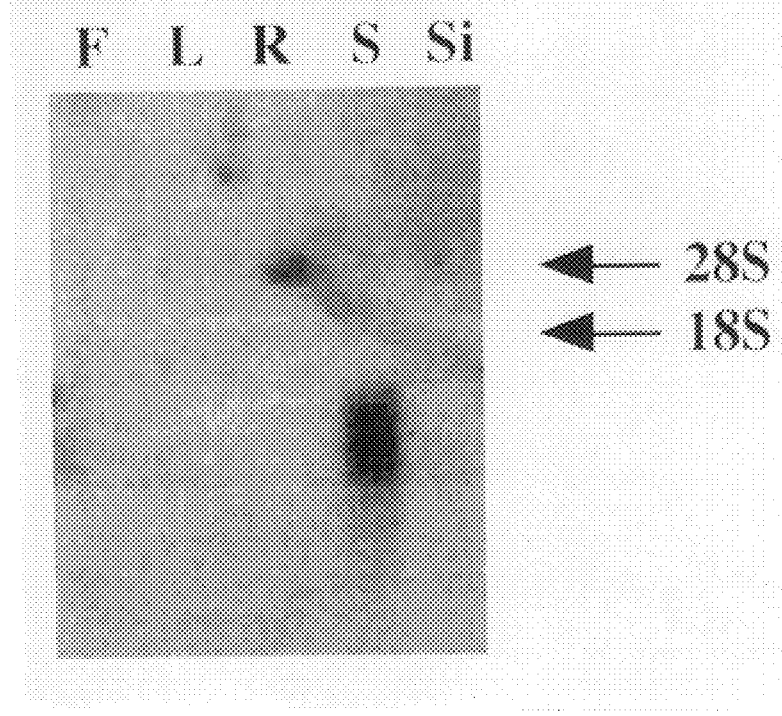
FIG. 3B depicts an autoradiograph of an RNA gel blot probed with cDNA inserts representing the AtS3 gene. Abbreviations are as in FIG. 3A. The Location of 28S and 18S ribosomal RNAs are indicated.

The seed specificity of the AtS1 and AtS3 cDNAs was confirmed by RNA gel blot analysis (FIGS. 2 and 3). Sequence analysis of both AtS1 and AtS3 cDNAs indicates that each represents a novel seed-specific gene and that transcripts representing both ATS1 and AtS3 are polyadenylated at different sites (FIG. 4).

TABLE 1

ANALYSIS OF PUTATIVE SEED SPECIFIC DIFFERENTIAL DISPLAY PRODUCTS

| Product | 10-mer used[a] | Size (bp) | cNDAs purified[b] | Genes represented[c] | Number of unique sequences[d] | RNA gel blot confirmation[e] | Designation | Comments |
|---|---|---|---|---|---|---|---|---|
| ddp1 | A12 | 450 | 6 | 3 | 1 | no | | |
| ddp2 | A12 | 370 | 5 | 3 | 2 | no | | |
| ddp3 | A12 | 300 | 10 | 5 | 2 | no | | |
| ddp4 | A10 | 710 | 12 | 6 | 2 | no | | |
| ddp5 | A10 | 500 | 12 | 3 | 1 | yes | AtS1 | This cDNA is represented 6 times |
| ddp6 | A10 | 150 | 8 | 5 | 2 | no | | |
| ddp7 | ca/b | 475 | 7 | 4 | 2 | yes | AtS2 | The cDNA was chimeric |
| ddp8 | ca/b | 450 | 12 | 4 | 1 | yes | AtS3 | This cDNA is represented 6 times |

TABLE 1-continued

ANALYSIS OF PUTATIVE SEED SPECIFIC DIFFERENTIAL DISPLAY PRODUCTS

| Product | 10-mer used[a] | Size (bp) | cNDAs purified[b] | Genes represented[c] | Number of unique sequences[d] | RNA gel blot confirmation[e] | Designation | Comments |
|---|---|---|---|---|---|---|---|---|
| ddp9 | ca/b | 300 | 12 | 9 | 2 | no | | |
| ddp10 | ca/b | 250 | 10 | 9 | 5 | no | | |

[a]The sequences of the arbitrary 10-mers used for the differential display experiment are: A10 (5'-gtgatcgcag-3'), A12 (5'-tcgccgatag-3'), ca/b (5'-ctagcttggt-3').
[b]This is the number of cDNAs plaque purified from the Arabidopsis immature seed cDNA library with the differential display probe. In each screen a total of 12 individual hybridizing plaques were targeted.
[c]The number of individual genes represented by the pool of plaque purified cDNAs.
[d]This number represents the unique genes in the cDNA pool. They are not represented in GeneBank.
[e]The cDNA probe recognized a seed specific mRNA.

TABLE 2

DEVELOPMENT EXPRESSION OF FOUR SEED SPECIFIC ARABIDOPSIS GENES
Hybridization*

| Probe | leaf | g–h | h–t | t–ec | ec—lc | dry |
|---|---|---|---|---|---|---|
| 12S cruciferin | 1 | 14 | 123 | 748 | 1510 | 454 |
| 2S albumin | 0 | 2 | 8 | 172 | 355 | 73 |
| AtS1 | 0 | 1 | 2 | 11 | 36 | 9 |
| AtS3 | 0 | 0 | 1 | 19 | 54 | 1 |

*The data represents the hybridization signal and is presented in arbitrary units which have been normalized for loading, probe specific-activity and probe length.

EXAMPLE 3

CHARACTERIZATION OF ATS1 AND ATS3 BY IN SITU HYBRIDIZATION

In situ hybridization analysis was used to establish the spatial accumulation of mRNA for each of the AtS1 and AtS3 genes. This approach utilized a digoxygenin-labeled RNA probe which was detected with an antibody conjugated to alkaline phosphatase. It was determined that this was the most reliable method to detect gene expression at the cellular level in developing Arabidopsis seeds.

Tissue representing developing Arabidopsis seeds and germinating seedlings was collected and fixed in a solution containing 4% formaldehyde and 0.5% glutaraldehyde in 100 mM phosphate buffer (pH 7.0) at 0° C. overnight. The tissue was dehydrated in 10%, 30%, 50%, 70%, 85%, 95%, and 100% ethanol three times for thirty minutes at room temperature for each step. The solvent was gradually changed to xylenes in the following series 25%, 50%, 75% and 100% three times at room temperature. An equal amount of Paraplast (Sigma, St. Louis, Mo.) was added to the xylenes and incubated overnight at room temperature. The mixture was then placed at 42° for 6 hours. It was decanted off, replaced with 100% molten paraplast and placed at 60° C. The paraplast was replaced four times at four hour intervals to remove all the xylenes. The paraplast embedded tissue was then poured into molds and cooled to room temperature. The embedded tissue was kept in a desiccated container at room temperature until sectioning.

Tissue was sectioned into 8 μm ribbons with a Lipshaw Model 50A microtome. The ribbons were overlayed on DEPC treated $H_2O$ on poly-L lysine coated microscope slides on a 45° C. slide warmer. The water evaporated overnight, fixing the sections to the slides. The slides were stored at room temperature.

The digoxygenin labeled riboprobes were prepared with the Genius™ 4 nonradioactive RNA in vitro transcription kit (Boehringer Mannheim, Indianapolis, Ind.). The cDNAs encoding the AtS1 and AtS3 genes were cloned into pBluescript (SK) as EcoRI/XhoI fragments. The template for antisense riboprobes was generated by an EcoRI digest, gel purified and quantitated. To generate the template for sense strand riboprobes, each cDNA was excised from pBluescript (SK) as EcoRI/XhoI fragments and cloned into pBluescript (KS) as the same. The template for the sense-strand riboprobe was constructed in the same method as the template for the antisense probe. Each riboprobe was synthesized in a reaction containing 2 μg linearized DNA template, 2 μl 10× T7 RNA polymerase buffer, 2 μl 10× NTPs containing digoxygenin-UTP, 1 μl RNAse inhibitor and 2 μl T7RNA polymerase (5U) in a 20 μl reaction. The reaction was incubated at 37° C. for 2 hours. The DNA template was digested with 5 Units of RNAse-free DNAse (Boehringer Mannheim, Indianapolis, Ind.) for 5 minutes at 37° C. The digoxygenin-labeled riboprobe was then purified over a G-50 spin column (Boehringer Mannheim, Indianapolis, Ind.) and ethanol precipitated.

Each riboprobe was sheared into strands averaging 100–200 bases by alkali treatment. RNA pellets were dissolved in 22 μl DEPC treated $H_2O$. Only 20 μl of the redissolved riboprobe was sheared with the addition of 20 μl 120 mM $Na_2CO_3$, 80 mM $NaHCO_3$ and incubating at 65° C. for 35 minutes. The reaction was terminated with the addition of 40 μl sodium acetate and the riboprobe was ethanol precipitated. The remaining riboprobe was reserved for gel analysis. Each riboprobe was resuspended in DEPC $H_2O$, quantitated and analyzed by gel electrophoresis. The riboprobes were kept at −90° C. until use.

The slides were prepared for hybridization first by removing the paraplast by immersion in 100% xylenes twice for 10 minutes each. The slides were transferred to 1:1 xylenes:ethanol for five minutes followed by 100% ethanol for two changes of 10 minutes each to remove the xylenes. The slides were then rehydrated through a series ($ddH_2O$:ethanol) of 5%, 15%, 30%, 50%, 70%, 85% and 95% $ddH_2O$ for five minutes each step. The slides were finally transferred to PBS (50 mM phosphate buffer(pH 7.0), 130 mM NaCl in DEPC $H_2O$ for two 5 minute incubations at room temperature. The slides were then incubated in 50 mM phosphate buffer (pH 7.0) containing 100 μg/ml proteinase K for 15 minutes at 37° C. The digests were stopped by two washes in PBS for five minutes each.

The tissue was then acetylated by incubation in fresh 1% triethanolamine (pH8.0), 0.5% acetic anhydride for 10 minutes at room temperature. The reaction was terminated by two washes in PBS for 5 minutes each. This was followed by a quick dehydration series in 5%, 15%, 30%, 50%, 70%, 85%, 95%, and two times 100% ethanol. The slides were air dried and kept at room temperature until the hybridization.

Each riboprobe was diluted to 300 ng/ml in hybridization solution containing 50% deionized formamide, 300 mM NaCl, 10 mM Tris-HCl(pH 7.5), 5 mM EDTA (pH 8.0), 1× Dendhart's solution, 10% dextran sulfate, 1 mg/ml yeast tRNA and 500 µg/ml poly-A RNA. The hybridization mixture was overlayed on each dried slide (250 µl per slide), covered with a coverslip, and incubated overnight in a moist container at 50° C.

The unhybridized probe was removed by washing the slides in 2× SSC/50% deionized formamide 4 times for 30 minutes each at 50° C. The slides were then washed in NTE buffer (500 mM NaCl, 10 mM Tris-HCl (pH 7.5), 1 mM EDTA (pH 8.0)) twice at 37° C. for 10 minutes each. The slides were then treated with 20 U/ml RNAse A plus 20 µg/ml RNAse T1 in NTE buffer for 30 minutes at 37° C. The RNAse cocktail was removed by 4 washes in NTE buffer at 37° C. for 30 minutes each. The slides were washed in 2× SSC/50% deionized formamide at 50° C. for 30 minutes and then washed in PBS at room temperature twice for 10 minutes each.

The slides were then incubated in Buffer I (100 mM Tris-HCl (pH 7.5), 150 mM NaCl) for 30 minutes at room temperature. The slides were blocked in Buffer I containing 1% BSA or gelatin at room temperature for 30 minutes. An anti-digoxigenin Fab fragment conjugated with alkaline phosphatase (Boehringer Mannheim) was diluted 1:2500 in Buffer I containing 1% BSA or gelatin and 500 µl was added to each slide. The slides were covered with cover slips and incubated at room temperature for one hour. The unhybridized antibody was removed with 4 washes in Buffer I at room temperature for 15 minutes each. The slides were rinsed in Buffer III (100 mM Tris-HCl (pH 9.5), 100 mM NaCl, 50 mM $MgCl_2$) for two minutes at room temperature and incubated in color solution to detect hybridization. The color solution contained 337.5 µg/ml NBT (nitroblue tetrazolium) and 175 µg/ml X-phosphate (5-bromo-4-chloro-3indolyl phosphate) in Buffer III. The color reaction was carried out for 2 hours to 3 days, depending on the experiment.

The color reactions were stopped by washing slides in deionized $H_2O$. The slides were dehydrated quickly in 30%, 50%, 70%, 85%, 95% and 100% ethanol and air dried. The samples were preserved in several drops of either Euparal (BioQuip Products, Inc., Gardena, Calif.) or Permount (Fisher, Fair Lawn, N.J.) and a cover glass was mounted. The mounted samples were dried for several days at room temperature. Micrographs of individual sections were taken with a Zeiss Axiophot microscope using DIC optics.

Figure 5A:
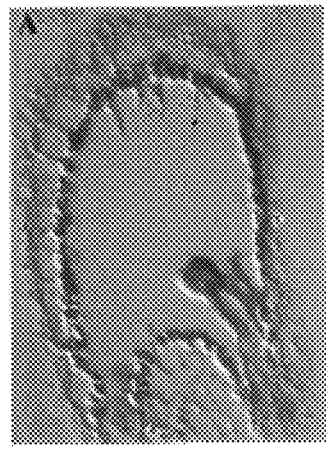
FIG. 5A is a photomicrograph showing in situ localization of AtS1 mRNA in a globular stage embryo.
Figure 5B:
FIG. 5B is a photomicrograph showing in situ localization of AtS1 mRNA in a heart stage embryo.
Figure 5C:
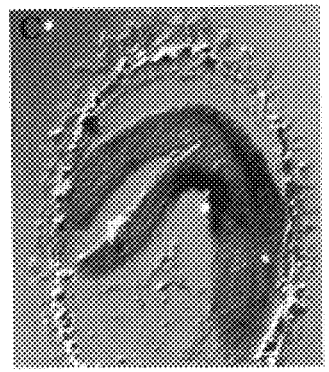
FIG. 5C is a photomicrograph showing in situ localization of AtS1 mRNA in a early cotyledon stage embryo.
Figure 5D:
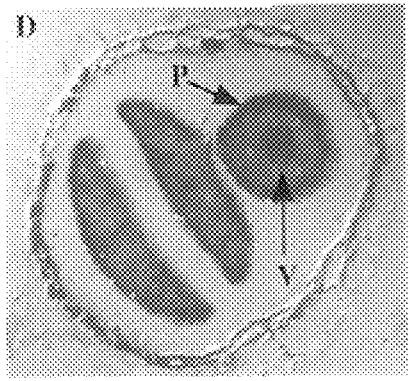
FIG. 5D is a photomicrograph showing in situ localization of AtS1 mRNA in a late cotyledon stage embryo, cross section. The protoderm (P) and provasculature (V) are indicated by the arrows.
Figure 5E:
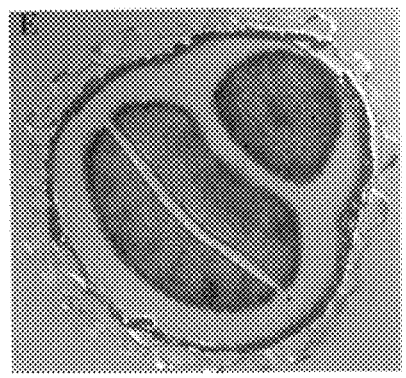
FIG. 5E is also a photomicrograph showing in situ localization of AtS1 mRNA in a late cotyledon stage embryo, cross section.
Figure 5F:
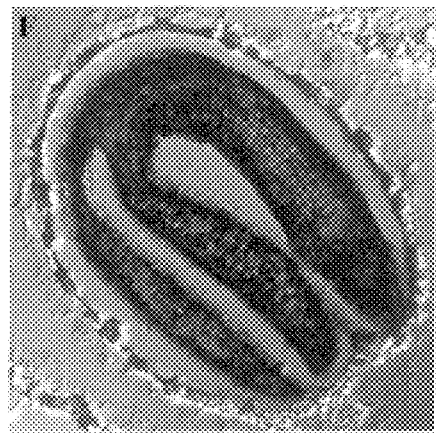
FIG. 5F is a photomicrograph showing in situ localization of AtS1 mRNA in a late cotyledon stage embryo, longitudinal section.
Figure 6A:
FIG. 6A is a photomicrograph showing in situ localization of AtS3 mRNA in an early cotyledon stage embryo.
Figure 6B:
FIGS. 6B and 6C are photomicrographs showing in situ localization of AtS3 mRNA in early cotyledon stage embryos, cross sections.
Figure 6C:
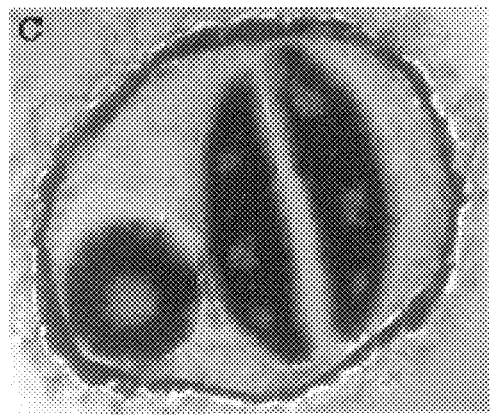
Figure 6D:
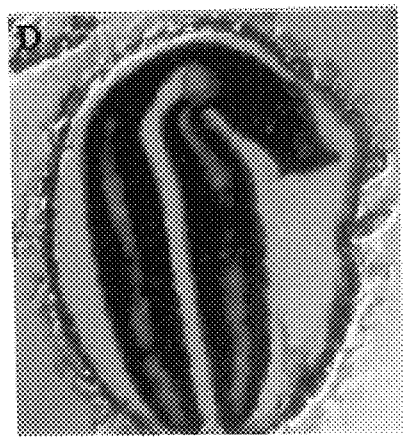
FIGS. 6D, 6E, and 6F are photomicrographs showing in situ localization of AtS3 mRNA in an late cotyledon stage embryos, longitudinal sections.
Figure 6E:
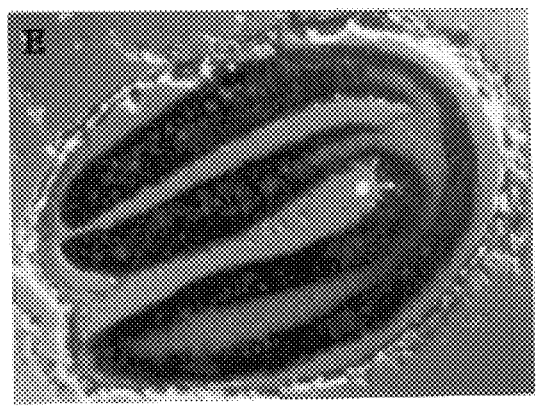
Figure 6F:
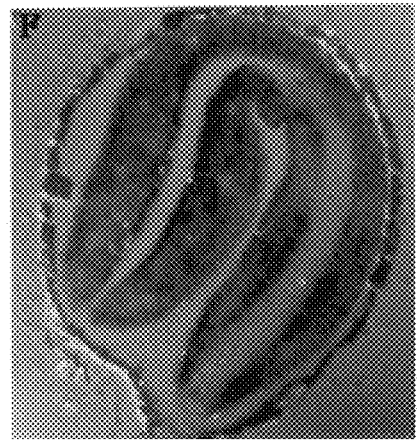

The in situ hybridization data is presented in FIGS. 5A through 5F and FIGS. 6A through 6F. The mRNA for both genes is first detected at the late torpedo stage. Expression above background was not detected in earlier embryos. As indicated in FIGS. 5C through 5F, the AtS1 gene is expressed throughout the maturing embryo. Expression is initially detected in the cortical parenchyma and gradually spreads throughout the embryo as it matures. FIGS. 5E and 5F indicate that expression levels are significantly enhanced in both the protoderm and vascular initials in the cotyledon stage embryo. This pattern is clearly seen in the cross sections (FIGS. 5D and 5E), but was not detected in longitudinal sections (FIG. 5F). In developing Arabidopsis embryos, a similar pattern was reported for the GEA1 gene (Gaubier et al. (1993) *Mol. Gen. Genet.*, 238; 409–418), indicating that the expression profile may not be unique to the AtS1 gene.

The in situ hybridization data for the AtS3 gene is resented in FIGS. 6A through 6F. The AtS3 gene is expressed in a pattern that closely resembles both the 2S and 12S genes with the earliest signals detected in the cortical parenchyma at the torpedo stage (Guerche et al., 1990; Pang et al., 1988). There is no expression detected in the procambium or the root and shoot apical meristems. This likely indicates that the AtS3 gene product is either a minor seed storage protein or is involved in the stable accumulation of seed storage proteins.

These data indicate that, while both genes are expressed in a similar temporal pattern, their spatial accumulation in the developing embryo is distinct. Furthermore, the expression of both genes is restricted to the developing embryo. No expression was detected in the embryo sac, endosperm or the germinating seedling, even after several days exposure to the colorimetric agent. Also, no signal was detected with sense strand riboprobes. This indicates that both AtS1 and AtS3 are involved in developmental processes unique to the maturing embryo. Due to their unique spatial expression however, each gene may be involved in distinct regulatory programs.

EXAMPLE 4

AtS1 AND AtS3 GENE ORGANIZATION
Genomic Clone Isolation

Genomic DNA was prepared from Arabidopsis (cv. Landsberg) according to Taylor et al. (1993) *Methods in Plant Molecular Biology and Plant Biotechnology*, Boca Raton, Fla.: CRC Press; 37–47. The DNA was partially digested with MboI and overlayed on a sucrose gradient for size selection (Ausubel et al., 1994). Fractions containing DNA fragments ranging from 15–25 kb were combined and precipitated. The DNA was dissolved in TE buffer, quantitated and ligated to lambda pGEM-11 XhoI half-site arms according to manufactures' instructions (Promega, Madison, Wis.). The DNA was packaged using Gigapack Gold packaging extracts (Stratagene, La Jolla, Calif.) and plated on KW251 cells. Characterization of this library revealed a 1% background and an average insert size of 20 kb. The library contained approximately $1.5 \times 10^6$ plaque forming units and was amplified and stored in SM buffer containing $CHCl_3$ at 4° C.

Approximately 25,000 pfu of this library was plated on KW251 cells. Plaques were transferred to nitrocellulose membranes as recommended by the manufacturer and hybridized by standard methods (Ausubel et al., 1994). After 4 hours of prehybridization in hybridization II buffer (1% crystalline BSA, 1 mM EDTA, 0.5 M $NAHPO_4$, pH 7.2 7% SDS) at 65° C., the random-primed DNA generated from either an AtS1 or AtS3 cDNA template, which had been boiled in 50% formamide for 3 minutes, was added to the same hybridization solution. Hybridization was continued up to 24 hours at 65° C. The filters were washed twice in 0.5% crystalline BSA, 1 mM EDTA, 40 mM $NaHPO_4$, pH 7.2, 5% SDS for 5 minutes each at room temperature, and then three times in 1 mM EDTA, 40 mM $NaHPO_4$, pH 7.2, 1% SDS for 10 minutes each at 65° C. Autoradiographs were exposed for 1 day at −95° C. Several phage were plaque purified with the AtS1 cDNA probe while only one clone was plaque purified with the AtS3 probe. Phage DNA was prepared using the liquid lysate protocol (Ausubel et al., 1994) and aliquots were separately digested with BamHI, EcoRI, HindIII, SacI, and XbaI. The AtS1 probe identified a 5.5 kb SacI fragment and the AtS3 probe identified an 8.0 kb XbaI fragment. These were subcloned into pBluescript (Stratagene, La Jolla, Calif.) and sequenced.

Southern Analysis

Arabidopsis genomic DNA was isolated from whole plants according to the CTAB (hexadecyltrimethylammonium bromide plant genomic DNA preparation protocol (Taylor et al., 1993). Genomic DNA (10 μg) was digested in the presence-of excess enzyme activity at 37° C. overnight and then resolved on a 0.7% agarose gel. Separate digestions using BamHI, EcoRI, HindIII, SacI and XbaI were performed on the genomic DNA. DNA was transferred by blotting to Hybond-N+™ membrane (Amersham) with 0.1 N NaOH. Southern hybridizations were performed essentially as described for the genomic clone isolation. After 4 hours prehybridization in hybridization II buffer (1% crystalline BSA, 1 mM EDTA, 0.5 M NaHPO$_4$, pH 7.2, 7% SDS) at the hybridization temperature, the random-primed DNA probe generated from either an AtS1 or AtS3 CDNA template, which had been boiled in 50% formamide for 3 minutes, was added to the same hybridization solution. Hybridizaiton was continued up to 24 hours. The filters were washed twice in 0.5% crystalline bSA, 1 mM EDTA, 40 mM NaHPO$_4$, pH 7.2, 5% SDS for 5 minutes each at room temperature, and then, stringently, three times in 1 mM EDTA, 40 mM NaHPO$_4$, pH 7.2, 1% SDS for 10 minutes each at high temperature. The high stringency hybridizations were performed at 68° C. and the stringent washing steps were done at the same temperature. The low stringency hybridizations were done at 50° C. and the stringent washing steps were done at 60° C.

Figure 7A:
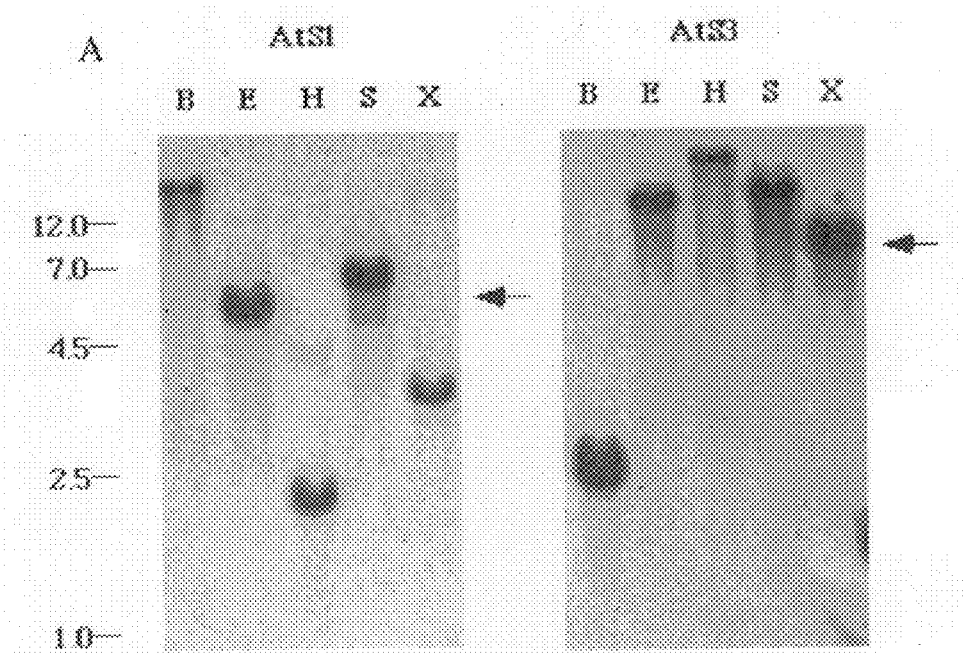
FIG. 7A shows two Southern hybridizations of Arabidopsis genomic DNA probed with either AtS1 or AtS3 cDNA probes under high stringency conditions. The arrows on the right indicate the genomic fragments that were subcloned for sequence analysis. Abbreviations are as follows: B,Bam HI; E,EcoRI; H, HindIII; S, SacI; X, XbaI.
Figure 7B:
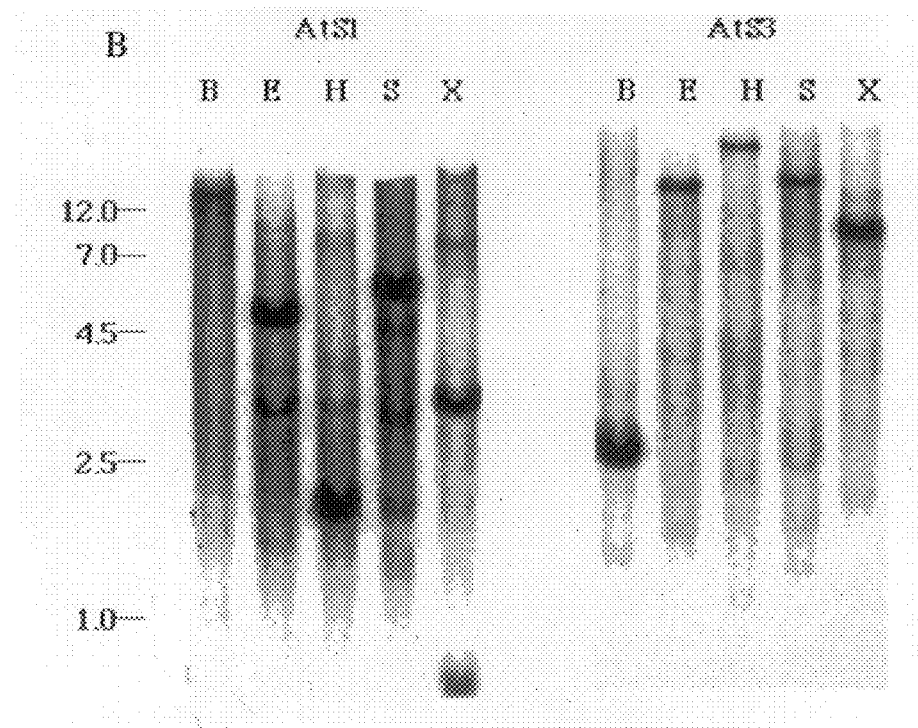
FIG. 7B shows two Southern hybridizations of Arabidopsis genomic DNA probed with either AtS1 or AtS3 cDNA probes under low stringency conditions. Abbreviations are as in FIG. 7A.

High stringency southern hybridization analysis of Arabidopsis genomic DNA indicated that both genes were present as single copies in the diploid genome (FIG. 7A). Southern hybridization analysis under low stringency revealed that the AtS1 probe hybridizes to two or three additional bands depending on the digest. Clone blot analysis of these phage indicate that each contains a hybridizing fragment identical to a band uncovered by the low stringency genomic southern blot, FIG. 7B. The clones which contained a hybridizing fragment corresponding to a band in the high stringency genomic DNA analysis, indicated by the arrows in FIG. 7A were identified. This corresponds to a 5.5 kb SacI fragment for AtS1 and an 8.0 XbaI fragment for AtS3. The DNA representing these bands was subcloned into pBluescript and completely sequenced.

DNA Sequencing and Sequence Analysis

Mini-prep plasmid DNA was used as templates in cycle sequencing reactions with the SequiTherm cycle sequencing kit (Epicenter Technologies, Madison, Wis.) or the ABI PRISM™ dye terminator cycle sequencing kit (Perkin Elmer, Foster City, Calif.). Sequence analysis was done locally with GCG (Devereux et al., 1984) on a DEC MicroVAXII; database searches were done remotely through NCBI using the BLAST algorithm (Altschul et al. (1990) *J. Mol. Biol.*, 215; 403–410).

Genomic and cDNA sequence data for each gene was aligned using Geneworks, Version 2.3 software (Intelligenetics, Mountain View, Calif.). Introns were initially located with a DNA dot matrix algorithm. Inspection of these regions found them to be flanked by consensus GU . . . AG sequence. The downstream genes identified on each genomic clone were found using BLAST and BLASTX data search algorithms (Altschul et al., 1990). The longest open reading frame found in each cDNA was considered to be the coding sequence and the codon for that methionine residue was labeled +1. The coding sequence was translated from that residue and hydrophobicity plots were generated using the Kyte-Doolittle algorithm.

Each genomic clone contained a complete target gene, including at least 1.3 kB of 5'-untranslated sequence. Alignment of the longest cDNA clone with each genomic clone revealed that the putative coding sequence is interrupted with introns with the consensus GU . . . AG borders. The data presented in FIGS. 8 and 11A indicate that AtS1 contains five introns and six exons, while FIGS. 9 and 11B indicate that AtS3 contains two introns and three exons. Alignment of several individual cDNAs with each genomic clone revealed that each transcript is terminated at a different position along a 120–300 base track (FIG. 4). Thus the AtS1 mRNA has at least a 185–300 base 3'-untranslated region, and the AtS3 mRNA has at least a 127–17.9 base 3'-untranslated region. The poly-adenylation sites are indicated by an asterisk in FIG. 8 and FIG. 9, respectively. No consensus poly-adenylation signal sequence was noted in the 3'-untranslated region of either cDNA, indicating that there is not a consensus poly-adenylation site in either gene.

The AtS1 and AtS3 genomic regions

Sequence analysis of the genomic regions downstream of both the AtS1 and AtS3 genes reveal that additional transcribed genes lie in close proximity. FIGS. 11A and 11B are diagrams detailing the known transcribed regions in the AtS1 and AtS3 genomic clones. As indicated in FIG. 11A, the gene encoding the Arabidopsis protein phosphotasex, PPX2 (Perez-Callejon et al. (1993) *Plant Mol. Biol.*, 23; 1177–1185), lies directly downstream of, and in tandem with, the AtS1 gene. The translation start codon is 1630 base pairs 3' of the AtS1 translation stop codon site. The sequence reported for this gene is identical to the sequence found in the AtS1 genomic clone. The PPX-2 gene is not expressed in the same pattern as that of the AtS1 gene. For example, PPX-2 gene expression was detected at relatively low levels in all tissues examined (Perez-Callejon et al., 1993). It is not known if any previously identified genes lie upstream of the AtS1 gene.

FIG. 11B indicates that the AtS3 genomic clone contains at least one additional transcribed gene. Two anonymous, overlapping cDNAs (GeneBank accession numbers Z30724 and T45484) align with the genomic DNA. These cDNAs identify a region spanning bases 4342–4845 in the AtS3 genomic clone, which is 1916–2419 bases downstream from the AtS3 translation stop condon. This gene is transcribed off the DNA strand opposite the AtS3 gene. Both of these sequences were identified in independent expressed sequence tag (est) projects. Structural analysis of these cDNAs reveal nothing regarding this gene's possible function in the plant.

EXAMPLE 5

FURTHER ANALYSIS OF GENOMIC ATS1 and ATS3 CLONES

Mapping of Transcription sites by RNAse Protection Analysis

The transcription start sites for both AtS1 and AtS3 were mapped by RNAse protection assay.

First, the riboprobes used to map the transcription start sites for AtS1 and AtS3 were constructed. A region encompassing the 5'-region of each cDNA was amplified in a Pfu polymerase reaction, gel purified and cloned into EcoRV digested pBluescript (SK–). The primers used to generate the AtS1 template were 5'-ttattattacctc-3' (primer T5RP) (SEQ ID NO:29) and 5'-gaagtctatcatcc-3' (primer T3RP) (SEQ ID NO:30) which yield a 189 bp fragment. The primers used to generate the AtS3 template were 5'-cactcacgagtgcctc-3' (primer 8g.5P)(SEQ ID NO:31) and 5'-acaagaagaacctgg-3' (primer 8g.3P)(SEQ ID NO:32) which yield a 166 bp fragment. Both fragments were oriented so that the antisense riboprobe was transcribed from the T7 promoter. Each clone was linearized with an EcoRI digest and gel purified. Approximately 2 μg of linearized template was used in an in.vitro transcription reaction to produce high specific activity probe according to the manufacturer's instructions (Stratagene, La Jolla, Calif.). The probe was gel purified on a non-denaturing acrylamide gel. Bands representing full-length transcript were excised and the probe was eluted into TE buffer overnight at 37° C. Incorporation of radioactive label was measured and the probes were used immediately.

Total RNA was prepared from dry Arabidopsis seed. The RNAse protection experiment was performed using the Direct Protect kit (Ambion, Austin, Tex.). The manufacturer's instructions were used with the exception of the following modifications. First, it was determined that a better signal was achieved when total RNA prepared from dry seeds was substituted for tissue. Second, approximately 250,000 cpm of probe was used with each sample. Total RNA amounting to 0, 2, 5, 10, and 20 μg were combined with probe and lysis buffer in a total volume of 50 μl and incubated overnight at 37° C. The reactions were completed according to manufacturers instructions and the protected fragments were resolved on a 6% sequencing gel along with a sequencing reaction primed by the 3'-terminal primer (AtS1-T3RP and AtS3-8g.3P) used to generate each riboprobe template. Protected fragments were identified as bands demonstrating increasing intensity with increasing total RNA template concentration. The size of the protected fragments was determined by comparing the size of co-migrating DNA ladder generated by the sequencing reaction (Calzone et al. (1987) *Methods in Enzymology*, 152; 611–632). Since a protected fragment did not co-migrate with the undigested probe, it was assumed that the transcription start site for each gene was contained within the boundaries of the riboprobe template.

Figure 10A:
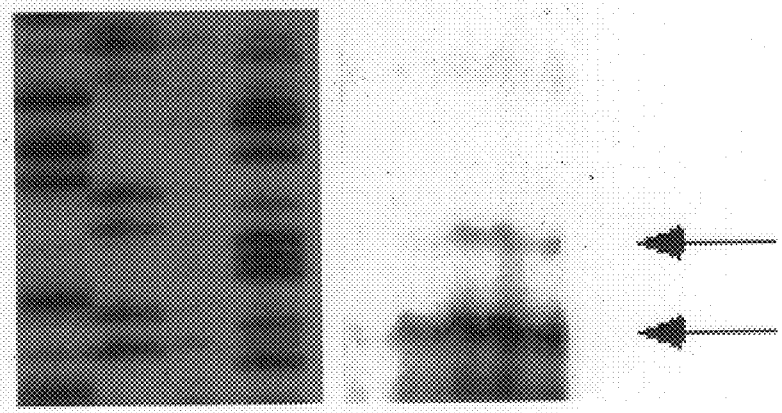
FIG. 10A is an autoradiograph of the reaction products of an RNAase protection assay electrophoresed through a 6% sequencing gel and used to identify the transcriptional start site for the AtS1 gene. Protected fragments were identified as bands (indicated by arrows) which increase in intensity as total RNA template increases. Bases corresponding to these protected fragments are indicated by a double under line in FIG. 8.
Figure 10B:
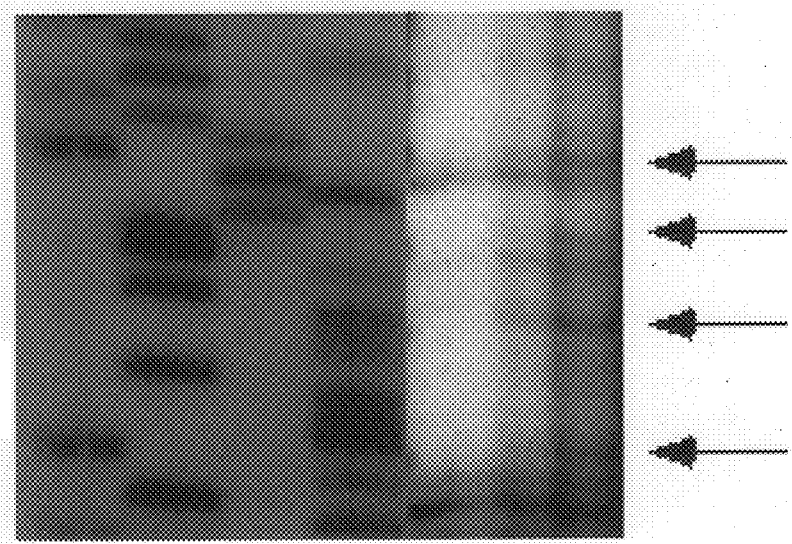
FIG. 10B is an autoradiograph of the reaction products of an RNAase protection assay electrophoresed through a 6% sequencing gel and used to identify the transcriptional start site for the AtS3 gene. Protected fragments were identified as bands (indicated by arrows) which increase in intensity as total RNA template increases. Bases corresponding to these protected fragments are indicated by a double under line in FIG. 9.

Experimental results are detailed in FIGS. 10A (AtS1 gene) and 10B (AtS3 gene). Protected fragments, indicated by the arrows, were identified as titrated bands on a sequencing gel. Bands which did not titrate were ignored. Bands equal to or greater than each probe's length were not detected, indicating that no other transcription start site occurs upstream of the sequence analyzed. This data reveals two transcription start sites in the AtS1 gene (FIG. 10A) and four in the AtS3 gene (FIG. 10B). These sites are indicated by a double underline in FIGS. 8 and 9, respectively. The signal strength indicates that the AtS1 gene is preferentially transcribed from the site that is more proximal to the translation start site, while the AtS3 gene does not appear to have a preferential site. A putative TFIID binding site and CAT box were also identified upstream of each transcription start site (FIGS. 8 and 9).

EXAMPLE 6

ESTABLISHMENT OF SEED SPECIFICITY FOR THE GENE PRODUCTS OF AtS1 and AtS3

Antisera Production

DNA representing the putative coding sequence for both the AtS1 and AtS3 genes was subcloned into the pET expression vector pET-30a(+) (Novagen, Madison, Wis.). The coding sequence for AtS1 was excised from the cDNA ddp5(8) as an EcoRI/XhoI fragment and ligated directly into the expression vector. To generate an in frame fusion with the AtS3 coding sequence, two primers, 5'-accgaattca tggcattcga cctcagcatc-3' (AtS3-5' del)(SEQ ID NO:33) and 5'-cgtgagctct cactaatttc caagccttga agc-3' (AtS3-3' del) (SEQ ID NO:34), were used in a Pfu polymerase reaction to amplify the coding sequence. The Pfu product was digested with EcoRI/SacI, gel purified and ligated into the pET-30a (+) expression vector. The integrity of each coding sequence was verified by sequence analysis.

Fusion proteins tor both AtS1 and AtS3 were generated and purified by affinity chromatography on a nickel column according to manufacturers instructions (Novagen, Madison, Wis.). The integrity of each purified fusion protein was verified by SDS/PAGE and western analysis. Each protein was combined with RIBI adjuvant and injected subcutaneously into rabbits to raise polyclonal antibodies against the AtS1 and AtS3 gene products. Each antibody was then used in western and light level immunolocalization analysis to establish the seed specificity of both gene products.

Western Analysis

Total protein was extracted from fresh plant tissue by homogenizing fresh tissue in protein extraction buffer (50 mM NaPO$_4$ (pH 7.0), 150 mM NaCl, 10 mM EDTA, 10 mM 2-mercaptoethanol, 0.1% sodium sarcrosyl, 0.1% Triton X-100, 4% sodium dodecyl sulfate, 2 M urea) at 4° C. Insoluble material was separated by centrifugation at 13,000×g for 10 minutes at 4° C. The supernatant was removed and total protein was measured by the method of Bradford (1976) *Anal. Biochem.*, 72; 248–254. Total protein was resolved on a 12.5% denaturing polyacrylamide gel and electroblotted onto nitrocellulose (Ausubel et al., 1994). The filter was incubated in blocking solution (10 mM Tris-HCl (pH7.5), 150 mM NaCl, 1% BSA, 0.2% NP-40) for 30 minutes at room temperature. Primary antiserum was diluted in blocking solution as indicated and incubated overnight at room temperature. The filter was washed four times in washing solution (10 mM Tris-HCl (pH 7.5), 150 mM NaCl, 0.1% SDS, 0.2% NP-40, 0.25% sodium deoxycholate) for 15 minutes each at room temperature. This was followed by a rinse in 10 mM Tris-HCl (pH 7.5), 150 mM NaCl to remove detergent for 10 minutes at room temperature. The filter was then incubated in blocking solution containing 1:5000 goat anti-rabbit FAB fragment conjugated to alkaline phosphatase for 1 hour at room temperature. The filter was washed as described for the primary antibody. The hybridization was detected through an alkaline phosphatase reaction.

Figure 12A:
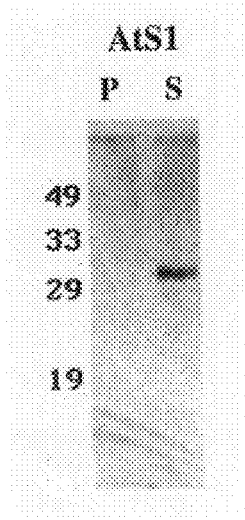
FIG. 12A depicts a western blot of Arabidopsis root, leaf, stem and flower total protein (P) and developing silique protein (S) reacted against rabbit antisera raised against fusion proteins representing the AtS1 gene product. The reaction was detected using an anti-rabbit antibody conjugated to alkaline phosphatase.
Figure 12B:
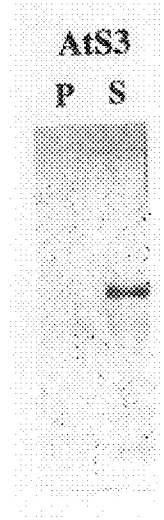
FIG. 12B depicts a western blot of Arabidopsis root, leaf, stem, and flower total protein (P) and developing silique protein (S) reacted against rabbit antisera raised against fusion proteins representing the AtS3 gene product. The reaction was detected using an anti-rabbit antibody conjugated to alkaline phosphatase.

As the Western blot indicates in FIGS. 12A and 12B, each antibody specifically reacts with a band in immature seed tissue. This data indicates that the open reading frame for both AtS1 and AtS3 has been correctly interpreted. The band recognized by the AtS1 antibody has a molecular weight of 33 kD, somewhat larger than the predicted 28,020 Dalton from the cDNA sequence. This discrepancy might indicate that the native protein is either covalently modified to produce the mature protein or that it migrates at a slower than predicted rate in the gel. The AtS3 antibody specifically recognizes a 30 kD band. This is also somewhat larger than the predicted molecular weight of 23,042 Daltons. In the case of both AtS1 and AtS2, the antibodies do recognize seed-specific proteins which are close to the predicted molecular weight of the AtS1 and AtS3 gene products. Thus, Western analysis of prebleed and primary antisera from each rabbit indicate that each rabbit produced antibodies against the affinity purified target protein. Furthermore, antisera taken from these immunized rabbits identified a protein in total protein extracts prepared from developing Arabidopsis seeds and did not react with total protein extracted from other Arabidopsis tissues.

Immunolocalization

Immature seed tissue was prepared and embedded in paraplast in a manner identical to that used for in situ localization of Example 3. The paraplast was removed and the tissue rehydrated as described in Example 3. The tissue was treated with 100 μg/mL proteinase K as described above, except the reaction was carried out for 10 minutes at room temperature. The slides were subsequently acetylated as described above. After two 5 minute rinses in PBS at room temperature, the slides were equilibrated in 10 mM Tris-HCl (pH 7.5), 150 mM NaCl, 0.2% NP-40 for 10 minutes at room temperature. The slides were then incubated in blocking buffer (10 mM Tris-HCl (pH 7.5), 150 mM NaCl, 0.1% NP-40, 5% goat serum (Sigma, St. Louis, Mo.) at room temperature for 1 hour. The primary antiserum was preadsorbed to fixed plant tissue as previously described (Perry et al. (1996) *Plant Cell*, 8; 1977–1989). Hybridization to the primary antiserum was carried out using a 1:100 dilution in blocking buffer at 4° C. for at least 12 hours. The unbound antibody was removed through extensive incubations in wash buffer (10 mM Tris-HCl (pH 7.5), 150 mM NaCl, 0.1% NP-40, 0.1% SDS, 0.25% sodium deoxycholate) over a 12 hour period at room temperature. The detergent was removed by a 20 minute incubation in 10 mM Tris-HCl (pH 7.5), 150 mM NaCl, 0.2% NP-40 at room temperature. The slides were then incubated in blocking solution containing 1:5000 goat anti-rabbit FAB fragment conjugated to alkaline phosphatase for 1 hour at room temperature. They were washed as described for the primary antibody. The hybridization was detected through an alkaline phosphatase reaction.

Figure 13A:
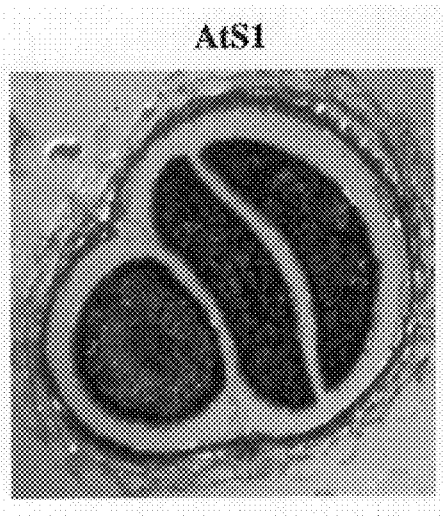
FIG. 13A depicts immunolocalizaton of the AtS1 gene product in an immature seed. The fusion proteins were raised in E. coli and affinity purified prior to injection into rabbits. The reaction was detected using an anti-rabbit antibody conjugated to alkaline phosphatase.
Figure 13B:
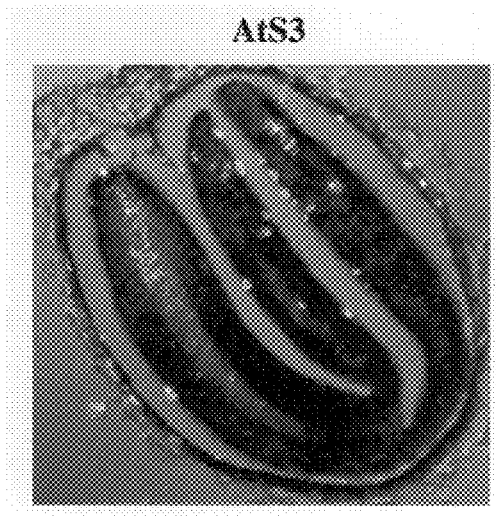
FIG. 13B depicts immunolocalization of the AtS3 gene product in an immature seed. Fusion proteins were raised as in FIG. 13A and hybridization was detected as in FIG. 13A.

Light level immunolocalization was used to refine this localization in immature seed tissue. As FIGS. 13A and 13B indicate, each gene product accumulates in immature embryos. Further, localization corresponds to the cells that express each gene (compare FIGS. 13A and 13B with FIGS. 5A–5F and 6A–6F). This data further supports the correct interpretation of the AtS1 and AtS3 structural data and reveals that two novel seed proteins have been identified.

Chromosome Mapping of AtS1

Figure 14:
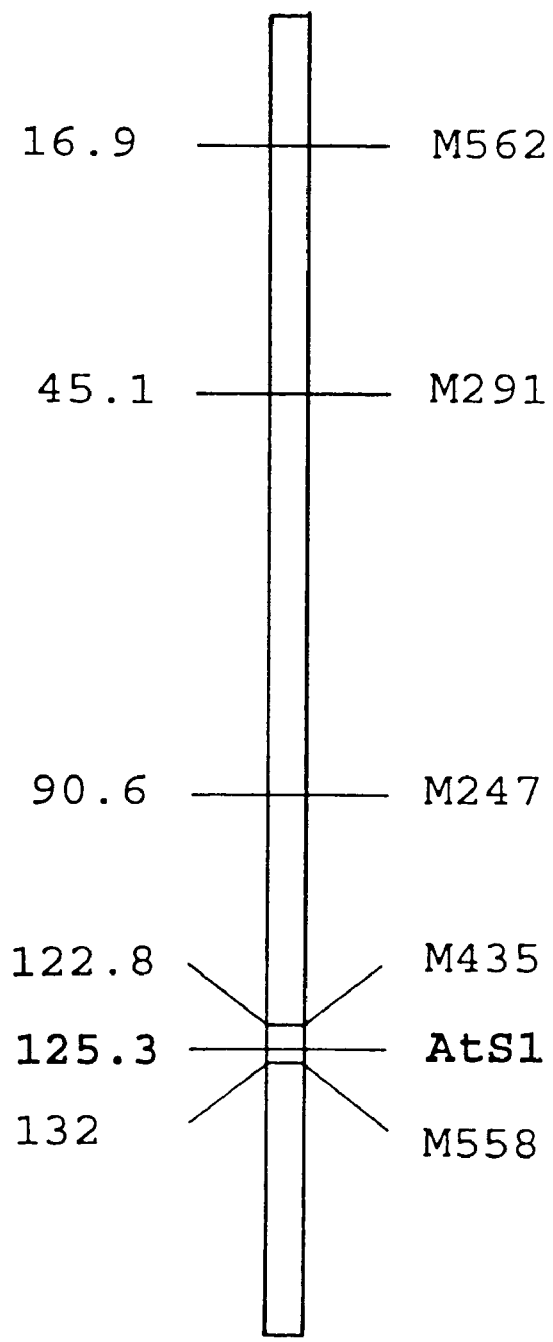
FIG. 14 shows the chromosome map position of AtS1 by RFLP analysis.

Experiments to determine the map position of both AtS1 and AtS3 were also carried out and were successful in identifying the map position of AtS1. This map position was determined by RFLP analysis of an F2 population segregating from a cross between the WS and HM ecotypes. Inheritance of a CfoI polymorphism identified within the AtS1 sequences was correlated with the inheritance of other markers using the Mapmaker computer program (Lander et al. (1987) *Genomics*, 1; 174–181). By this analysis, AtS1 was mapped to the bottom of Arabidopsis chromosome 5, approximately 9.2 centimograns above the RFLP marker M558FQ and approximately 2.5 centimorgans below M435F (Kowalski et al. (1994) *Genetics*, 138; 499–510). This is diagramed in FIG. 14.

The AtS3 gene has not been chromosome mapped. A polymorphism between the WS and HM ecotypes used in the analysis for the AtS1 gene was not found. A second attempt to map AtS3 gene in the segregating F2 population generated from a cross between Columbia and Landsberg ecotypes was initiated (Lister et al. (1993) *Plant J.*, 4; 745–750). This experiment sought to identify a gene specific cleaved amplified polymorphism (CAPS marker; Konieczny et al. (1993) *Plant J.*, 4, 403–410) between these two lines and was unsuccessful, even after examining over 80 different restriction enzymes. No attempt to identify another gene specific region was initiated. However, hybridization of an AtS3 gene-specific probe to the ordered bacterial artificial chromosome (BAC) library generated at Texas A&M University (Choi et al. (1995a) *Plant Mol. Biol.* Reporter, 13; 124–128; Choi et al. (1995b) *Weeds World*, 2; 17–20) has identified two BACs (T2N4 and T4F18) which contain the AtS3 gene. This library is being used in an ongoing multi-national effort to sequence the Arabidopsis genome. One of these BACs, T2N4 has been localized to chromosome 1. Eventually, T2N4 will be mapped and the location of the AtS3 gene determined.

Analysis of the Deduced Amino Acid Sequence for AtS1 and AtS3

The largest continuous open reading frame (ORF) for both AtS1 and AtS3 was conceptually translated (FIGS. 8 and 9, respectively). As indicated earlier, these gene products have not been functionally defined. An est representing the AtS1 gene has been identified in an Arabidopsis dry seed cDNA library. The GeneBank accession numbers for this est clone (cDNA number pap232) are Z20553 and Z29900. Recently, a cDNA with significant similarity to AtS1 was identified in rice. This gene, designated EFA27, was identified as an ABA responsive gene in rice seedlings, and further analysis indicated that it also responds to osmotic stress. It is expressed in developing seeds in a pattern similar to AtS1 expression (Frandsen et al. (1996) *J. Biol. Chem.*, 271; 343–348). An alignment of these cDNAs reveals that they are 60.9% identical, and the gene products are 64.4% similar as shown in FIG. 15 (Huang et al., 1991). The data in FIGS. 3–10B also reveals two highly conserved regions that are nearly 100% conserved at the protein level (Frandsen et al., 1996).

This is the only gene identified by AtS1, besides the pap232 clone, in the databases (Altschul et al., 1990). However, database searches with the coding sequence of EFA27 uncover a second Arabidopsis est (ATTSO251, GeneBank accession number Z17677). This cDNA is not identified in similar searches using the AtS1 coding sequence. Sequence alignments of ATTS0251 with EFA27 reveal that they are 62.1% identical (FIG. 16A). This gene is only 57.5% identical to AtS1 (FIG. 16B). These data would argue that EFA27 and AtS1 are related, perhaps members of a small gene family, but they may not be functional homologs of one another.

Figure 17A:
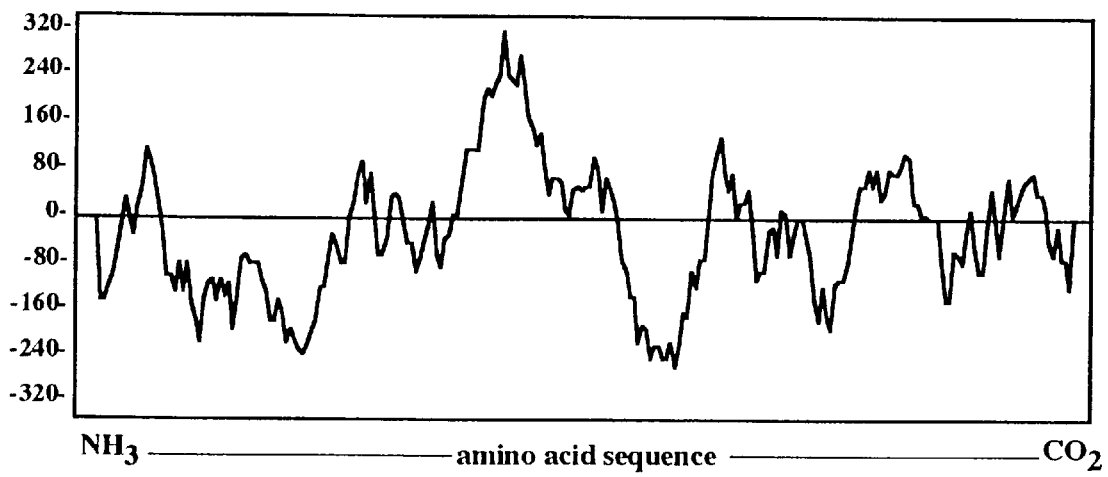
FIG. 17A is a graph depicting hydropathy analysis for the AtS1 gene product. The conceptual open reading frame for AtS1 was translated and subjected to Kyte Doolittle hydropathy analysis algorithm.
Figure 17B:
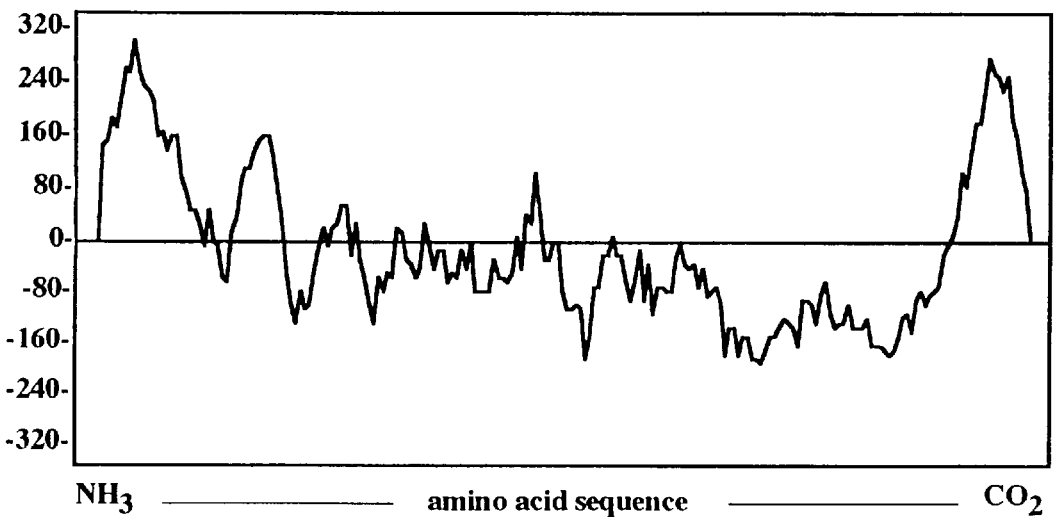
FIG. 17B is a graph depicting hydropathy analysis for AtS3. The conceptual open reading frame for AtS3 was translated and subjected to Kyte Doolittle hydropathy analysis algorithm.

The AtS3 gene did not match any known sequence. There is no evidence for an AtS3 homolog in the public databases. This gene does not contain a known functional domain as defined by BEAUTY search algorithms (Worley et al. (1995) *Genome Res.*, 5; 173–184). However, a Kyte-Doolittle hydrophobicity plot of the putative gene product reveals two very hydrophobic domains, one at the amino terminus and the other at the carboxy terminus (FIG. 17A). This may indicate that the AtS3 gene product is embedded in a membrane and may be a receptor or a structural membrane protein.

EXAMPLE 7

HETEROLOGOUS GENE EXPRESSION UNDER CONTROL OF THE AtS1 AND AtS3 PROMOTERS

Construction of Transcriptional and Translational Promoter-GUS Fusions

Four expression cassettes based on each gene, AtS1 and AtS3, were constructed. In each expression cassette, the 5'-upstream regulatory region or the 5'-upstream regulatory region along with the 5'-untranslated region were fused to the bacterial uidA gene encoding the β-glucuronidase (GUS) enzyme (Jefferson et al., 1987b). These include transcriptional and translational fusions in a pBI101-based binary vector (FIGS. 18A and 18B). These cassettes utilize the Agrobacterium nopaline synthase terminator (NOS terminus) to serve as a transcriptional terminator and polyadenylation signal (Bevan, 1984). The data presented in Examples 2 and 3 indicate that both the AtS1 and AtS3 genes utilize multiple polyadenylation sites and neither contains a consensus polyadenylation signal that might be predicted based on the literature. This is not an unusual situation in the plant kingdom (Li et al. (1995) *Plant Mol. Biol.*, 28; 927–934; Gaubier et al., 1993) and indicates that polyadenylation in plants is not well understood.

β-Glucuronidase (GUS) reporter cassettes used throughout were in pBIN19 (Bevan, 1984; Jefferson (1987a) *Plant Mol. Biol.* Reporter, 5; 387–405). PCR was used to generate each promoter element. To construct the transcriptional fusions, two oligonucleotide primers, 5'-cgcggatcca aagaaagagg cactcgtgag-3' (SEQ ID NO:35) and 5'-gcgcctaggg agtaaagagt ataatg-3' (SEQ ID NO:36) were designed to anneal to the 3' flanking sequence of the AtS1 and AtS3 promoters, respectively, and introduce a BamHI restriction site to facilitate cloning. Each primer was then used in conjunction with either the T3 (ATTAACCCTCACTAAAG) SEQ ID NO:35 (AtS3) or T7 primer (AATACGACTCACTATAG) SEQ ID NO:36 (AtS1) in a Pfu polymerase reaction to amplify the transcriptional promoter element of each gene with subcloned genomic DNA fragments as template. The reactions contained 2.5 µM each of the 5'- and 3'-primer, 1× Pfu polymerase reaction buffer (10 mM KCl, 10 mM (NH$_4$)$_2$SO$_4$, 20 mM Tris-HCl (pH 8.75), 2 mM MgSO$_4$, 0.1% Triton®X-100, 100 µg/ml BSA), 100 µM each dNTP, and 5 Units Pfu polymerase (Stratagene, La Jolla, Calif.) in a 25 µl reaction. The reactions were subjected to a thermocycle program consisting of a 4.5 minute initial denaturation step followed by 40 cycles of 30 seconds at 95° C., 1 minute at 42° C., and 1 minute at 72° C. This was followed with a 5 minute extension step at 72° C. The reaction products were purified by agarose gel electrophoresis and the Qiaquick™ gel extraction kit (Qiagen, Calif.).

Transcriptional fusions to the β-glucuronidase reporter gene were constructed using the binary vector pBI01 (Jefferson et al., 1987b). The AtS1 transcriptional fusion (1tsp, FIG. 18A) was constructed by digesting the AtS1 transcriptional promoter fragment with SacI and end-filling with T4 DNA polymerase. The fragment was then digested with BamHI. The pBI101 vector was digested with HindIII, filled in with Klenow DNA polymerase and digested with BamHI. The pBI101 DNA was treated with shrimp alkaline phosphatase according to manufacturer's instructions (Gibco-BRL). The AtS3 transcriptional fusion (3tsp, FIG. 18b) was constructed by digesting the AtS3 transcriptional promoter with XbaI and the pBI101 vector DNA with XbaI/SmaI. The pBI101 vector DNA was treated with shrimp alkaline phosphatase as described above. Both vector and promoter DNA were gel purified as described above, ethanol precipitated and resuspended in 8 µl MQH$_2$O each. Both the promoter element and vector DNA were combined in a 19 µl reaction containing 1×T4 DNA ligase buffer (50 mM Tris-HCl (pH 7.5), 10 mM MgCl$_2$, 10 mM dithiothreitol, 1 mM ATP, 25 µg/ml BSA) and 10 Units T4 DNA ligase (NEB) and incubated for 12 hours at 15° C. Upon completion, a fraction of this reaction was transformed into the bacterial host, DH10B (Gibco-BRL), by electroporation.

Positive promoter fusions were verified by both restriction and sequence analysis. Mini-prep plasmid DNA was used as templates in cycle sequencing reactions with the SequiTherm cycle sequencing kit (Epicenter Technologies, Madison, Wis.) or the ABI PRISM™ dye terminator cycle sequencing kit (Perkin Elmer, Foster City, Calif.). Sequence analysis was done locally with GCG (Devereux et al., 1984) on a DEC MicroVAXII; database searches were done remotely through NCBI using the BLAST algorithm (Altschul et al., 1990).

To construct the translational fusions (1tlp, FIG. 18A and 3tlp, FIG. 18B), an oligonucleotide primer SEQ ID NO:37 (5'-catgccatgg ctctctctct ttgtctctag actg-3' (AtS1); SEQ ID NO:38 5'-ctagccatgg tacttcagag atttgtgtg-3' (AtS3)) was designed to anneal to the 3'-flanking sequence of each promoter and introduce an NcoI restriction site to enable in-frame translational fusions. Each primer was then used in conjunction with either the T3 (AtS3) or T7 primer (AtS1) in a Pfu polymerase reaction, as described above, to generate each gene's translational promoter element. The reaction products were gel purified as described above. The translational fusion to the β-glucuronidase reporter gene was achieved by digesting both the vector, NCO-GUS (Maldonado-Mendoza et al. (1996) *Plant Physiol.*, 110; 43–49), and insert DNA with NcoI and PstI (AtSI) or XbaI (AtS3). Vector DNA was treated with shrimp alkaline phosphatase as described above. All DNA fragments were gel purified, ligated and transformed into DH10B as described above. Each construct was verified by both restriction and sequence analysis as discussed above. The complete promoter-GUS fusions, including the NOS-terminus, were excised as a BamHI/EcoRI fragment (AtS1) and an XbaI/EcoRI fragment (AtS3), ligated into the binary vector pBin19 (Bevan, 1984; Jefferson et al., 1987b), and transformed into DH10B as described above.

Transformation of Plants with Promoter-GUS Fusions

The pBin19-based plasmid constructs were used to transform *Arabidopsis thaliana* (cvs. Landsberg erecta or Columbia) and, in some cases, tobacco (*Nicotiana tabacum* cv Xanthi) according to standard procedures (Bechtold et al., 1993; Horsch et al., 1985; Nunberg et al., 1994; Valvekens et al. (1988) *Proc. Natl. Acad. Sci. USA*, 85; 5536–5540). Constructs were transferred into either the LBA4404 or the GV3101 *Agrobacterium tumefaciens* strains. Constructs were then transformed into tobacco leaf discs according to Nunberg et al. (1994) and Arabidopsis using either root transformation (Valvekens et al., 1988) or vacuum infiltration (Bechtold et al., 1993). Positive tobacco transformants were selected as described in Nunberg et al. (1994). Positive Arabidopsis transformants were selected on media containing 50 µg/mL kanamycin and 600 µg/mL carbenicillin. Regenerated plants were transferred to soil. Transgenic tobacco plants were grown under the optimal conditions described in Nunberg et al. (1994). Plants were self-pollinated, and seeds were regenerated on 400 µg/mL kanamycin (tobacco) or 50 µg/mL kanamycin and 600 µg/mL carbenicillin (Arabidopsis). The copy number of each GUS construction integrated into the plant genome was determined by genomic DNA gel blot analysis. GUS activity was analyzed in R2 progeny.

Biochemical and Histochemical Detection of GUS Activity

The standard procedures of Jefferson (1987a) and Jefferson et al. (1987b) as detailed in Bogue et al. (1990) and Nunberg et al. (1994) were followed. Biochemical assays were performed by mixing plant tissue lysates with an equal volume of 2 mM 4-methylumbelliferyl β-D-glucuronide and incubating for 1 hour at 37° C. Fluorometric analyses were done with a minifluorometer (model TKO-100; Hoefer Scientific Instruments, San Francisco, Calif.) as described previously (Jefferson, 1987a). Protein concentrations were determined by the method of Bradford (1976). Histochemical localizations for GUS activity were determined by incubating whole tissue in 1 mM 5-bromo-4-chloro-3-indolyl glucuronide (X-gluc) as described by Jefferson (1987a) and Jefferson et al. (1987b). The reactions described here were done in the presence of 1 mM potassium ferricyanide and 1 mM potassium ferrocyanide. The X-gluc treatment was carried out for the indicated times at 37° C. Samples were mounted on microscope slides with 80% glycerol, and visualized by photomicrography using Kodak Ektochrome 160 ASA tungsten film.

Figure 19A:
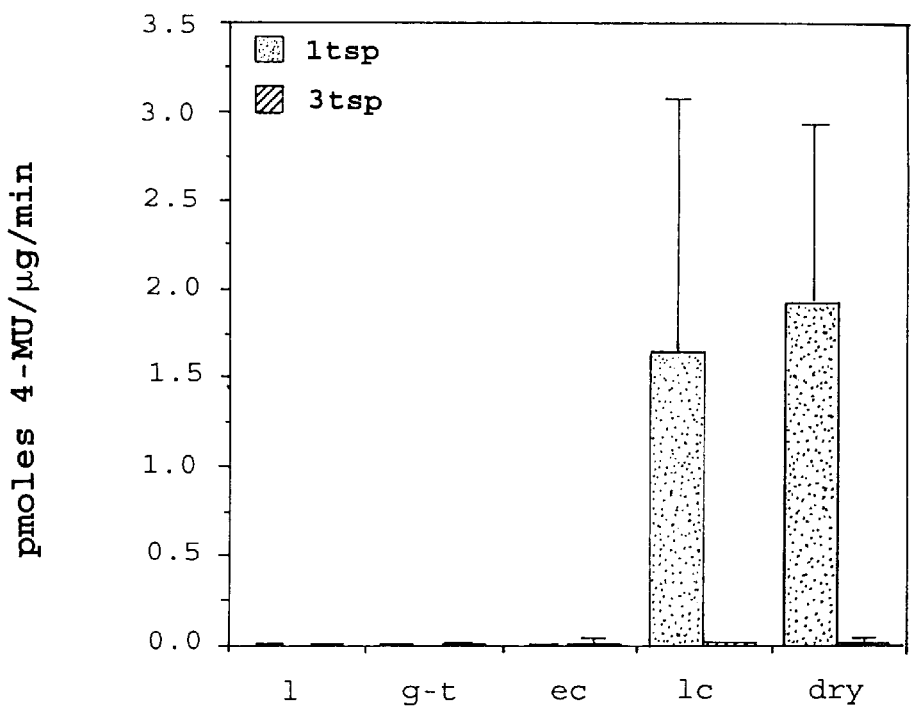
FIG. 19A graphically depicts developmental expression of the AtS1 and AtS3 transcriptional fusions, 1tsp and 3tsp in transgenic Arabidopsis. Abbreviations are as follows: 1, leaf; g-t, globular to torpedo stage embryos; ec, early cotyledon embryos; lc, late cotyledon embryos; and dry, mature dry seeds. Each tissue sample was assayed in triplicate and the data represents the mean between individual plants.

The data in FIG. 19A demonstrate that the AtS1 promoter (1tsp) is sufficient to confer seed-specific GUS accumulation in transgenic Arabidopsis. This activity is quantitively enhanced up to 10-fold when the 5'-UTR is included in the construct (1tlp in FIG. 19B). This alteration does not affect the spatial accumulation of GUS activity in the developing embryo (FIGS. 20A and 20B). In contrast, the data in FIGS. 19A and 19B reveals that the AtS3 promoter (3tsp) confers little embryo-specific GUS accumulation in Arabidopsis. The 3tsp expression cassette produces GUS levels slightly above background levels (FIG. 19A). In these experiments, background GUS activity is defined as activity measured in non-seed tissue such as leaf. The lower activity of the AtS3 promoter is overcome by the addition of the AtS3 5'-UTR (3tlp, FIG. 19). In every case, except 3tsp, the AtS1 and AtS3 expression cassettes confer embryo-specific GUS accumulation in the temporal manner expected (see FIG. 1). GUS levels are barely detectable in pre-torpedo stage embryos. GUS activity rapidly rises during the cotyledon stage and remains stable in the dry seed.

Figure 19B:
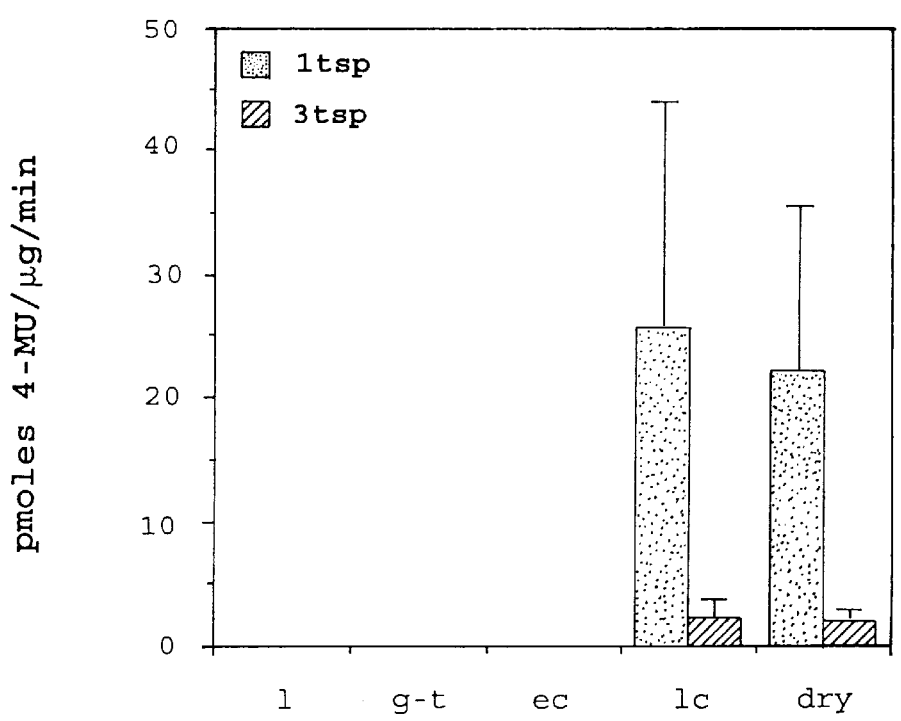
FIG. 19B graphically depicts developmental expression of the AtS1 and AtS3 translational fusions, 1tlp and 3tlp in transgenic Arabidopsis. Abbreviations are as in FIG. 19A. Each tissue sample was assayed in triplicate and the data represents the mean between individual plants.
Figure 20A:
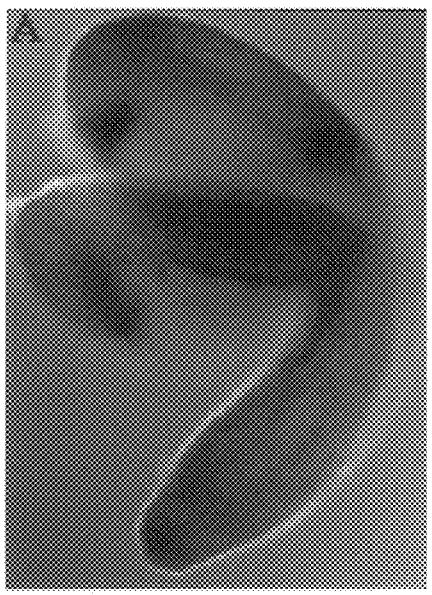
FIG. 20A shows histochemical localization of GUS activity in a mature Arabidopsis embryo from a 1tsp transgenic line.
Figure 20B:
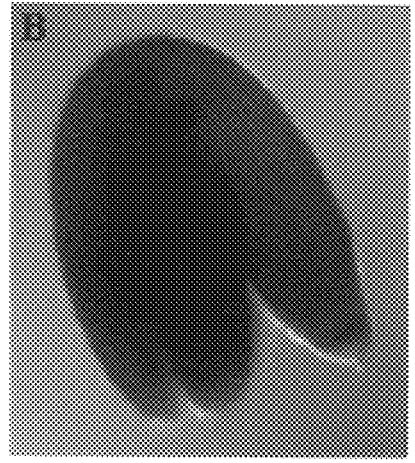
FIG. 20B shows histochemical localization of GUS activity in a mature Arabidopsis embryo from a 1tlp transgenic line.
Figure 20C:
FIG. 20C shows histochemical localization of GUS activity in a mature Arabidopsis embryo from a 3tsp transgenic line.
Figure 20D:
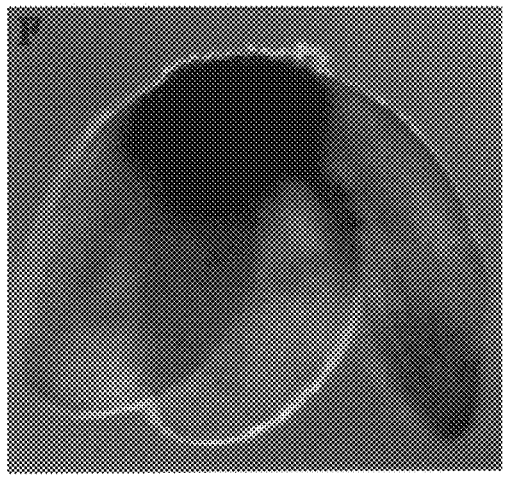
FIG. 20D shows histochemical localization of GUS activity in a mature Arabidopsis embryo from a 3tlp transgenic line.

The data presented in FIGS. 19A and 19B demonstrate that elements lying upstream of the AtS1 and AtS3 coding sequence are capable of driving embryo-specific accumulation of GUS activity in transgenic Arabidopsis. However, the 3tsp expression cassette does not lead to the accumulation of significant GUS activity whereas 1tsp does (FIGS. 19B, 20A, 20C and Table 3). Including the promoter's respective 5'-UTR in each expression cassette significantly enhances embryo-specific GUS accumulation (FIGS. 19, 20B and 20D). The mechanism by which this effect manifests itself may differ between AtS1 and AtS3. It seems clear that the AtS1 5'-UTR has a significant synergistic effect on overall promoter activity.

Figure 21A:
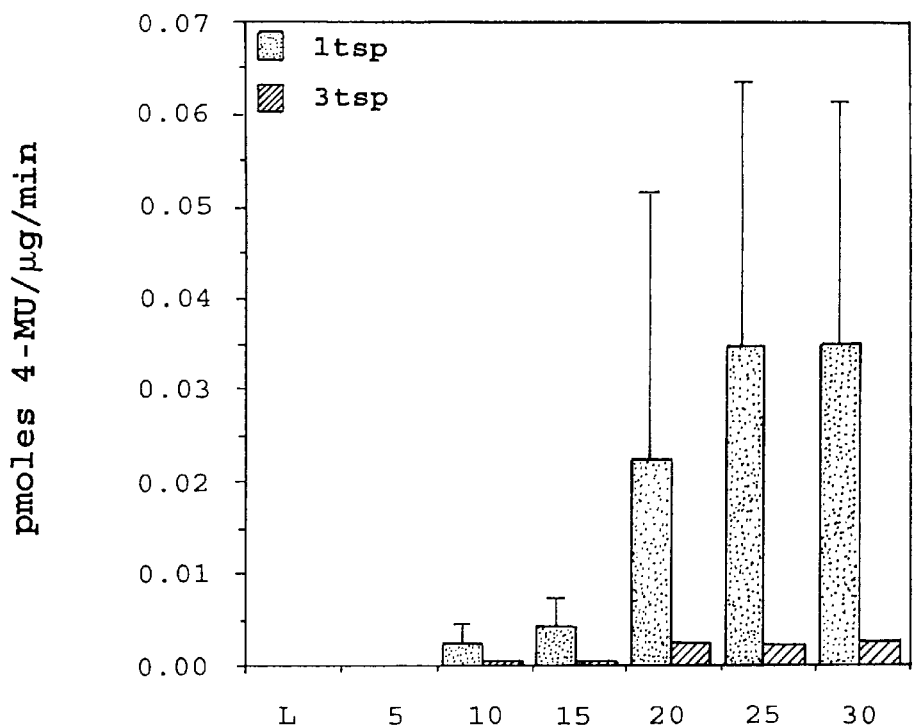
FIG. 21A graphically depicts developmental expression of the AtS1 and AtS3 transcriptional promoter:GUS fusions in transgenic tobacco. "L" denotes leaf tissue; the remaining bars denote developing seeds representing 5, 10, 15, 20, 25 and 30 days post flowering (DPF). Each tissue sample was assayed in triplicate and the data represents the mean between individual plants. The data represents the average of at least two individuals.
Figure 21B:
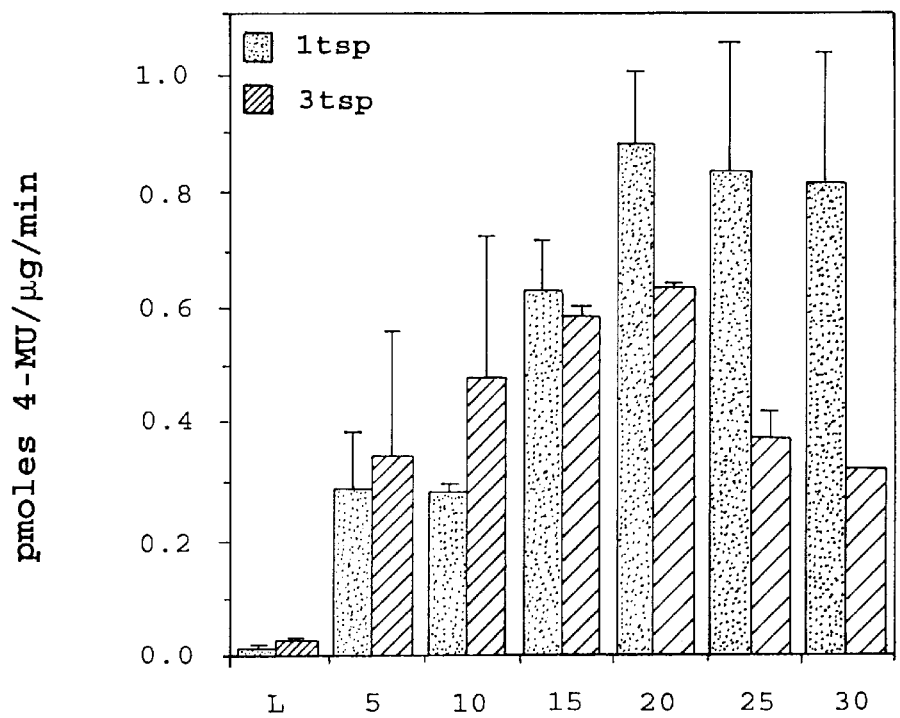
FIG. 21B graphically depicts developmental expression of the AtS1 and AtS3 translational promoter:GUS fusions in transgenic tobacco. "L" denotes leaf tissue; the remaining bars denote developing seeds representing 5, 10, 15, 20, 25 and 30 days post flowering (DPF). Each tissue sample was assayed in triplicate and the data represents the mean between individual plants. The data represents the average of at least two individuals.
Figure 22A:
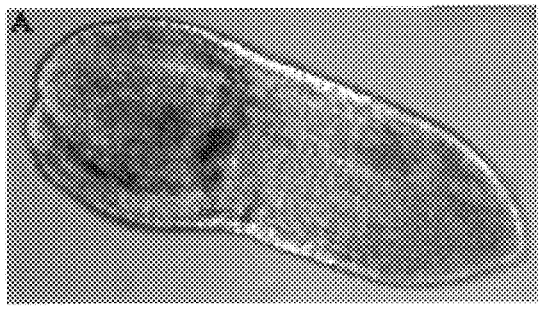
FIG. 22A shows histochemical localization of GUS activity in a mature tobacco embryo from a 1tsp transgenic line.
Figure 22B:
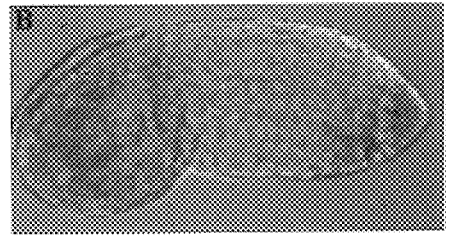
FIG. 22B shows histochemical localization of GUS activity in a mature tobacco embryo from a 1tlp transgenic line.
Figure 22C:
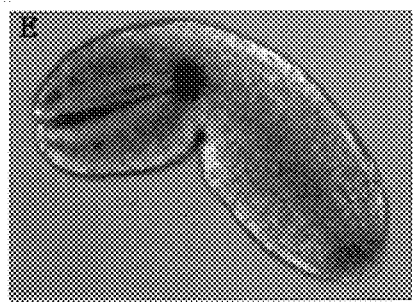
FIG. 22C shows histochemical localization of GUS activity in a mature tobacco embryo from a 3tsp transgenic line.
Figure 22D:
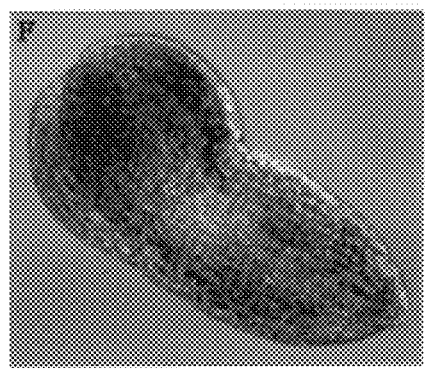
FIG. 22D shows histochemical localization of GUS activity in a mature tobacco embryo from a 3tlp transgenic line.

The native AtS1 promoter (1tsp) is sufficient to confer seed-specific accumulation of GUS activity in both transgenic Arabidopsis and transgenic tobacco (FIGS. 22A through 22D). The 1tsp construct is approximately 55-fold less effective in tobacco when compared to Arabidopsis. Addition of the AtS1 5'UTR (1tlp) enhances GUS accumulation up to 23-fold over that of 1tsp (FIG. 21B, Table 4). This data indicates that 1tlp is about 28-fold less effective in tobacco.

TABLE 3

COMPARISON OF GUS ACTIVITY LEVELS DRIVEN BY AtS1- AND AtS3- BASED EXPRESSION CASSETTES IN TRANSGENIC ARABIDOPSIS

| | GUS ACTIVITY[a] | |
|---|---|---|
| Construct | Dry Seed | Leaf |
| 1 tsp | 1.9 ± 1.0 | 0.003 ± 0.006 |
| 1 tlp | 22 ± 13 | 0.019 ± 0.027 |
| 3 tsp | 0.015 ± 0.024 | 0.003 ± 0.005 |
| 3 tlp | 1.9 ± 1.0 | 0.014 ± 0.036 |

[a]Reported as pmoles 4-MU/µg/minute.

TABLE 4

COMPARISON OF GUS ACTIVITY LEVELS DRIVEN BY AtS1 - AND AtS3 - BASED EXPRESSION CASSETTES IN TRANSGENIC TOBACCO

| | GUS ACTIVITY[a] | |
|---|---|---|
| Construct | Dry Seed | Leaf |
| 1 tsp | 0.035 ± 0.026 | 0.0 ± 0.0 |
| 1 tlp | 0.81 ± .23 | 0.015 ± 0.007 |
| 3 tsp | 0.002 ± 0.002 | 0.0 ± 0.0 |
| 3 tlp | 0.32 ± 0.005 | 0.025 ± 0.012 |

[a]Reported as pmoles 4-MU/µg/minute.

What is claimed is:

1. An isolated nucleic acid corresponding to an AtS1 5' regulatory region which directs seed-specific expression comprising the nucleotide sequence set forth in SEQ ID NO:27.

2. An isolated nucleic acid corresponding to an AtS1 promoter which directs seed specific expression comprising the nucleotide sequence set forth in SEQ ID NO:23.

3. An isolated nucleic acid corresponding to an AtS1 5' transcribed and untranslated region comprising the nucleotide sequence set forth in SEQ ID NO:25.

4. An isolated nucleic acid corresponding to an AtS3 5' regulatory region which directs seed-specific expression comprising the nucleotide sequence set forth in SEQ ID NO:28.

5. An isolated nucleic acid corresponding to an AtS3 promoter comprising the nucleotide sequence set forth in SEQ ID NO:24.

6. An isolated nucleic acid corresponding to an AtS3 5' transcribed and untranslated region comprising the nucleotide sequence set forth in SEQ ID NO:26.

7. A plant transformation vector which comprises at least one nucleic acid of any one of claims 1–6.

8. A plant cell comprising a nucleic acid of any one of claims 1–6, said nucleic acid being heterologous to said plant cell.

9. A plant, or progeny of said plant, which has been regenerated from the plant cell of claim 8.

10. A transgenic plant, or progeny of said plant, comprising a nucleic acid of any one of claims 1–6.

11. The plant of claim 9 wherein said plant is a cotton, tobacco, oil seed rape, maize or soybean plant.

12. The plant of claim 10 wherein said plant is a cotton, tobacco, oil seed rape, maize or soybean plant.

13. An expression cassette which comprises at least one AtS1 5' regulatory region of claim 1 operably linked to at least one of a nucleic acid encoding a heterologous gene or a nucleic acid encoding a sequence complementary to a native plant gene.

14. An expression cassette which comprises at least one AtS1 5' promoter of claim 2 operably linked to at least one of a nucleic acid encoding a heterologous gene or a nucleic acid encoding a sequence complementary to a native plant gene.

15. An expression cassette which comprises at least one AtS1 5' transcribed and untranslated region of claim 3 operably linked at its 5' end to a promoter which functions in plants and operably linked at its 3' end to at least one of a nucleic acid encoding a heterologous gene or a nucleic acid encoding a sequence complementary to a native plant gene.

16. An expression cassette which comprises at least one AtS3 5' regulatory region of claim 4 operably linked to at least one of a nucleic acid encoding a heterologous gene or a nucleic acid encoding a sequence complementary to a native plant gene.

17. An expression cassette which comprises at least one AtS3 promoter of claim 5 operably linked to at least one of a nucleic acid encoding a heterologous gene or a nucleic acid encoding a sequence complementary to a native plant gene.

18. An expression cassette which comprises at least one AtS3 5' transcribed and untranslated region of claim 6 operably linked at its 5' end to a promoter which functions in plants and operably linked at its 3' end to at least one of a nucleic acid encoding a heterologous gene or a nucleic acid encoding a sequence complementary to a native plant gene.

19. The expression cassette of any one of claims 13–18 wherein the heterologous gene is at least one of a fatty acid synthesis gene or a lipid metabolism gene.

20. The expression cassette of claim 19 wherein the heterologous gene is selected from the group consisting of an acetyl-coA carboxylase gene, a ketoacyl synthase gene, a malonyl transacylase gene, a lipid desaturase gene, an acyl carrier protein (ACP) gene, a thioesterase gene, an acetyl transacylase gene, and an elongase gene.

21. The expression cassette of claim 19 wherein the lipid desaturase gene is selected from the group consisting of a Δ6-desaturase gene, a Δ12-desaturase gene, and a Δ15-desaturase gene.

22. An expression vector which comprises the expression cassette of any one of claims 13–18.

23. A cell comprising the expression cassette of any one of claims 13–18.

24. A cell comprising the expression vector of claim 22.

25. The cell of claim 23 wherein said cell is a bacterial cell or a plant cell.

26. The cell of claim 24 wherein said cell is a bacterial cell or a plant cell.

27. A transgenic plant comprising the expression cassette of any one of claims 13–18.

28. A transgenic plant comprising the expression vector of claim 24.

29. A plant which has been regenerated from the plant cell of claim 25.

30. A plant which has been regenerated from the plant cell of claim 24.

31. The plant of claim 28 wherein said plant is a sunflower, soybean, maize, cotton, tobacco, peanut, oil seed rape or Arabidopisis plant.

32. The plant of claim 29 wherein said plant is a sunflower, soybean, maize, cotton, tobacco, peanut, oil seed rape or Arabidopisis plant.

33. Progeny of the plant of claim 27.

34. Progeny of the plant of claim 28.

35. Seed from the plant of claim 27.

36. Seed from the plant of claim 28.

37. An expression vector which comprises the expression cassette of claim 19.

38. A cell comprising the expression cassette of claim 19.

39. A transgenic plant comprising the expression cassette of claim 19.

40. An expression vector which comprises the expression cassette of claim 20.

41. A cell comprising the expression cassette of claim 20.

42. A transgenic plant comprising the expression cassette of claim 20.

43. An expression vector which comprises the expression cassette of claim 21.

44. A cell comprising the expression cassette of claim 21.

45. A transgenic plant comprising the expression cassette of claim 21.

* * * * *

SEQUENCE LISTING (1) GENERAL INFORMATION:

(iii) NUMBER OF SEQUENCES: 42

(2) INFORMATION FOR SEQ ID NO:1:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:1:

TTGCAGCTCT AAAGAAAA                                                    18

(2) INFORMATION FOR SEQ ID NO:2:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

TTGCAGCTCT AAAGAAAAGC TTCTGTA                                          27

(2) INFORMATION FOR SEQ ID NO:3:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

TTGCAGCTCT AAAGAAAAGC TTCTGTATGT TTT                                   33

(2) INFORMATION FOR SEQ ID NO:4:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

TTGCAGCTCT AAAGAAAAGC TTCTGTATGT TTTGTTGCC                             39

(2) INFORMATION FOR SEQ ID NO:5:

(i) SEQUENCE CHARACTERISTICS:
        (A) LENGTH: 110 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

TTGCAGCTCT AAAGAAAAGC TTCTGTATGT TTTGTTGCCT TGGTCTCTCT TTGTACCAAC      60

CCCTTTTTCT GTTATTTCCA ATTTTACACT GTTAGTTATT ATTGCTAAAT                110

(2) INFORMATION FOR SEQ ID NO:6:

(i) SEQUENCE CHARACTERISTICS:
        (A) LENGTH: 129 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

```
TTGCAGCTCT AAAGAAAAGC TTCTGTATGT TTTGTTGCCT TGGTCTCTCT TTGTACCAAC        60

CCCTTTTTCT GTTATTTCCA ATTTTACACT GTTAGTTATT ATTGCTAAAT TTATTACTGA       120

CTTACTCTA                                                               129

(2) INFORMATION FOR SEQ ID NO:7:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

TTACTTATTC AAGTA                                                         15

(2) INFORMATION FOR SEQ ID NO:8:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

TTACTTATTC AAGTATGTGC GCATGA                                             26

(2) INFORMATION FOR SEQ ID NO:9:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

TTACTTATTC AAGTATGTGC GCATGAGTTC CTGT                                    34

(2) INFORMATION FOR SEQ ID NO:10:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

TTACTTATTC AAGTATGTGC GCATGAGTTC CTGTTA                                  36

(2) INFORMATION FOR SEQ ID NO:11:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:
```

```
TTACTTATTC AAGTATGTGC GCATGAGTTC CTGTTAGCTA TGA                      43
```

(2) INFORMATION FOR SEQ ID NO:12:

(i) SEQUENCE CHARACTERISTICS:
        (A) LENGTH: 67 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

```
TTACTTATTC AAGTATGTGC GCATGAGTTC CTGTTAGCTA TGATTATTAA ATCAGTTGGT    60

ACCGACA                                                              67
```

(2) INFORMATION FOR SEQ ID NO:13:

(i) SEQUENCE CHARACTERISTICS:
        (A) LENGTH: 2310 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

```
CGAATTACTG AATTTAGCAG ACAAGAATAG AAAGAGTGAT GAAACATGGA AGAAAACGTG    60

TCTCTAGAGT CATGTCAAGT GTAAGACAGA GGAAGAGAGA AGAGATGTGC GTCAAAGACA   120

AGGAAAGAGA GATGTCAATC GCTGCTTTCG TCGGCGCGTG CATGTCCGCC ACGCACATCA   180

ATCAAATCGA TCTTATTATT ATTACCTCAT TATACTCTTT ACTCTAAGAC AAACACATAC   240

ATTTGCACTC AGTCTAGAGA CAAAGAGAGA GAGAGATGGG GTCAAAGACG AGATGATGG    300

AGAGAGACGC AATGGCTACG GTGGCTCCCT ATGCGCCGGT CACTTACCAT CGCCGTGCTC   360

GTGTTGACTT GGATGATAGA CTTCCTAAAC CTTGTAAACC TGTCTCTCGC TACTTGCATT   420

TTTTTATCCC TAATTGATTT CAATATATTG CATGCCAAAA AACATTTGAT ATATGGTTGA   480

ATTTAAGAAA CCCTTTTAAA TATATGGAAT TGCCGACCCT CAAAATTTTT AAAACATGCA   540

TATAGAATGA TGTTCATGAT CTTATAGAAG CTATAAATTG TAAAATGATA CATATCCTGT   600

ATATGATGGT AATTAATAAT GTATTACCCA TGAACGTGCA TGAATAATTC TATACACACA   660

TTACACATAC GTGGAAATGA TACAGATTTT GACTTATATG TGTTATGCAT AGATATGCCA   720

AGAGCATTGC AAGCACCAGA CAGAGAACAC CCGTACGGAA CTCCAGGCCA TAAGAATTAC   780

GGACTTAGTG TTCTTCAACA GCATGTCTCC TTCTTCGATA TCGATGATAA TGGCATCATT   840

TACCCTTGGG AGACCTACTC TGGTATGTCT ATATAGTATA TATAGATATT TCAACTTCAA   900

ATTTTTCGTT AGTATTATAT GTACAAAAAG TTGATCCCAA CCGGTGATTA GGACTGCGAA   960

TGCTTGGTTT CAATATCATT GGGTCGCTTA TAATAGCCGC TGTTATCAAC CTGACCCTTA  1020

GCTATGCCAC TCTTCCGGTA ACACCTCTCC TCCTCTGCTG ACATATATCG CAAAACTTTG  1080

ATTGATTCTA CTCTAGACTC GGAAATTATC ATATCCAAAT CCGTTGTCCA TTTTGTTAGT  1140

GTTCTACTTG ATTATATGCA GGGGTGGTTA CCTTCACCTT TCTTCCCTAT ATACATACAC  1200

AACATACACA AGTCAAAGCA TGGAAGTGAT TCAAAAACAT ATGACAATGA AGGAAGGTGA  1260

GTGACCATAT TATCTTGAAA AAAACGGTTG ACTGATAGAA AATATGATGA CTGATGCATA  1320

TGGTATAACT TCCGTATGCT TTTCAGGTTT ATGCCGGTGA ATCTTGAGTT GATATTTAGC  1380
```

-continued

```
AAATATGCGA AAACCTTGCC AGACAAGTTG AGTCTTGGAG AACTATGGGA GATGACAGAA      1440

GGAAACCGTG ACGCTTGGGA CATTTTTGGA TGGTACAATC ACAGCATTAG CCTTCCTTTT      1500

TCTTACCCTT TCATTAGTTT ATTGAATGCA TGTGTTAAAC TAAAGTATTA GTCAATGTTG      1560

TTGTAGTTAT AATGTTTGGA TCTACATGTA TGTATTAGGA TCGCAGGCAA AATAGAGTGG      1620

GGACTGTTGT ACTTGCTAGC AAGGGATGAA GAAGGGTTTT TGTCAAAAGA AGCTATTAGG      1680

CGGTGTTTCG ATGGAAGCTT GTTCGAGTAC TGTGCCAAAA TCTACGCTGG TATCAGTGAA      1740

GACAAGACAG CATACTACTA AAAGTATCCT TTATGTTAAG TAATTGATCG AGCCATTTTA      1800

AGCTAATAAT CGCTCAATGT GAAGCTTGTG CCTATACGGT AAATGAAGGT TCGGGTAGTA      1860

GTATGGACTT TTGGTCTAAG AGATCTATGT TTGTTTTTGT TTTTCCAGTT CTGTATGGTT      1920

ATACTATAAG TTGCAGCTCT AAAGAAAAGC TTCTGTATGT TTTGTTGCCT TGGTCTCTCT      1980

TTGTACCAAC CCCTTTTTCT GTTATTTCCA ATTTTACACT GTTAGTTATT ATTGCTAAAT      2040

TTATTACTGA CTTACTCTAT AGTAGTGTAA CGAATATATG GTCACATTAA CTCAAAGTTA      2100

ACTCCACTCC ATGAACATTG AAGCACTGAG AATCCAGGAC CTATGAATCA ACGCAATCAA      2160

AGAAAGAGAA AGTTAGTAAC ACCTTCATGA AGGAGAGTCT TAAAAGAAAA GAAGAAAAGA      2220

TTAAAACACC TTCATGAAAG AGAGTCTTGA ACTTGAATAG TATACTAGTC CTTTTAGAGT      2280

CTTGAAGTTT GAATAGTATA CTAGTTCTTT                                      2310

(2) INFORMATION FOR SEQ ID NO:14:

(i) SEQUENCE CHARACTERISTICS:
        (A) LENGTH: 2310 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

AAAATGTAAG AAGGAATAGT ACAATATAGA ACGGTAAAAA AAATGGCAAA CCATTTACTT        60

CAATAAGAAA GGTTAGCAAC CACACTCAGC AAATGGGACA CATAGGATCC GACGTGGTTT       120

ATATTATAGT AGTCTGATAT TGTAGAGTCA ATGGGTATAT TTGTCTTTTT CAAAGACTCA       180

GTTCCATTGA AGCGTAGGTT ACTTCTTTAA ACAAGACTCT GTTTTGAATG ATATTGTAAA       240

GTTAAGGGGT ACGTTTGTCT TTTTCAGGAC AAAGCGAGAC CATAGATGAC GTGTCAACTG       300

CTAATTTTCA AAAACTCGGT CTACAAACCA TAAGGAAACT TATTTATTCA ATTATTTCCG       360

TCAAAAAAAT ATAATTTTCT TTTTGCATCT CAATGGATTG ATTCCATGTG CCAAGTGTTG       420

GTGTTCATGA GAAAATTAGT CGCAGCTGAT GACAACAAAC ATCAAGCATT TATAATTTAT       480

ATAACACTCA CGAGTGCCTC TTTCTTTATC TACCTCGTCT CCTAATCACA AACACACACA       540

AATCTCTGAA GTAAAATGAC GTTCCCTTCT CTTTCTGTCT CATTTCTCTT CTTTGCCTTC       600

ATATTCGTTA CGCATGCATT CGACCTCAGC ATCATCCAGG TTCTTCTTGT TTTCTACTTT       660

CTGGCTAACA AAGTAACCAG AACCGGTTTT CTCACTTGTA TATTTGTTTT TTTGAGAAAA       720

TCATGTAGAT GCAACAGGGA ACATGTCCGT ACACGGTGGT TGTCATGACA AGCTGTCTTT       780

CTCCGGAGTC GACAAGAGAT CAGATCAGCA TTGTTTTTGG CGATGCCGAC GGTAACAAGG       840

TTAAGTAACT AGATTTTTTT GTATATAGTT CCAGTTAAGT CGACATCTTT ATTTGCTTTA       900

AAGTGGTTTA GATACCTTGC ATGCATGCAT GTGTGCTCAA TACAAGTAAC TTCTTAGTGA       960

TTTAAATAAA ATGTTAAATA TATATCTTTT TGTTTTAGGT GTATGCACCG AAACTAGGGG      1020
```

-continued

```
GTTCGGTAAG AGGACCAGGG GGTTTGGGAA AGTGTTCAAC GAACACATTC CAAGTCAGAG      1080

GTCAATGTTT AAATGACCCT ATCTGCTCTC TCTATATCAA CCGGAATGGA CCCGATGGCT      1140

GGGTCCCGGA GTCCATTGAG ATCTACTCAG AAGGTTCAAA GTCCGTTAAA TTCGATTTCA      1200

GCAAGAGCGT CCCTCAACTA AACACTTGGT ACGGCCACAA CAACTGCAAC ACCACAGGCA      1260

GACCATCGTC TCCCGATCTG CCTCCACCGC ATTTTCCGCC AGAGTTTCCA CCGGAGACAC      1320

CTACCACCCC ACCGCCGCCT CCACCAAGGC CGTCTGCTGC TTCAAGGCTT GGAAATGGTG      1380

AGAGTGTTTT CCTTGCGTTT GCCATTGCGA CTGCGATTGC CGCAATGGTG CGTTGGAGTT      1440

ACTAGCATGG TACTTGAAGA GCATGTTGTT GGGTTGTATG AGGCTTTTTC TTTCCGTCGA      1500

ATGTTTTTAT TTGCTTTCGT TTTGCTTCAG CCTTTTCCTT GTTGTAGAAA ACATAATTAC      1560

TTATTCAAGT ATGTGCGCAT GAGTTCCTGT TTAGCTATGA TTATTAATCA GTTGGTACCG      1620

ACATTTAGTA GTTCATTTTC AAAAGAGAAT CCATCACTTG TGCATAGAAA TAAAGATTAA      1680

AAAAATCCAT CACTTTCCAT AACCGGTGTT TGGACTTGCA ATTTTTTAGC GAGACAGTAT      1740

GATAATTTTT TTTTAAAGT ACATATATGC TAATCAGTGA TCCAATTTTT AACAATTGAG       1800

ATGAAGATTT ATCCAAAAAC TGGTGTATCA TACCAAATTA TCAATAGATT ATATTGAGAC      1860

AAACAAGGAT ATAATTTAAA TAATTTGGAC AACAAACCTC AACTCAAGGC ACATTTGATG      1920

ACATTTCAAG GAAACATAA ATGGACCTAA CTTTTGATTC GAATTGTTAT TGAAGTGTTG       1980

TCGAAAACTG GAATGCATGG AATTTGTCAG GTAGTAGTAG GTGGAGTTCA TGGGAGAAGT      2040

CGAAACACGT AAACAACTCT TCTCTTTTAG ACAAATTTCT TCTTTTTTCG GACATCTGGT     2100

TTCACGTGTC CTTGACCTAA AATCGGGATT AAATATGGCT TATATTGATG TTACACCGAG      2160

CCATTTTCAT TTTCTTTTAC TTAAATCAAA TTGTCTATTG ATGTTAATCC GACAATTTTT     2220

ATTTTATTTT ACTGATTTTG TTTTTGAGAT GTTGTTCTTT TAAGTCACCA TAAAATTAAA     2280

AAAAAAAAAA AAAAGAGAG AGAGAAGGTA                                       2310
```

(2) INFORMATION FOR SEQ ID NO:15:

(i) SEQUENCE CHARACTERISTICS:
        (A) LENGTH: 735 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

```
ATGGGGTCAA AGACGGAGAT GATGGAGAGA GACGCAATGG CTACGGTGGC TCCCTATGCG       60

CCGGTCACTT ACCATCGCCG TGCTCGTGTT GACTTGGATG ATAGACTTCC TAAACCTTAT      120

ATGCCAAGAG CATTGCAAGC ACCAGACAGA GAACACCCGT ACGGAACTCC AGGCCATAAG      180

AATTACGGAC TTAGTGTTCT TCAACAGCAT GTCTCCTTCT TCGATATCGA TGATAATGGC      240

ATCATTTACC CTTGGGAGAC CTACTCTGGA CTGCGAATGC TTGGTTTCAA TATCATTGGG      300

TCGCTTATAA TAGCCGCTGT TATCAACCTG ACCCTTAGCT ATGCCACTCT TCCGGGGTGG      360

TTACCTTCAC CTTTCTTCCC TATATACATA CACAACATAC ACAAGTCAAA GCATGGAAGT      420

GATTCAAAAA CATATGACAA TGAAGGAAGG TTTATGCCGG TGAATCTTGA GTTGATATTT      480

AGCAAATATG CGAAAACCTT GCCAGACAAG TTGAGTCTTG AGAACTATG GGAGATGACA       540

GAAGGAAACC GTGACGCTTG GACATTTTT GGATGGATCG CAGGCAAAAT AGAGTGGGGA       600

CTGTTGTACT TGCTAGCAAG GGATGAAGAA GGGTTTTTGT CAAAAGAAGC TATTAGGCGG      660
```

TGTTTCGATG GAAGCTTGTT CGAGTACTGT GCCAAAATCT ACGCTGGTAT CAGTGAAGAC    720

AAGACAGCAT ACTAC    735

(2) INFORMATION FOR SEQ ID NO:16:

(i) SEQUENCE CHARACTERISTICS:
        (A) LENGTH: 732 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

ATGGCGGAGG AGGCGGCTAG CAAGGCAGCG CCGACCGATG CGCTGTCGTC CGTGGCGGCG    60

GAGGCGCCGG TGACGAGAGA ACGGCCGGTC CGAGCGGACT TGGAAGTGCA GATTCCGAAG    120

CCCTATTTGG CCCGAGCTCT GGTTGCTCCG GACGTGTACC ATCCTGAAGG AACCGAGGGG    180

CGTGACCACC GGCAGATGAG TGTGCTGCAG CAGCATGTGG CTTTCTTCGA CCTGGATGGC    240

GACGGTATCG TTTATCCATG GGAAACTTAT GGAGGACTAC GGGAATTGGG CTTCAACGTG    300

ATTGTTTCGT TCTTTTTGGC GATAGCCATA AACGTTGGTC TAAGCTACCC AACTCTGCCA    360

AGCTGGATAC CATCTCTCCT GTTCCCTATA CACATAAAAA ACATCCACAG GCTAAGCAC    420

GGCAGCGATA GCTCGACGTA CGACAACGAG GGAAGGTTTA TGCCGGTCAA TTTCGAGAGC    480

ATCTTCAGCA GAACGCCCG CACGGCGCCG ACAAGCTCA CGTTCGGCGA TATCTGGCGG    540

ATGACCGAAG GCCAAAGGGT GGCGCTCGAC TTGCTTGGGA GGATCGCGAG TAAGGGGGAG    600

TGGATATTGC TCTACGTGCT TGCGAAAGAT GAGGAAGGAT TCCTCAGGAA GGAGGCTGTT    660

CGCCGCTGCT TCGATGGGAG CCTATTCGAG TCGATTGCCC AGCAGAGAAG GGAGGCACAT    720

GAGAAGCAGA AG    732

(2) INFORMATION FOR SEQ ID NO:17:

(i) SEQUENCE CHARACTERISTICS:
        (A) LENGTH: 222 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:17:

Asp Ala Met Ala Thr Val Ala Pro Tyr Ala Pro Val Thr Tyr His Arg
1               5                   10                  15

Arg Ala Arg Val Asp Leu Asp Asp Arg Leu Pro Lys Pro Tyr Met Pro
            20                  25                  30

Arg Ala Leu Gln Ala Pro Asp Arg Glu His Pro Tyr Gly Thr Pro Gly
        35                  40                  45

His Lys Asn Tyr Gly Leu Ser Val Leu Gln Gln His Val Ser Phe Phe
    50                  55                  60

Asp Ile Asp Asp Asn Gly Ile Ile Tyr Pro Trp Glu Thr Tyr Ser Gly
65                  70                  75                  80

Leu Arg Met Leu Gly Phe Asn Ile Ile Gly Ser Leu Ile Ala Ala
                85                  90                  95

Val Ile Asn Leu Thr Leu Ser Tyr Ala Thr Leu Pro Gly Trp Leu Pro
                100                 105                 110

Ser Pro Phe Phe Pro Ile Tyr Ile His Asn Ile His Lys Ser Lys His
            115                 120                 125

```
Gly Ser Asp Ser Lys Thr Tyr Asp Asn Glu Gly Arg Phe Met Pro Val
    130                 135                 140

Asn Leu Glu Leu Ile Phe Ser Lys Tyr Ala Lys Thr Leu Pro Asp Lys
145                 150                 155                 160

Leu Ser Leu Gly Glu Leu Trp Glu Met Thr Glu Gly Asn Arg Asp Ala
                165                 170                 175

Trp Asp Ile Phe Gly Trp Ile Ala Gly Lys Ile Glu Trp Gly Leu Leu
                180                 185                 190

Tyr Leu Leu Ala Arg Asp Glu Gly Phe Leu Ser Lys Glu Ala Ile
                195                 200                 205

Arg Arg Cys Phe Asp Gly Ser Leu Phe Glu Tyr Cys Ala Lys
    210                 215                 220
```

(2) INFORMATION FOR SEQ ID NO:18:

(i) SEQUENCE CHARACTERISTICS:
        (A) LENGTH: 222 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:18:

```
Asp Ala Leu Ser Ser Val Ala Ala Glu Ala Pro Val Thr Arg Glu Arg
1               5                   10                  15

Pro Val Arg Ala Asp Leu Glu Val Gln Ile Pro Lys Pro Tyr Leu Ala
                20                  25                  30

Arg Ala Leu Val Ala Pro Asp Val Tyr His Pro Glu Gly Thr Glu Gly
                35                  40                  45

Arg Asp His Arg Gln Met Ser Val Leu Gln Gln His Val Ala Phe Phe
    50                  55                  60

Asp Leu Asp Gly Asp Gly Ile Val Tyr Pro Trp Glu Thr Tyr Gly Gly
65                  70                  75                  80

Leu Arg Glu Leu Gly Phe Asn Val Ile Val Ser Phe Phe Leu Ala Ile
                85                  90                  95

Ala Ile Asn Val Gly Leu Ser Tyr Pro Thr Leu Pro Ser Trp Ile Pro
                100                 105                 110

Ser Leu Leu Phe Pro Ile His Ile Lys Asn Ile His Arg Ala Lys His
                115                 120                 125

Gly Ser Asp Ser Ser Thr Tyr Asp Asn Glu Gly Arg Phe Met Pro Val
    130                 135                 140

Asn Phe Glu Ser Ile Phe Ser Lys Asn Ala Arg Thr Ala Pro Asp Lys
145                 150                 155                 160

Leu Thr Phe Gly Asp Ile Trp Arg Met Thr Glu Gly Gln Arg Val Ala
                165                 170                 175

Leu Asp Leu Leu Gly Arg Ile Ala Ser Lys Gly Glu Trp Ile Leu Leu
                180                 185                 190

Tyr Val Leu Ala Lys Asp Glu Glu Gly Phe Leu Arg Lys Glu Ala Val
                195                 200                 205

Arg Arg Cys Phe Asp Gly Ser Leu Phe Glu Ser Ile Ala Gln
    210                 215                 220
```

(2) INFORMATION FOR SEQ ID NO:19:

(i) SEQUENCE CHARACTERISTICS:
        (A) LENGTH: 256 base pairs (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:19:

TTCTTCAACA GCATGTCTCC TTCTTCGATA TCGATGATAA TGGCATCATT TACCCTTGGG      60

AGACCTACTC TGGACTGCGA ATGCTTGGTT TCAATATCAT TGGGTCGCTT ATAATAGCCG     120

CTGTTATCAA CCTGACCCTT AGCTATGCCA CTCTTCCGGG GTGGTTACCT TCACCTTTCT     180

TCCCTATATA CATACACAAC ATACACAAGT CAAAGCATGG AAGTGATTCA AAAACATATG     240

ACAATGAAGG AAGGTT                                                     256

(2) INFORMATION FOR SEQ ID NO:20:

(i) SEQUENCE CHARACTERISTICS:
            (A) LENGTH: 257 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:20:

TTCTTGCAGA GACATGTCGC TTTTTTCGAT AGGAACAAAG ATGGTATCGT TTATCCCTCG      60

GAGACATTTC AAGGATTTAG AGCAATTGGG TGTGGATATT TGTTGTCAGC AGTCGCTTCT     120

GTGTTCATAA ACATAGGTCT CAGCAGCAAA ACTCGTCCGG GTAAAGGATT CTCTATCTGG     180

TTTCCTATAG AGGTTAAGAA TATTCACCTT GCCAAACACG GAAGCGATTC AGGCGTTTAC     240

GACAAAGATG GACGGTT                                                    257

(2) INFORMATION FOR SEQ ID NO:21:

(i) SEQUENCE CHARACTERISTICS:
            (A) LENGTH: 273 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:21:

CCACCGGCAG ATGAGTGTGC TGCAGCAGCA TGTGGCTTTC TTCGACCTGG ATGGCGACGG      60

TATCGTTTAT CCATGGGAAA CTTATGGAGG ACTACGGGAA TTGGGCTTCA ACGTGATTGT     120

TTCGTTCTTT TTGGCGATAG CCATAAACGT TGGTCTAAGC TACCCAACTC TGCCAAGCTG     180

GATACCATCT CTCCTGTTCC CTATACACAT AAAAAACATC CACAGGGCTA AGCACGGCAG     240

CGATAGCTCG ACGTACGACA ACGAGGGAAG GTT                                  273

(2) INFORMATION FOR SEQ ID NO:22:

(i) SEQUENCE CHARACTERISTICS:
            (A) LENGTH: 272 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:22:

CCAGAAGAAG ATAATTTCTT GCAGAGACAT GTCGCTTTTT TCGATAGGAA CAAAGATGGT      60

```
ATCGTTTATC CCTCGGAGAC ATTTCAAGGA TTTAGAGCAA TTGGGTGTGG ATATTTGTTG      120

TCAGCAGTCG CTTCTGTGTT CATAAACATA GGTCTCAGCA GCAAAACTCG TCCGGGTAAA      180

GGATTCTCTA TCTGGTTTCC TATAGAGGTT AAGAATATTC ACCTTGCCAA ACACGGAAGC      240

GATTCAGGCG TTTACGACAA AGATGGACGG TT                                    272
```

(2) INFORMATION FOR SEQ ID NO:23:

(i) SEQUENCE CHARACTERISTICS:
        (A) LENGTH: 1211 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:23:

```
CGATCCACCC CATGACTCGA ATGATGACTC CAGCCACCAT CAATTCCCTG AAGTGCCACA       60

ACACCCTCTA CCTCCCAGGT TTTATGACAA TCCGACCAAC GATTATCCCG CAGATGTCCC      120

ACCTCCACCA CCGTCTTCTT ACCCTTCCAA CGATCATCTT CCCCCTCCCA CAGGACCATC      180

AGACTCCCCT TACCCGCATC CTTACAGTCA TCAACCATAC CACCAAGACC CGCCAAAACA      240

CATGCCGCCA CCGCAAAACT ACTCATCTCA TGAGCCTTCT CCAAATTCTC TCCCTAATTT      300

CCAATCTTAT CCTAGCTTTA GTGAGAGCAG CCTCCCATCC ACTTCTCCCC ACTACCCTTC      360

TCACTACCAA AACCCAGAAC CTTACTATTC TTCTCCGCAC TCTGCACCTG CTCCTTCTTC      420

CACAAGCTTC TGCTCTGCTC CTCCTCCTCC ACCTTACTCA TCAAACGGGC GTATCAATAT      480

TGCTCCCGTG CTAGATCCTG CACCGAGTTC AGCTCAGAAG TACCATTACG ATAGCAGCTA      540

CCAGCCAGGG CCTGAGAAGG TTGCAGAGGC ACTCAAGGCT GCTAGATTCG CTGTGGGAGC      600

TTTGGCTTTT GATGAAGTCT CGACTGCTGT AGAACATCTC AAGAAGTCAC TTGAGTTGCT      660

AACAAATCCA TCGGCCGGTG CCGGTCACTG AATTTTATAT CTAATCTATG ACACTTGGGG      720

TTGATGTTAG TGCGTGTGTG TGTTCTCACC ACATTTGTGG GTTTGTTTAT TAACTTTTCA      780

GGCTCAGACT TCGTTTACAA AGAAAATTTG TGTGAATTAT TCTTATTATC ATAAAATTTT      840

CCTTGCAACT TCGTGTACAT TCATACATAC ATAGGCAATG GAGTTCCTCT TCAGTCTTCA      900

CGTAAAGAGC GAGTGTGGGA CACGCACTCA TGTAGCGGGT GGTGTTAGTA CTCGAGGTTG      960

GGCCTATATA AAAGCCCATA GAGGCCCGAA TTACTGAATT TAGCAGACAA GAATAGAAAG     1020

AGTGATGAAA CATGGAAGAA AACGTGTCTC TAGAGTCATG TCAAGTGTAA GACAGAGGAA     1080

GAGAGAAGAG ATGTGCGTCA AGACAAGGA AAGAGAGATG TCAATCGCTG CTTTCGTCGG     1140

CGCGTGCATG TCCGCCACGC ACATCAATCA AATCGATTCT TATTATTATT ACCTCATTAT     1200

ACTCTTTACT C                                                         1211
```

(2) INFORMATION FOR SEQ ID NO:24:

(i) SEQUENCE CHARACTERISTICS:
        (A) LENGTH: 1486 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:24:

```
TGCATGGGAA GTAATTTTAA TTAACCTATG TTTTAAACAT TTACATTATT TGGAATTAAT       60

ATTATATATA CACTATTCGA TTTTGTTTTC CTTCAATGTA ACATTACTCT GGCAAAAGTA      120
```

-continued

```
TTTATCGTAT AATATCTTTT ATTATAAATT TTTGATGTTT TAAAGATTAG TTTATCTCTT      180

TTGACCAAAA AGAAAGGAAA AGGGATTAGA TTTATCTCTA TGTGAACTTG ATTATACGAG      240

TTCGGATAAT CGGATCTCAA TGTGATATCC ATATTTCTTG CAAGACATAT CTCTCGTACA      300

CCTTTTATAT TTATATCCCG CAATCGTGAC AACTCTTAAT CATTCACTAC ATAATATTTC      360

CAACAACATT AAAAGATATT TATCTTAATT CTCTTTTCCT TAACACTAAC AAAGTAGCAT      420

GTCCATATAT ACTTTCGTTT TTTGAGCATG AGAAAATAGA TTTAACTTTA TAAGTTATAA      480

CCATTGTTTC AAATTAATGC AGATTCGAGT AATAATAATT TGAGATGCAA TAATGGTTGT      540

GTCATATCTT GATTGCTAAA CTTGATACCG CCATACCGGT AACGTGAAGG GAGAGCTTCC      600

AATTTGTATG CAAGCCTACA TCTGACCCAA TTGTTGGCCC AATATTAACC AACACCCACA      660

CTAAAAAAAA TACTATGGAG GGAGTAATCT ACATGCCTAC ATTCCAAAGC AGGCAATATC      720

GTTTTTTCAT GTCTGAAAAC GCAATTTTTT TTTCTAATTG TTAAGTTGGT TCAAAAGAAA      780

TGAACATGGG TAATAATAAA AATGATGTAT TTGTTTGCAA ACAGCAGTTC TCACTTGTCT      840

CTCTCTATAT GATGAAAGAC AATGTTGTAA TCTTTATAGG TTTCAATATA GCGGGTATAC      900

TTGGTGACAT AAAGCGTTAT GAAATTTTAA GCAGTAAATA GGAAATGATA AATGATTATT      960

AAATTCGTTA TTAAAAATGT AAGAAGGAAT AGTACAATAT AGAACGGTAA AAAAAATGGC     1020

AAACCATTTA CTTCAATAAG AAAGGTTAGC AACCACACTC AGCAAATGGG ACACATAGGA     1080

TCCGACGTGG TTTATATTAT AGTAGTCTGA TATTGTAGAG TCAATGGGTA TATTTGTCTT     1140

TTTCAAAGAC TCAGTTCCAT TGAAGCGTAG GTTACTTCTT TAAACAAGAC TCTGTTTTGA     1200

ATGATATTGT AAAGTTAAGG GGTACGTTTG TCTTTTTCAG GACAAAGCGA GACCATAGAT     1260

GACGTGTCAA CTGCTAATTT TCAAAAACTC GGTCTACAAA CCATAACCAA ACTTATTTAT     1320

TCAATTATTT CCGTCAAAAA AATATAATTT TCTTTTTGCA TCTCAATGGA TTGATTCCAT     1380

GTGCCAAGTG TTGGTGTTCA TGAGAAAATT AGTCGCAGCT GATGACAACA AACATCAAGC     1440

ATTTATAATT TATATAACAC TCACGAGTGC CTCTTTCTTT GGATCC                   1486
```

(2) INFORMATION FOR SEQ ID NO:25:

(i) SEQUENCE CHARACTERISTICS:
        (A) LENGTH: 62 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:25:

```
TTTACTCTAA GACAAACACA TACATTTGCA CTCAGTCTAG AGACAAAGAG AGAGAGCCAT       60

GG                                                                     62
```

(2) INFORMATION FOR SEQ ID NO:26:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:26:

```
AGTGCCTCTT TCTTTATCTA CCTCGTCTCC TAATCACAAA CACACACAAA TCTCTGAAGT       60
```

ACCATG                                                                  66

(2) INFORMATION FOR SEQ ID NO:27:

(i) SEQUENCE CHARACTERISTICS:
        (A) LENGTH: 1266 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:27:

CGATCCACCC CATGACTCGA ATGATGACTC CAGCCACCAT CAATTCCCTG AAGTGCCACA         60

ACACCCTCTA CCTCCCAGGT TTTATGACAA TCCGACCAAC GATTATCCCG CAGATGTCCC        120

ACCTCCACCA CCGTCTTCTT ACCCTTCCAA CGATCATCTT CCCCCTCCCA CAGGACCATC        180

AGACTCCCCT TACCCGCATC CTTACAGTCA TCAACCATAC CACCAAGACC CGCCAAAACA        240

CATGCCGCCA CCGCAAAACT ACTCATCTCA TGAGCCTTCT CCAAATTCTC TCCCTAATTT        300

CCAATCTTAT CCTAGCTTTA GTGAGAGCAG CCTCCCATCC ACTTCTCCCC ACTACCCTTC        360

TCACTACCAA AACCCAGAAC CTTACTATTC TTCTCCGCAC TCTGCACCTG CTCCTTCTTC        420

CACAAGCTTC TGCTCTGCTC CTCCTCCTCC ACCTTACTCA TCAAACGGGC GTATCAATAT        480

TGCTCCCGTG CTAGATCCTG CACCGAGTTC AGCTCAGAAG TACCATTACG ATAGCAGCTA        540

CCAGCCAGGG CCTGAGAAGG TTGCAGAGGC ACTCAAGGCT GCTAGATTCG CTGTGGGAGC        600

TTTGGCTTTT GATGAAGTCT CGACTGCTGT AGAACATCTC AAGAAGTCAC TTGAGTTGCT        660

AACAAATCCA TCGGCCGGTG CCGGTCACTG AATTTTATAT CTAATCTATG ACACTTGGGG        720

TTGATGTTAG TGCGTGTGTG TGTTCTCACC ACATTTGTGG GTTTGTTTAT TAACTTTTCA        780

GGCTCAGACT TCGTTTACAA AGAAAATTTG TGTGAATTAT TCTTATTATC ATAAAATTTT        840

CCTTGCAACT TCGTGTACAT TCATACATAC ATAGGCAATG GAGTTCCTCT TCAGTCTTCA        900

CGTAAAGAGC GAGTGTGGGA CACGCACTCA TGTAGCGGGT GGTGTTAGTA CTCGAGGTTG        960

GGCCTATATA AAAGCCCATA GAGGCCCGAA TTACTGAATT TAGCAGACAA GAATAGAAAG       1020

AGTGATGAAA CATGGAAGAA AACGTGTCTC TAGAGTCATG TCAAGTGTAA GACAGAGGAA       1080

GAGAGAAGAG ATGTGCGTCA AAGACAAGGA AAGAGAGATG TCAATCGCTG CTTTCGTCGG       1140

CGCGTGCATG TCCGCCACGC ACATCAATCA AATCGATTCT TATTATTATT ACCTCATTAT       1200

ACTCTTTACT CTAAGACAAA CACATACATT TGCACTCAGT CTAGAGACAA AGAGAGAGAG       1260

CCATGG                                                                 1266

(2) INFORMATION FOR SEQ ID NO:28:

(i) SEQUENCE CHARACTERISTICS:
        (A) LENGTH: 1532 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:28:

TGCATGGGAA GTAATTTTAA TTAACCTATG TTTTAAACAT TTACATTATT TGGAATTAAT         60

ATTATATATA CACTATTCGA TTTTGTTTTC CTTCAATGTA ACATTACTCT GGCAAAAGTA        120

TTTATCGTAT AATATCTTTT ATTATAAATT TTTGATGTTT TAAAGATTAG TTTATCTCTT        180

TTGACCAAAA AGAAAGGAAA AGGGATTAGA TTTATCTCTA TGTGAACTTG ATTATACGAG        240

```
TTCGGATAAT CGGATCTCAA TGTGATATCC ATATTTCTTG CAAGACATAT CTCTCGTACA      300

CCTTTTATAT TTATATCCCG CAATCGTGAC AACTCTTAAT CATTCACTAC ATAATATTTC      360

CAACAACATT AAAAGATATT TATCTTAATT CTCTTTTCCT TAACACTAAC AAAGTAGCAT      420

GTCCATATAT ACTTTCGTTT TTTGAGCATG AGAAAATAGA TTTAACTTTA TAAGTTATAA      480

CCATTGTTTC AAATTAATGC AGATTCGAGT AATAATAATT TGAGATGCAA TAATGGTTGT      540

GTCATATCTT GATTGCTAAA CTTGATACCG CCATACCGGT AACGTGAAGG GAGAGCTTCC      600

AATTTGTATG CAAGCCTACA TCTGACCCAA TTGTTGGCCC AATATTAACC AACACCCACA      660

CTAAAAAAAA TACTATGGAG GGAGTAATCT ACATGCCTAC ATTCCAAAGC AGGCAATATC      720

GTTTTTTCAT GTCTGAAAAC GCAATTTTTT TTTCTAATTG TTAAGTTGGT TCAAAAGAAA      780

TGAACATGGG TAATAATAAA AATGATGTAT TTGTTTGCAA ACAGCAGTTC TCACTTGTCT      840

CTCTCTATAT GATGAAAGAC AATGTTGTAA TCTTTATAGG TTTCAATATA GCGGGTATAC      900

TTGGTGACAT AAAGCGTTAT GAAATTTTAA GCAGTAAATA GGAAATGATA ATGATTATT       960

AAATTCGTTA TTAAAAATGT AAGAAGGAAT AGTACAATAT AGAACGGTAA AAAAAATGGC     1020

AAACCATTTA CTTCAATAAG AAAGGTTAGC AACCACACTC AGCAAATGGG ACACATAGGA     1080

TCCGACGTGG TTTATATTAT AGTAGTCTGA TATTGTAGAG TCAATGGGTA TATTTGTCTT     1140

TTTCAAAGAC TCAGTTCCAT TGAAGCGTAG GTTACTTCTT TAAACAAGAC TCTGTTTTGA     1200

ATGATATTGT AAAGTTAAGG GGTACGTTTG TCTTTTTCAG GACAAAGCGA GACCATAGAT     1260

GACGTGTCAA CTGCTAATTT TCAAAAACTC GGTCTACAAA CCATAACCAA ACTTATTTAT     1320

TCAATTATTT CCGTCAAAAA AATATAATTT TCTTTTTGCA TCTCAATGGA TTGATTCCAT     1380

GTGCCAAGTG TTGGTGTTCA TGAGAAAATT AGTCGCAGCT GATGACAACA AACATCAAGC     1440

ATTTATAATT TATATAACAC TCACGAGTGC CTCTTTCTTT ATCTACCTCG TCTCCTAATC     1500

ACAAACACAC ACAAATCTCT GAAGTACCAT GG                                   1532
```

(2) INFORMATION FOR SEQ ID NO:29:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:29:

```
TTATTATTAC CTC                                                          13
```

(2) INFORMATION FOR SEQ ID NO:30:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:30:

```
GAAGTCTATC ATCC                                                         14
```

(2) INFORMATION FOR SEQ ID NO:31:

(i) SEQUENCE CHARACTERISTICS:

(A) LENGTH: 16 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:31:

CACTCACGAG TGCCTC                                                        16

(2) INFORMATION FOR SEQ ID NO:32:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:32:

ACAAGAAGAA CCTGG                                                         15

(2) INFORMATION FOR SEQ ID NO:33:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:33:

ACCGAATTCA TGGCATTCGA CCTCAGCTCT                                         30

(2) INFORMATION FOR SEQ ID NO:34:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:34:

CGTGAGCTCT CACTAATTTC CAAGCCTTGA                                         30

(2) INFORMATION FOR SEQ ID NO:35:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:35:

ATTAACCCTC ACTAAAG                                                       17

(2) INFORMATION FOR SEQ ID NO:36:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:36:

AATACGACTC ACTATAG                                                    17

(2) INFORMATION FOR SEQ ID NO:37:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:37:

CATGCCATGG CTCTCTCTCT TTGTCTCTAG ACTG                                 34

(2) INFORMATION FOR SEQ ID NO:38:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:38:

CTAGCCATGG TACTTCAGAG ATTTGTGTG                                       29

(2) INFORMATION FOR SEQ ID NO:39:

(i) SEQUENCE CHARACTERISTICS:
        (A) LENGTH: 1248 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:39:

AAGCTCGATC CACCCCATGA CTCGAATGAT GACTCCAGCC ACCATCAATT CCCTGAAGTG      60

CCACAACACC CTCTACCTCC CAGGTTTTAT GACAATCCGA CCAACGATTA TCCCGCAGAT     120

GTCCCACCTC CACCACCGTC TTCTTACCCT TCCAACGATC ATCTTCCCCC TCCCACAGGA    180

CCATCAGACT CCCCTTACCC GCATCCTTAC AGTCATCAAC CATACCACCA AGACCCGCCA    240

AAACACATGC CGCCACCGCA AAACTACTCA TCTCATGAGC CTTCTCCAAA TTCTCTCCCT    300

AATTTCCAAT CTTATCCTAG CTTTAGTGAG AGCAGCCTCC CATCCACTTC TCCCCACTAC    360

CCTTCTCACT ACCAAAACCC AGAACCTTAC TATTCTTCTC CGCACTCTGC ACCTGCTCCT    420

TCTTCCACAA GCTTCTGCTC TGCTCCTCCT CCTCCACCTT ACTCATCAAA CGGGCGTATC    480

AATATTGCTC CCGTGCTAGA TCCTGCACCG AGTTCAGCTC AGAAGTACCA TTACGATAGC    540

AGCTACCAGC CAGGGCCTGA GAAGGTTGCA GAGGCACTCA AGGCTGCTAG ATTCGCTGTG    600

GGAGCTTTGG CTTTTGATGA AGTCTCGACT GCTGTAGAAC ATCTCAAGAA GTCACTTGAG    660

TTGCTAACAA ATCCATCGGC CGGTGCCGGT CACTGAATTT TATATCTAAT CTATGACACT    720

TGGGGTTGAT GTTAGTGCGT GTGTGTGTTC TCACCACATT TGTGGGTTTG TTTATTAACT    780

TTTCAGGCTC AGACTTCGTT TACAAAGAAA ATTTGTGTGA ATTATTCTTA TTATCATAAA    840

ATTTTCCTTG CAACTTCGTG TACATTCATA CATACATAGG CAATGGAGTT CCTCTTCAGT    900

```
CTTCACGTAA AGAGCGAGTG TGGGACACGC ACTCATGTAG CGGGTGGTGT TAGTACTCGA      960

GGTTGGGCCT ATATAAAAGC CCATAGAGGC CCGAATTACT GAATTTAGCA GACAAGAATA     1020

GAAAGAGTGA TGAAACATGG AAGAAAACGT GTCTCTAGAG TCATGTCAAG TGTAAGACAG     1080

AGGAAGAGAG AAGAGATGTG CGTCAAAGAC AAGGAAAGAG AGATGTCAAT CGCTGCTTTC     1140

GTCGGCGCGT GCATGTCCGC CACGCACATC AATCAAATCG ATTCTTATTA TTATTACCTC     1200

ATTATACTCT TTACTCCCTA GGCGCGATCC CCGGGTGGTC AGTTCCTT                  1248
```

(2) INFORMATION FOR SEQ ID NO:40:

(i) SEQUENCE CHARACTERISTICS:
        (A) LENGTH: 1307 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:40:

```
GGATCCACTA GTTCTAGAGC GGCCGCCACC GCGGTGGAGC TCGATCCACC CCATGACTCG       60

AATGATGACT CCAGCCACCA TCAATTCCCT GAAGTGCCAC AACACCCTCT ACCTCCCAGG      120

TTTTATGACA ATCCGACCAA CGATTATCCC GCAGATGTCC CACCTCCACC ACCGTCTTCT      180

TACCCTTCCA ACGATCATCT TCCCCCTCCC ACAGGACCAT CAGACTCCCC TTACCCGCAT      240

CCTTACAGTC ATCAACCATA CCACCAAGAC CCGCCAAAAC ACATGCCGCC ACCGCAAAAC      300

TACTCATCTC ATGAGCCTTC TCCAAATTCT CTCCCTAATT TCCAATCTTA TCCTAGCTTT      360

AGTGAGAGCA GCCTCCCATC CACTTCTCCC CACTACCCTT CTCACTACCA AAACCCAGAA      420

CCTTACTATT CTTCTCCGCA CTCTGCACCT GCTCCTTCTT CCACAAGCTT CTGCTCTGCT      480

CCTCCTCCTC CACCTTACTC ATCAAACGGG CGTATCAATA TTGCTCCCGT GCTAGATCCT      540

GCACCGAGTT CAGCTCAGAA GTACCATTAC GATAGCAGCT ACCAGCCAGG GCCTGAGAAG      600

GTTGCAGAGG CACTCAAGGC TGCTAGATTC GCTGTGGGAG CTTTGGCTTT TGATGAAGTC      660

TCGACTGCTG TAGAACATCT CAAGAAGTCA CTTGAGTTGC TAACAAATCC ATCGGCCGGT      720

GCCGGTCACT GAATTTTATA TCTAATCTAT GACACTTGGG GTTGATGTTA GTGCGTGTGT      780

GTGTTCTCAC CACATTTGTG GGTTTGTTTA TTAACTTTTC AGGCTCAGAC TTCGTTTACA      840

AAGAAAATTT GTGTGAATTA TTCTTATTAT CATAAAATTT TCCTTGCAAC TTCGTGTACA      900

TTCATACATA CATAGGCAAT GGAGTTCCTC TTCAGTCTTC ACGTAAAGAG CGAGTGTGGG      960

ACACGCACTC ATGTAGCGGG TGGTGTTAGT ACTCGAGGTT GGGCCTATAT AAAGCCCAT      1020

AGAGGCCCGA ATTACTGAAT TTAGCAGACA AGAATAGAAA GAGTGATGAA ACATGGAAGA     1080

AAACGTGTCT CTAGAGTCAT GTCAAGTGTA AGACAGAGGA AGAGAAGA GATGTGCGTC       1140

AAAGACAAGG AAAGAGAGAT GTCAATCGCT GCTTTCGTCG GCGCGTGCAT GTCCGCCACG     1200

CACATCAATC AAATCGATTC TTATTATTAT TACCTCATTA TACTCTTTAC TCTAAGACAA     1260

ACACATACAT TTGCACTCAG TCTAGAGACA AAGAGAGAGA GCCATGG                   1307
```

(2) INFORMATION FOR SEQ ID NO:41:

(i) SEQUENCE CHARACTERISTICS:
        (A) LENGTH: 1511 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:41:

| | | | | | |
|---|---|---|---|---|---|
| TCTAGATGCA | TGGGAAGTAA | TTTTAATTAA | CCTATGTTTT | AAACATTTAC | ATTATTTGGA | 60 |
| ATTAATATTA | TATATACACT | ATTCGATTTT | GTTTTCCTTC | AATGTAACAT | TACTCTGGCA | 120 |
| AAAGTATTTA | TCGTATAATA | TCTTTTATTA | TAAATTTTTG | ATGTTTTAAA | GATTAGTTTA | 180 |
| TCTCTTTTGA | CCAAAAAGAA | AGGAAAAGGG | ATTAGATTTA | TCTCTATGTG | AACTTGATTA | 240 |
| TACGAGTTCG | GATAATCGGA | TCTCAATGTG | ATATCCATAT | TTCTTGCAAG | ACATATCTCT | 300 |
| CGTACACCTT | TTATATTTAT | ATCCCGCAAT | CGTGACAACT | CTTAATCATT | CACTACATAA | 360 |
| TATTTCCAAC | AACATTAAAA | GATATTTATC | TTAATTCTCT | TTTCCTTAAC | ACTAACAAAG | 420 |
| TAGCATGTCC | ATATATACTT | TCGTTTTTTG | AGCATGAGAA | AATAGATTTA | ACTTTATAAG | 480 |
| TTATAACCAT | TGTTTCAAAT | TAATGCAGAT | TCGAGTAATA | ATAATTTGAG | ATGCAATAAT | 540 |
| GGTTGTGTCA | TATCTTGATT | GCTAAACTTG | ATACCGCCAT | ACCGGTAACG | TGAAGGGAGA | 600 |
| GCTTCCAATT | TGTATGCAAG | CCTACATCTG | ACCCAATTGT | TGGCCCAATA | TTAACCAACA | 660 |
| CCCACACTAA | AAAAAATACT | ATGGAGGGAG | TAATCTACAT | GCCTACATTC | CAAAGCAGGC | 720 |
| AATATCGTTT | TTTCATGTCT | GAAAACGCAA | TTTTTTTTTC | TAATTGTTAA | GTTGGTTCAA | 780 |
| AAGAAATGAA | CATGGGTAAT | AATAAAAATG | ATGTATTTGT | TTGCAAACAG | CAGTTCTCAC | 840 |
| TTGTCTCTCT | CTATATGATG | AAAGACAATG | TTGTAATCTT | TATAGGTTTC | AATATAGCGG | 900 |
| GTATACTTGG | TGACATAAAG | CGTTATGAAA | TTTTAAGCAG | TAAATAGGAA | ATGATAAATG | 960 |
| ATTATTAAAT | TCGTTATTAA | AAATGTAAGA | AGGAATAGTA | CAATATAGAA | CGGTAAAAAA | 1020 |
| AATGGCAAAC | CATTTACTTC | AATAAGAAAG | GTTAGCAACC | ACACTCAGCA | AATGGGACAC | 1080 |
| ATAGGATCCG | ACGTGGTTTA | TATTATAGTA | GTCTGATATT | GTAGAGTCAA | TGGGTATATT | 1140 |
| TGTCTTTTTC | AAAGACTCAG | TTCCATTGAA | GCGTAGGTTA | CTTCTTTAAA | CAAGACTCTG | 1200 |
| TTTTGAATGA | TATTGTAAAG | TTAAGGGGTA | CGTTTGTCTT | TTTCAGGACA | AAGCGAGACC | 1260 |
| ATAGATGACG | TGTCAACTGC | TAATTTTCAA | AAACTCGGTC | TACAAACCAT | AACCAAACTT | 1320 |
| ATTTATTCAA | TTATTTCCGT | CAAAAAAATA | TAATTTTCTT | TTTGCATCTC | AATGGATTGA | 1380 |
| TTCCATGTGC | CAAGTGTTGG | TGTTCATGAG | AAAATTAGTC | GCAGCTGATG | ACAACAAACA | 1440 |
| TCAAGCATTT | ATAATTTATA | TAACACTCAC | GAGTGCCTCT | TTCTTTGGAT | CCGCGGGGTG | 1500 |
| GTCAGTTCCT | T | | | | | 1511 |

(2) INFORMATION FOR SEQ ID NO:42:

(i) SEQUENCE CHARACTERISTICS:
        (A) LENGTH: 1538 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:42:

| | | | | | |
|---|---|---|---|---|---|
| TCTAGATGCA | TGGGAAGTAA | TTTTAATTAA | CCTATGTTTT | AAACATTTAC | ATTATTTGGA | 60 |
| ATTAATATTA | TATATACACT | ATTCGATTTT | GTTTTCCTTC | AATGTAACAT | TACTCTGGCA | 120 |
| AAAGTATTTA | TCGTATAATA | TCTTTTATTA | TAAATTTTTG | ATGTTTTAAA | GATTAGTTTA | 180 |
| TCTCTTTTGA | CCAAAAAGAA | AGGAAAAGGG | ATTAGATTTA | TCTCTATGTG | AACTTGATTA | 240 |
| TACGAGTTCG | GATAATCGGA | TCTCAATGTG | ATATCCATAT | TTCTTGCAAG | ACATATCTCT | 300 |

-continued

| | | | | |
|---|---|---|---|---|
| CGTACACCTT | TTATATTTAT | ATCCCGCAAT | CGTGACAACT | CTTAATCATT | CACTACATAA | 360 |
| TATTTCCAAC | AACATTAAAA | GATATTTATC | TTAATTCTCT | TTTCCTTAAC | ACTAACAAAG | 420 |
| TAGCATGTCC | ATATATACTT | TCGTTTTTTG | AGCATGAGAA | AATAGATTTA | ACTTTATAAG | 480 |
| TTATAACCAT | TGTTTCAAAT | TAATGCAGAT | TCGAGTAATA | ATAATTTGAG | ATGCAATAAT | 540 |
| GGTTGTGTCA | TATCTTGATT | GCTAAACTTG | ATACCGCCAT | ACCGGTAACG | TGAAGGGAGA | 600 |
| GCTTCCAATT | TGTATGCAAG | CCTACATCTG | ACCCAATTGT | TGGCCCAATA | TTAACCAACA | 660 |
| CCCACACTAA | AAAAAATACT | ATGGAGGGAG | TAATCTACAT | GCCTACATTC | CAAAGCAGGC | 720 |
| AATATCGTTT | TTTCATGTCT | GAAAACGCAA | TTTTTTTTTC | TAATTGTTAA | GTTGGTTCAA | 780 |
| AAGAAATGAA | CATGGGTAAT | AATAAAAATG | ATGTATTTGT | TTGCAAACAG | CAGTTCTCAC | 840 |
| TTGTCTCTCT | CTATATGATG | AAAGACAATG | TTGTAATCTT | TATAGGTTTC | AATATAGCGG | 900 |
| GTATACTTGG | TGACATAAAG | CGTTATGAAA | TTTTAAGCAG | TAAATAGGAA | ATGATAAATG | 960 |
| ATTATTAAAT | TCGTTATTAA | AAATGTAAGA | AGGAATAGTA | CAATATAGAA | CGGTAAAAAA | 1020 |
| AATGGCAAAC | CATTTACTTC | AATAAGAAAG | GTTAGCAACC | ACACTCAGCA | AATGGGACAC | 1080 |
| ATAGGATCCG | ACGTGGTTTA | TATTATAGTA | GTCTGATATT | GTAGAGTCAA | TGGGTATATT | 1140 |
| TGTCTTTTTC | AAAGACTCAG | TTCCATTGAA | GCGTAGGTTA | CTTCTTTAAA | CAAGACTCTG | 1200 |
| TTTTGAATGA | TATTGTAAAG | TTAAGGGGTA | CGTTTGTCTT | TTTCAGGACA | AAGCGAGACC | 1260 |
| ATAGATGACG | TGTCAACTGC | TAATTTTCAA | AAACTCGGTC | TACAAACCAT | AACCAAACTT | 1320 |
| ATTTATTCAA | TTATTTCCGT | CAAAAAAATA | TAATTTTCTT | TTTGCATCTC | AATGGATTGA | 1380 |
| TTCCATGTGC | CAAGTGTTGG | TGTTCATGAG | AAAATTAGTC | GCAGCTGATG | ACAACAAACA | 1440 |
| TCAAGCATTT | ATAATTTATA | TAACACTCAC | GAGTGCCTCT | TTCTTTATCT | ACCTCGTCTC | 1500 |
| CTAATCACAA | ACACACACAA | ATCTCTGAAG | TACCATGG | | | 1538 |